US012534439B2

(12) United States Patent
Paraiso et al.

(10) Patent No.: US 12,534,439 B2
(45) Date of Patent: Jan. 27, 2026

(54) XANTHOHUMOL DERIVATIVES AND METHODS FOR MAKING AND USING

(71) Applicant: Oregon State University, Corvallis, OR (US)

(72) Inventors: Ines L. Paraiso, Corvallis, OR (US); Jan Frederik Stevens, Corvallis, OR (US); Paul R. Blakemore, Corvallis, OR (US); Luce M. Mattio, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 405 days.

(21) Appl. No.: 18/354,848

(22) Filed: Jul. 19, 2023

(65) Prior Publication Data

US 2024/0051922 A1 Feb. 15, 2024

Related U.S. Application Data

(63) Continuation of application No. PCT/US2022/015663, filed on Feb. 8, 2022.

(60) Provisional application No. 63/147,413, filed on Feb. 9, 2021.

(51) Int. Cl.
*C07D 231/12* (2006.01)
*C07D 261/08* (2006.01)

(52) U.S. Cl.
CPC ......... *C07D 231/12* (2013.01); *C07D 261/08* (2013.01)

(58) Field of Classification Search
CPC ............................ C07D 231/12; C07D 261/08
See application file for complete search history.

(56) References Cited

U.S. PATENT DOCUMENTS

2010/0029757 A1 2/2010 Hellerbrand
2011/0046147 A1 2/2011 Hartmann et al.
2016/0008298 A1 1/2016 Stevens

FOREIGN PATENT DOCUMENTS

WO WO 2017/151469 9/2017
WO WO 2019/136147 7/2019

OTHER PUBLICATIONS

Extended European Search Report for European Application No. 22753210.8, mailed Dec. 20, 2024.
Marin et al., "Recent Trends in the Pharmacological Activity of Isoprenyl Phenolics," *Current Medicinal Chemistry*, 20(2):272-279 (Jan. 1, 2013).
Stevens et al., "Xanthohumol and related prenylflavonoids from hops and beer: to your good health!," *Phytochemistry*, 65(10):1317-1330 (May 28, 2004).
International Search Report dated May 11, 2022 from International Application No. PCT/US2022/015663 (3 pages).
Miranda et al., "Non-estrogenic Xanthohumol Derivatives Mitigate Insulin Resistance and Cognitive Impairment in High-Fat-Diet-induced Obese Mice," *Scientific Reports* 8:613 (pp. 1-17), 2018, published online Jan. 12, 2018.
Paraiso et al., "Xanthohumol Pyrazole Derivative Improves Diet-Induced Obesity and Induces Energy Expenditure in High-Fat Diet-Fed Mice," *ACS Pharmacology & Translational Science* 4:1782-1793, 2021, published Nov. 4, 2021.
Saito et al., "Identification of 10-dehydrooxyglycyuralin E as a selective human estrogen receptor alpha partial agonist," *Bioorganic Chemistry* 88:1-9, 2019 available online May 8, 2019.
Written Opinion dated May 11, 2022 from International Application No. PCT/US2022/015663 (5 pages).
Yang et al. "Conformational modulation of the farnesoid X receptor by prenylflavonoids: Insights from hydrogen deuterium exchange mass spectrometry (HDX-MS), fluorescence titration and molecular docking studies," *Biochimica et Biophysica Acta* 1864:12 (pp. 1667-1677) 2016 available online Sep. 3, 2016.

*Primary Examiner* — Kamal A Saeed
(74) *Attorney, Agent, or Firm* — Klarquist Sparkman, LLP

(57) ABSTRACT

Representative xanthohumol derivatives have been made and have been tested in vivo in mice. Such derivatives have a number of important medicinal benefits, including improving glucose tolerance and decreasing weight gain by increasing energy expenditure and locomotor activity in treated subjects. Disclosed derivatives also may function as mitochondrial uncouplers. Representative compounds include 4-(5-(4-hydroxyphenyl)-1-methyl-1H-pyrazol-3-yl)-5-methoxy-2-(3-methylbut-2-en-1-yl)benzene-1,3-diol and 4-(5-(4-hydroxyphenyl)isoxazole-3-yl)-5-methoxy-2-(3-methylbut-2-en-1-yl)benzene-1,3-diol.

19 Claims, 47 Drawing Sheets

1: $C_{22}H_{26}N_2O_4$ (382.5)

2: $C_{26}H_{30}N_2O_6$ (466.5)

13C NMR: 175 MHz, $d_6$-DMSO (ref. 39.5 ppm)

4: $C_{22}H_{24}N_2O_4$ (380.4)

¹H NMR: 700 MHz, $d_6$-DMSO (ref. 2.50 ppm)

5: $C_{21}H_{21}NO_5$ (367.4)

XN isoxazole

XANTHOHUMOL DERIVATIVES AND METHODS FOR MAKING AND USING

CROSS REFERENCE TO RELATED APPLICATION

This application is a continuation of International Application No. PCT/US2022/015663, filed on Feb. 8, 2022, which was published in English under PCT Article 21(2), which in turn claims the benefit of the earlier filing date of U.S. Patent Application No. 63/147,413, filed on Feb. 9, 2021, and includes information related to disclosure provided by assignee's prior U.S. patent applications, No. 62/024,438 and Ser. No. 14/798,393. Each of assignee's prior applications is incorporated herein by reference.

FIELD

The present disclosure concerns synthetic derivatives of xanthohumol and methods of making and using such derivatives to treat, ameliorate, or prevent maladies, particularly metabolic maladies and syndromes, including obesity.

BACKGROUND

Cardiovascular disease, the number one cause of death worldwide, is responsible for hundreds of thousands of deaths annually and billions of dollars in annual medical care costs. An individual's risk of cardiovascular disease and type II diabetes (T2D) is strongly correlated to a series of risk factors, collectively referred to as metabolic syndrome, including abdominal obesity, insulin insensitivity, elevated plasma triglycerides, hypertension and low plasma high-density lipoproteins (HDLs). Any combination of three or more of these conditions greatly multiplies cardiovascular disease risk.

Obesity is often the result of an imbalance between energy intake and energy expenditure (EE), which influences daily energy homeostasis and ultimately leads to weight gain. Heat production in brown adipose tissue (BAT) contributes to cold defense, stress-induced increases in body temperature, and energy balance. The concept of managing obesity by stimulating thermogenesis and EE is a focus of considerable attention. Thermogenic and fat-oxidizing molecules are being investigated for their anti-obesity properties and include methylxanthines, polyphenols, minerals, proteins/amino acids, carbohydrates/sugars, and fats/fatty acids. In recent studies, flavonoids have been found to induce white adipose tissue (WAT) browning and promote energy balance in humans and animals through non-shivering thermogenesis. The thermogenic potentials of these products range from marginal to modest, but a safe increase to 10-15% above daily EE is expected to have significant impact on weight management in humans.

Successfully treating metabolic syndrome medicinally remains a significant challenge. There has been, for example, substantial interest regarding the various health benefits of flavonoids, such as xanthohumol (shown below).

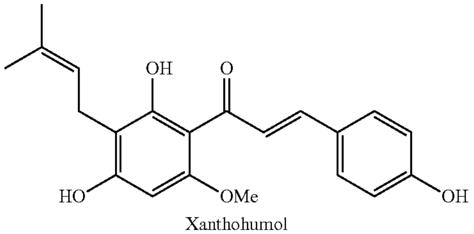 [SMILES: COc1cc(O)c(CC=C(C)C)c(O)c1C(=O)/C=C/c1ccc(O)cc1]

Xanthohumol

Hops (*Humulus lupulus*) are a rich source of bioactive flavonoids and chalcones, including xanthohumol. Anti-inflammatory, antioxidant, antiangiogenic, antiproliferative and apoptotic effects, mainly assessed in vitro, reasonably suggest that xanthohumol has a chemopreventive activity. Xanthohumol reduces weight gain in high-fat diet (HFD)-fed C57BL/6J mice, enhances lipid and glucose metabolism in KK-A(y) mice, and improves cognitive function. Several in vivo studies have shown that oral administration of xanthohumol attenuates weight gain in obese male Zucker fa/fa rats, in KK-A(y) mice, and to various extents in obese C57BL/6(J) mice depending on the diet, dose, and formulation. Furthermore, oral administration of xanthohumol has been shown to lower the hepatic triglyceride content in KK-A(y) mice and in diet-induced obese C57BL/6J mice. In these mouse models, xanthohumol treatment also improved glucose intolerance and cognitive performance. Xanthohumol increases the thermogenic uncoupling protein UCP1 in preadipocytes, resulting in the upregulation of mitochondrial uncoupling and oxygen consumption in vitro. The mild mitochondrial uncoupling effect of xanthohumol observed in vitro suggests that xanthohumol might also induce EE in vivo. However, due to the α,-unsaturated ketone in its chemical structure, XN can spontaneously form a stable isomer, isoxanthohumol (IX), the biological precursor to the potent phytoestrogen, 8-prenylnaringenin (8PN). As a result, estrogenic side effects might be associated with XN administration in humans.

Pyrazoles are five-membered heterocycles that have interesting pharmacological properties, and are reported to have CNS depressant, neuroleptic, anti-Alzheimer's, antihypertensive, analgesic, antidiabetic, anticancer and antimicrobial activities. Pyrazole derivatives are used as nonsteroidal anti-inflammatory drugs clinically, such as: phenazone (analgesic and antipyretic); metamizole (analgesic and antipyretic); phenylbutazone (anti-inflammatory, antipyretic and mainly used to treat osteoarthritis, rheumatoid arthritis, spondylitis and Reiter's disease); sulfinpyrazone (chronic gout); sildenafil (erectile dysfunction and pulmonary arterial hypertension); and rimonabant (obesity).

SUMMARY

The present disclosure concerns new compounds, and compositions comprising such compounds, as inducers of energy expenditure (EE) for managing client-induced obesity and insulin resistance. For example, in a comparative study, with xanthohumol (also referred to herein as XN), 4-(5-(4-hydroxyphenyl)-1-methyl-1H-pyrazol-3-yl)-5-methoxy-2-(3(methylbut-2-en-1-yl)benzene1,3-diol (also referred to herein as XP) uncoupled oxidative phosphorylation in C2C12 cells. The structure of XP is provided below.

XP

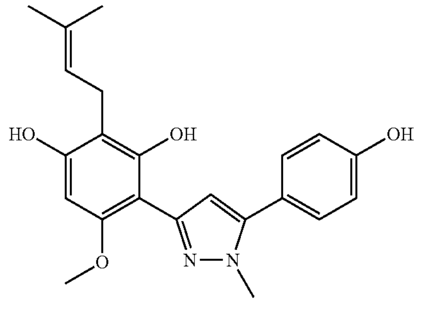

In HFD-fed mice, XP improved glucose tolerance and decreased weight gain by increasing EE and locomotor activity. Using an untargeted metabolomics approach, XP and XN were found to reduce purine metabolites and other energy metabolites in the plasma of HFD-fed mice. The induction of locomotor activity was associated with increased inosine monophosphate in the cortex of XP-treated mice. Together, these results establish that XP, better than XN, affects mitochondrial respiration and cellular energy metabolism to prevent obesity in HFD-fed mice.

Accordingly, certain disclosed embodiments concern xanthohumol derivatives that include a cyclic moiety, such as a pyrazole or an isoxazole moiety, which prevents xanthohumol isomerization and metabolic conversion into compounds exerting estrogenic adverse effects. Representative xanthohumol derivatives have been made and have been tested in vivo in mice. Such derivatives have a number of important medicinal benefits, including improving glucose tolerance and decreasing weight gain by increasing energy expenditure and locomotor activity in treated subjects. Disclosed derivatives also may function as mitochondrial uncouplers.

Certain disclosed embodiments concern compounds having a Formula I

Formula I

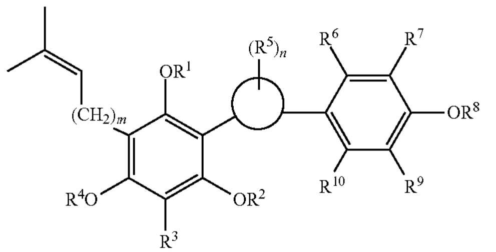

where m is 1-10; n=0 up to the number of ring positions available for substitution; $R^1$-$R^4$ and $R^6$-$R^{10}$ are independently selected from H, $C_1$-$C_{10}$ alkyl, a protecting group or a promoiety; $R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl; and the circle is a cyclic structure having 4 to 6 ring atoms. Values for m and n are more typically 1, 2 or 3. Certain representative embodiments have m and n equal to 1 with $R^1$-$R^{10}$ independently being H or methyl. The cyclic structure may be a 5-membered heterocycle or a 5-membered heteroaryl, such as a pyrazole or an isoxazole.

Certain disclosed compounds may have a Formula II

Formula II

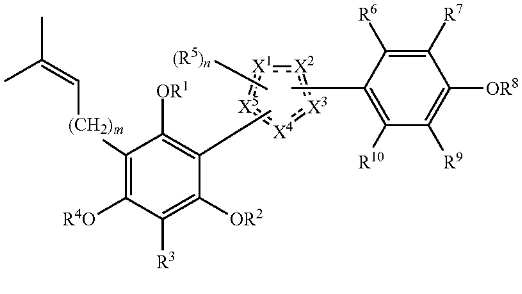

where m and n are 1, 2 or 3; $R^1$-$R^4$ and $R^6$-$R^{10}$ are independently selected from H, $C_1$-$C_{10}$ alkyl, a protecting group or a promoiety; $R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl; and X is independently C, N, O, S, or combinations thereof. Compounds having a formula II can also have a formula

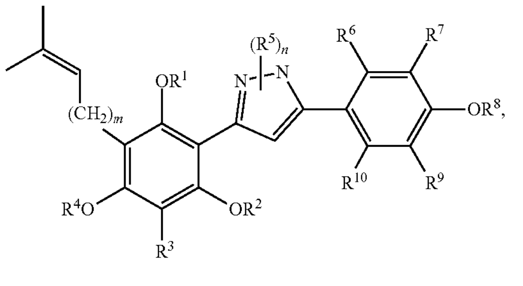

or a formula

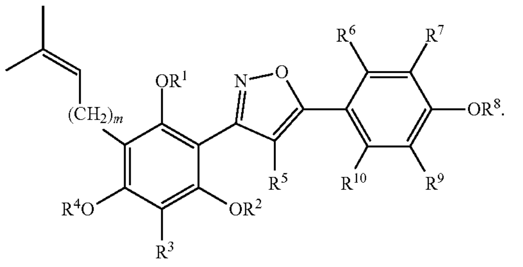

Representative compounds satisfying these general formulas include 4-(5-(4-hydroxyphenyl)-1-methyl-1H-pyrazol-3-yl)-5-methoxy-2-(3-methylbut-2-en-1-yl)benzene-1,3-diol

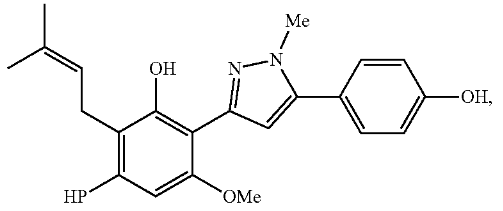

and 4-(5-(4-hydroxyphenyl)isoxazole-3-yl)-5-methoxy-2-(3-methylbut-2-en-1-yl)benzene-1,3-diol

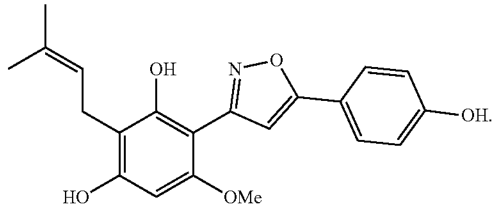 [SMILES: COc1cc(O)c(CC=C(C)C)c(O)c1-c1cc(-c2ccc(O)cc2)on1]

Disclosed embodiments also include compositions comprising a disclosed compound, or compounds, and a pharmaceutically acceptable excipient, such as an excipient selected from binding agents, fillers, lubricants, emulsifiers/solubilizers, coloring agents, flavoring agents, and combinations thereof. Such compositions can also comprise at least one additional active agent. Particular embodiments are formulated for administration as a dietary supplement or drug.

The present invention also includes embodiments of a method comprising administering a disclosed compound or a composition comprising a disclosed compound to a subject. The method may comprise treating, ameliorating, or preventing metabolic syndrome, obesity, diabetes, and/or cardiovascular disease. For example, administering the compound or a composition comprising the compound to a subject reduces weight gain or reduces body weight in the subject relative to a subject that is not administered the compound or a composition comprising the compound. The method also may improve glucose metabolism or glucose tolerance in a subject. The method may, for example, reduce a subject's insulin resistance score by about 50% or more, such as up to about 80%. The method may also increase energy expenditure and ambulatory locomotor activity in a subject, as well as increasing the subject's mean respiratory exchange ratio. Disclosed compounds also may have anti-inflammatory activity as indicated by the attenuation of LPS-induced inflammation in macrophages-like cells, and may beneficially reduce monocyte-chemoattractant protein 1 concentration in a subject.

A particular disclosed method embodiment comprises administering an effective amount of 4-(5-(4-hydroxyphenyl)-1-methyl-1H-pyrazol-3-yl)-5-methoxy-2-(3-methylbut-2-en-1-yl)benzene-1,3-diol

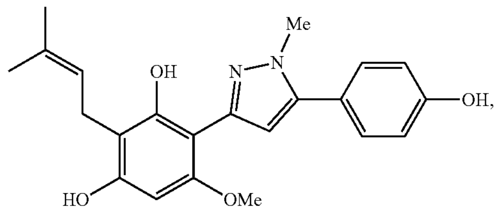 [SMILES: COc1cc(O)c(CC=C(C)C)c(O)c1-c1cc(-c2ccc(O)cc2)n(C)n1]

or a composition comprising 4-(5-(4-hydroxyphenyl)-1-methyl-1H-pyrazol-3-yl)-5-methoxy-2-(3-methylbut-2-en-1-yl)benzene-1,3-diol, to a subject to improve glucose tolerance, decrease diet-induced obesity, and/or to induce increased energy expenditure relative to subject that is not administered 4-(5-(4-hydroxyphenyl)-1-methyl-1H-pyrazol-3-yl)-5-methoxy-2-(3-methylbut-2-en-1-yl)benzene-1,3-diol.

The foregoing and other objects, features, and advantages of the invention will become more apparent from the following detailed description, which proceeds with reference to the accompanying figures.

BRIEF DESCRIPTION OF THE DRAWINGS

FIGS. 21A-210 provide relative abundances of (A) adenosine, (B) asparatate, (C) choline, (D) carnitine, (E) oruinyl-carnitine, (F) N-acetyl-aspartate, (G) hypusine, (H) glutamate, (I) S-adenosyl-methionine, (J) spermidine, (K) taurine, (L) glycerolphosphate, (M) reduced glutathione, oxidized glutathione (N) and reduced/oxidized glutathione ratio (0) in the cortex of HFD-fed mice untreated, treated with XP or treated with XN, where significant differences are marked *$p<0.05$, $p<0.01$, and *$p<0.001$ for effect of treatment, one-way ANOVA.

DETAILED DESCRIPTION

I. Explanation of Terms

Figure 1:
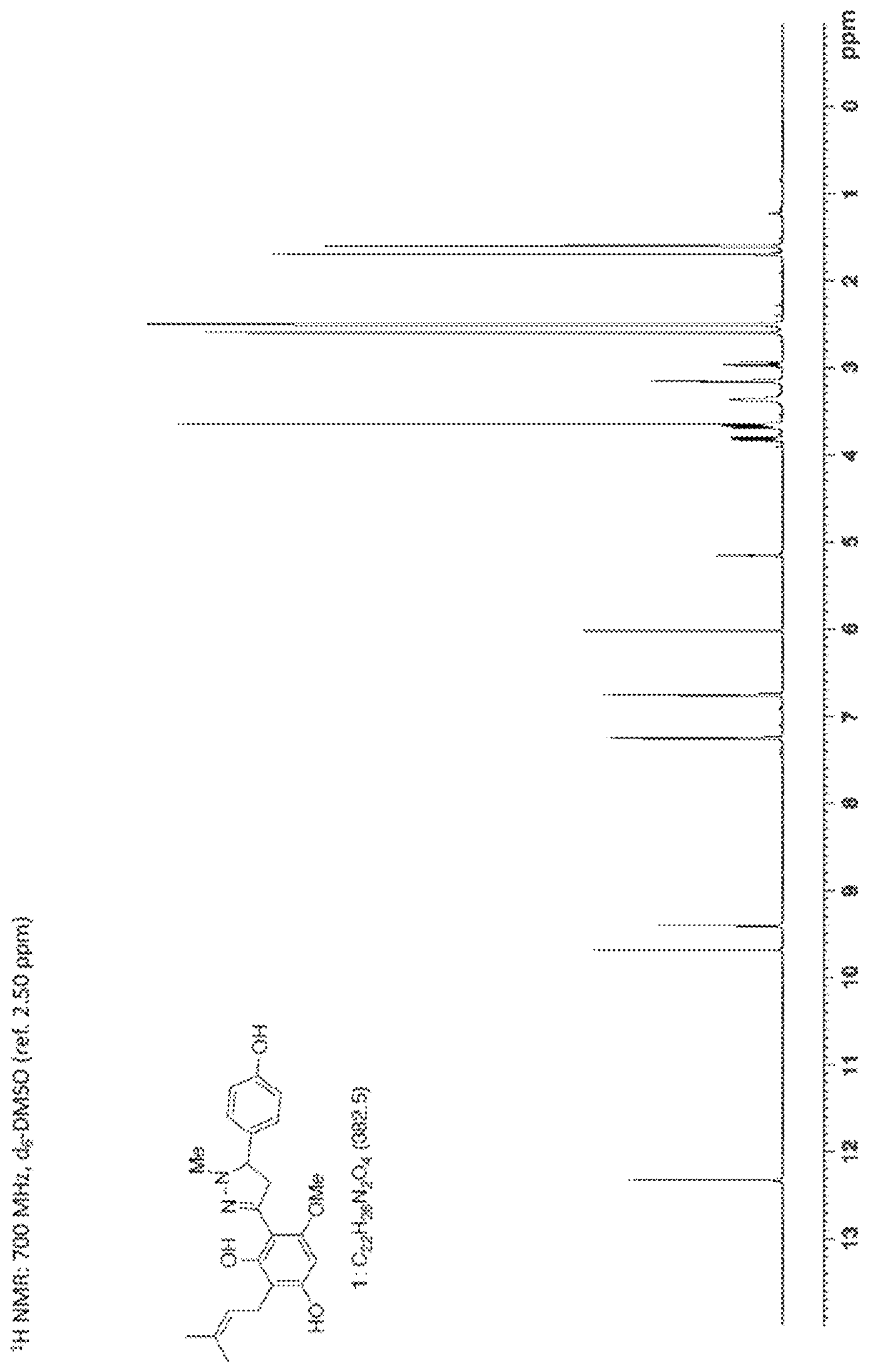
FIG. 1 is a $^{1}$H NMR spectrum for 4-(5-(4-hydroxyphenyl)-1-methyl-4,5-dihydro-1H-pyrazol-3-yl)-5-methoxy-2-(3-methylbut-2-en-1-yl)benzene-1,3-diol in $d_6$-DMSO.
Figure 2:
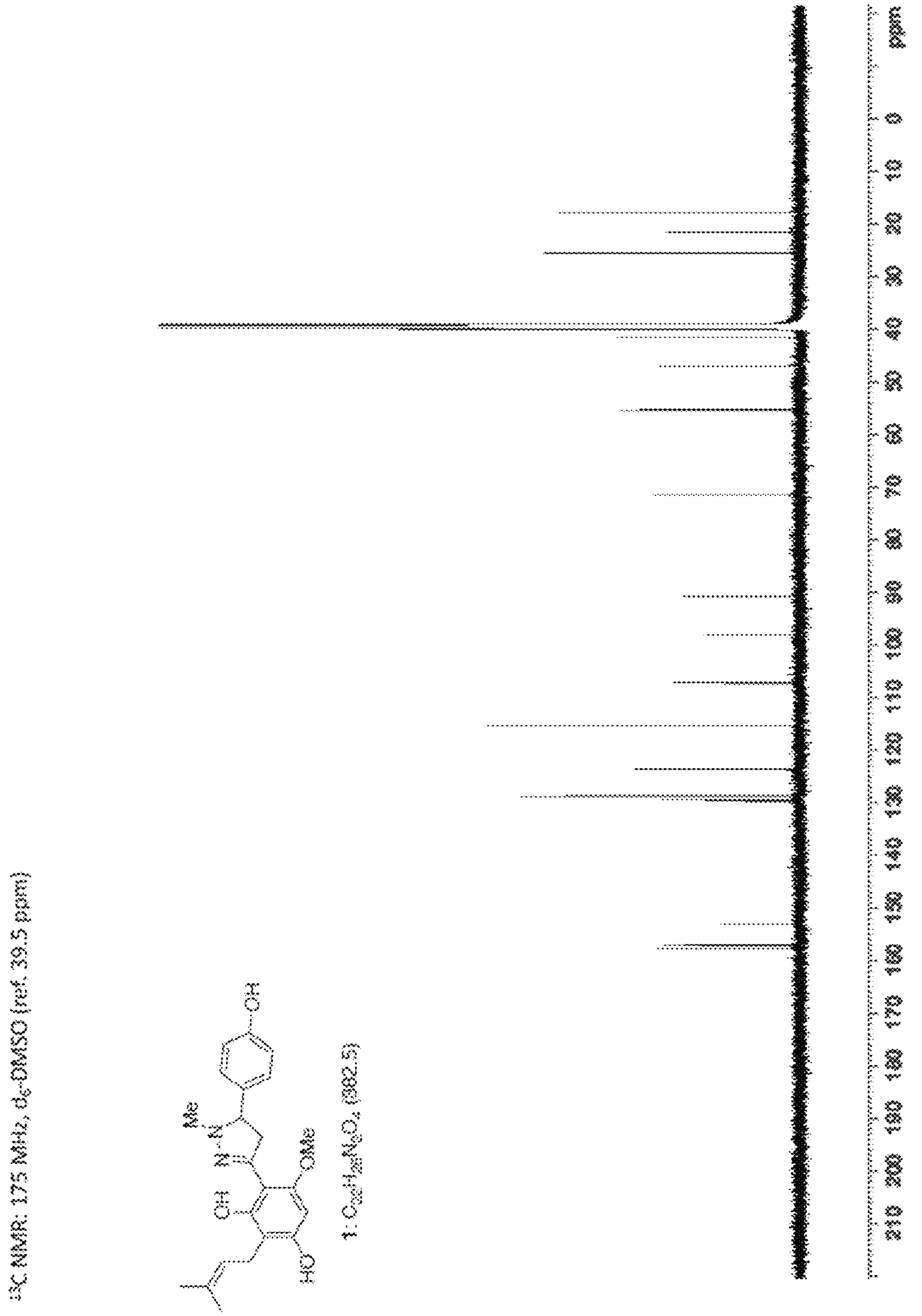
FIG. 2 is a $^{13}$C NMR spectrum for 4-(5-(4-hydroxyphenyl)-1-methyl-4,5-dihydro-1H-pyrazol-3-yl)-5-methoxy-2-(3-methylbut-2-en-1-yl)benzene-1,3-diol in $d_6$-DMSO.
Figure 3:
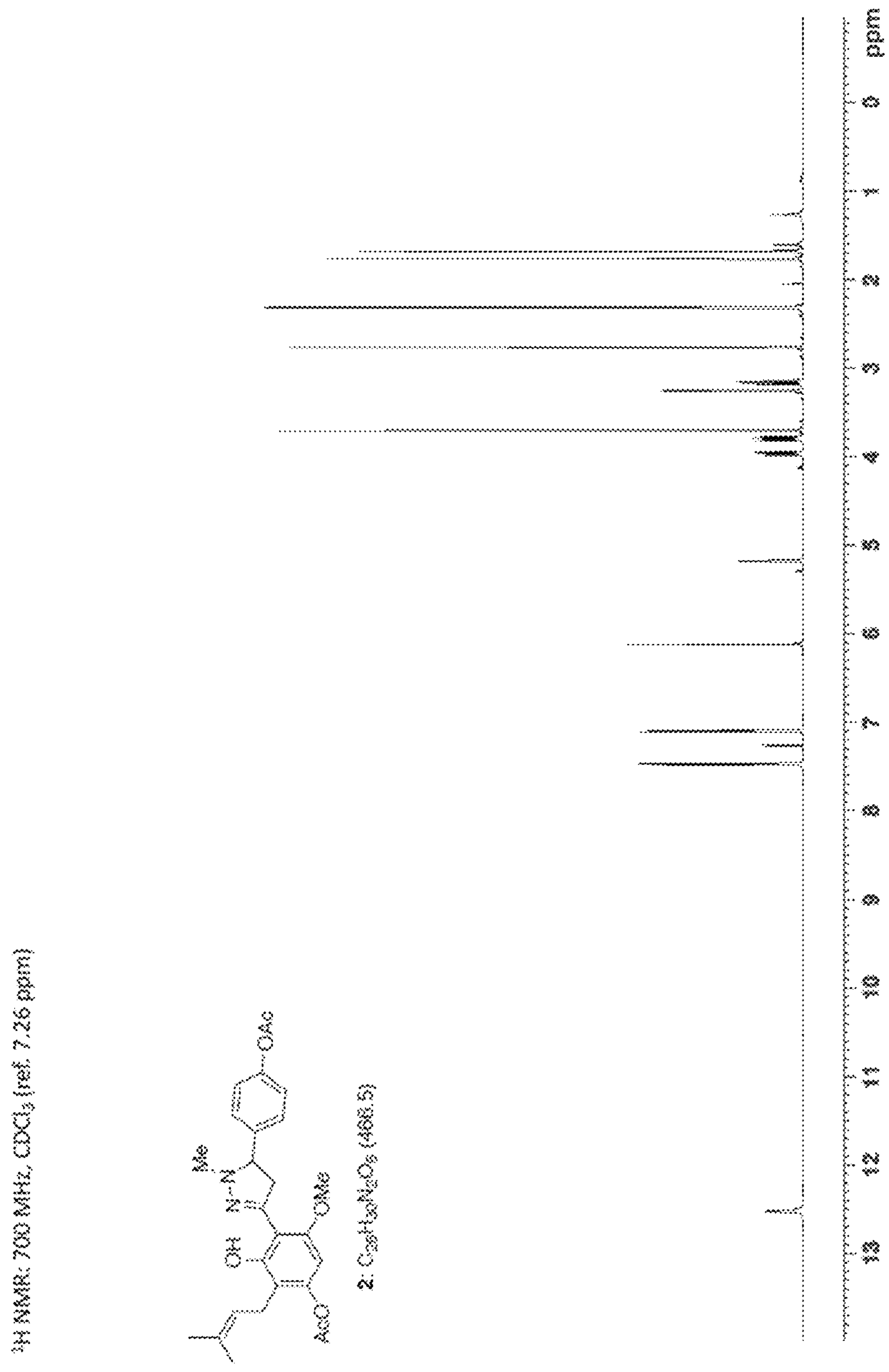
FIG. 3 is a $^{1}$H NMR spectrum for 4-(3-(4-acetoxy-2-hydroxy-6-methoxy-3-(3-methylbut-2-en-1-yl)phenyl)-1-methyl-4,5-dihydro-1H-pyrazol-5-yl)phenyl acetate in $CDCl_3$.
Figure 4:
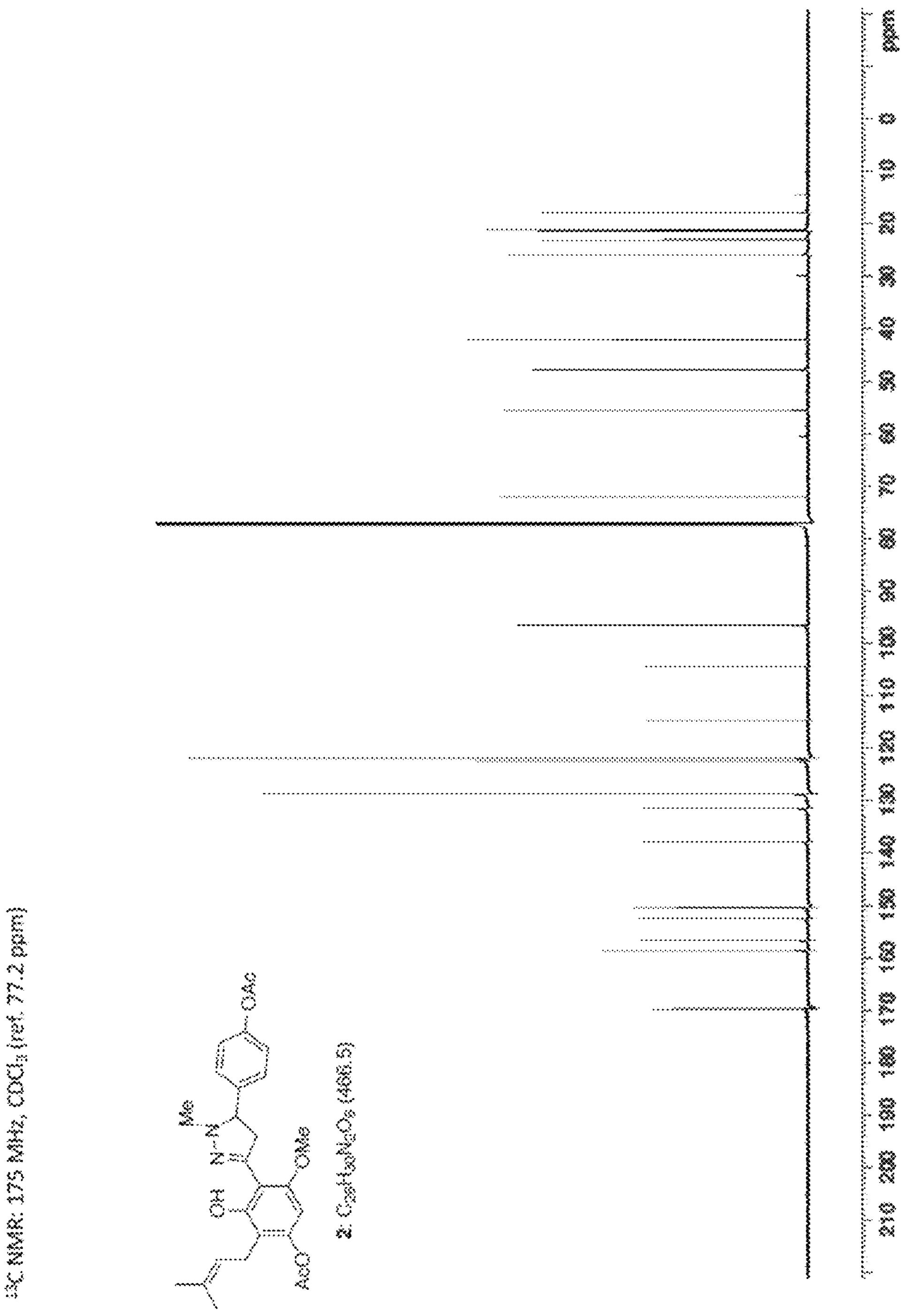
FIG. 4 is a $^{13}$C NMR spectrum for 4-(3-(4-acetoxy-2-hydroxy-6-methoxy-3-(3-methylbut-2-en-1-yl)phenyl)-1-methyl-4,5-dihydro-1H-pyrazol-5-yl)phenyl acetate in $CDCl_3$.
Figure 5:
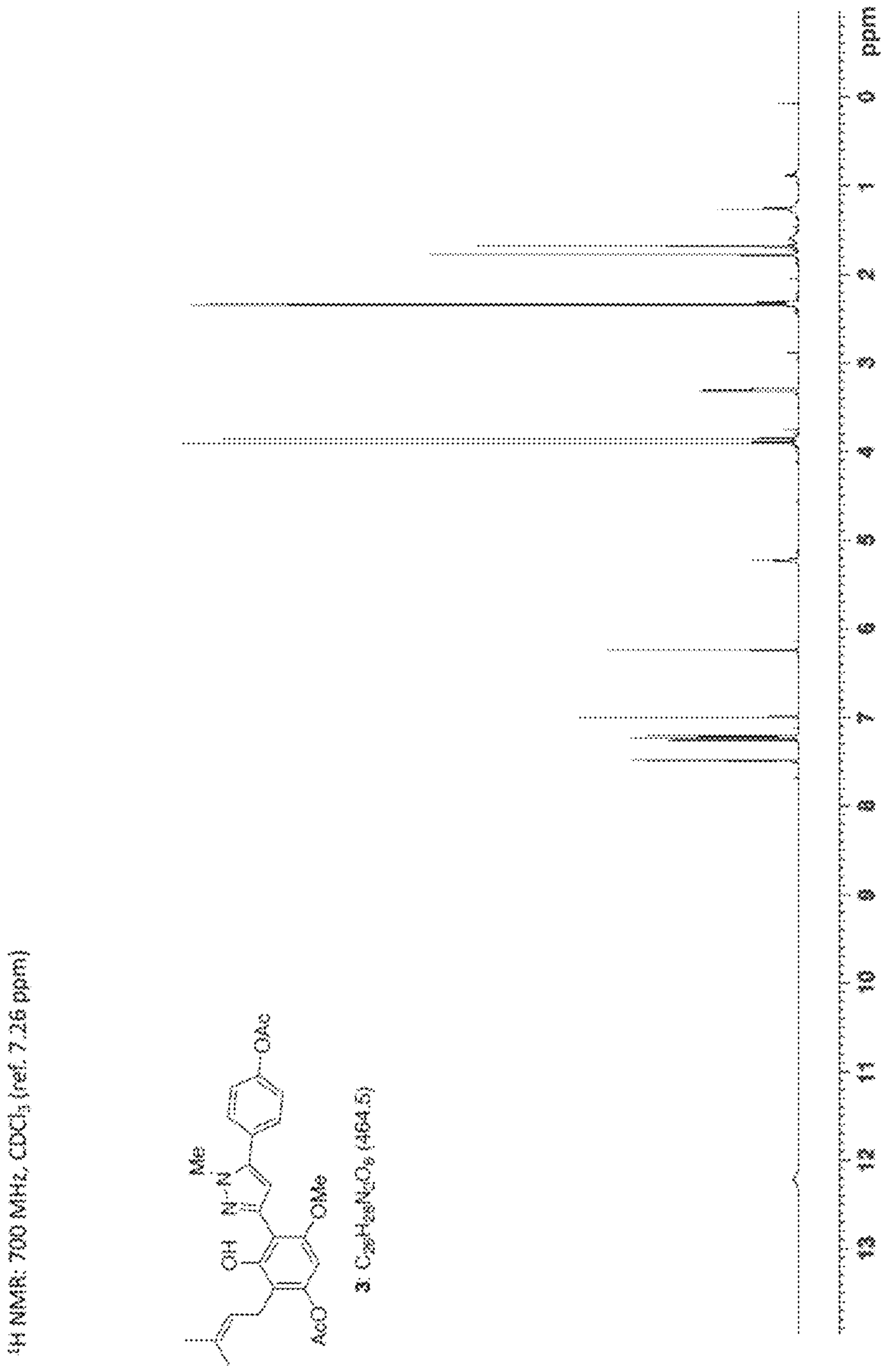
FIG. 5 is a $^{1}$H NMR spectrum for 4-(3-(4-acetoxy-2-hydroxy-6-methoxy-3-(3-methylbut-2-en-1-yl)phenyl)-1-methyl-1H-pyrazol-5-yl)phenyl acetate in $CDCl_3$.
Figure 6:
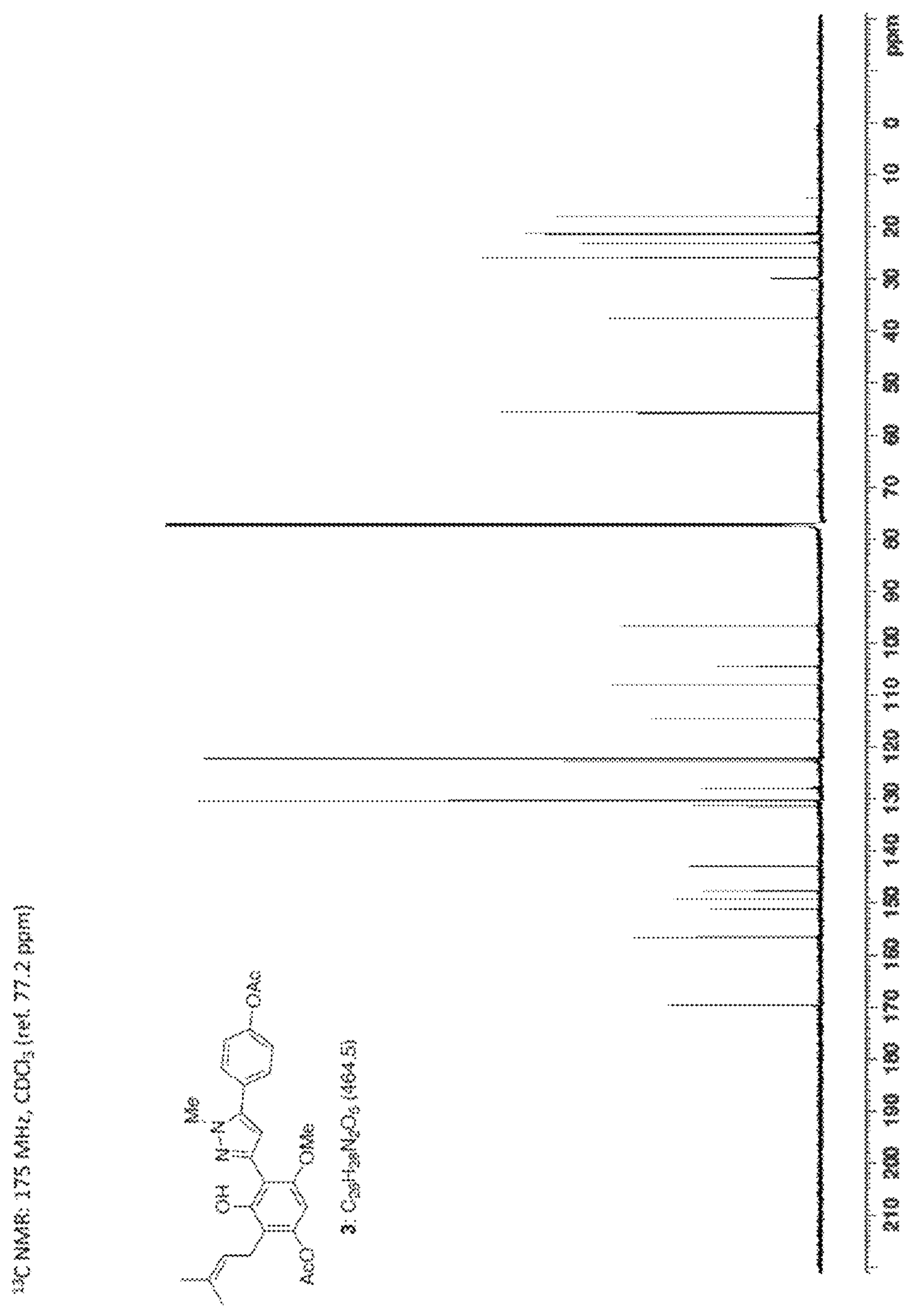
FIG. 6 is a $^{13}$C NMR spectrum for 4-(3-(4-acetoxy-2-hydroxy-6-methoxy-3-(3-methylbut-2-en-1-yl)phenyl)-1-methyl-1H-pyrazol-5-yl)phenyl acetate in $CDCl_3$.
Figure 7:
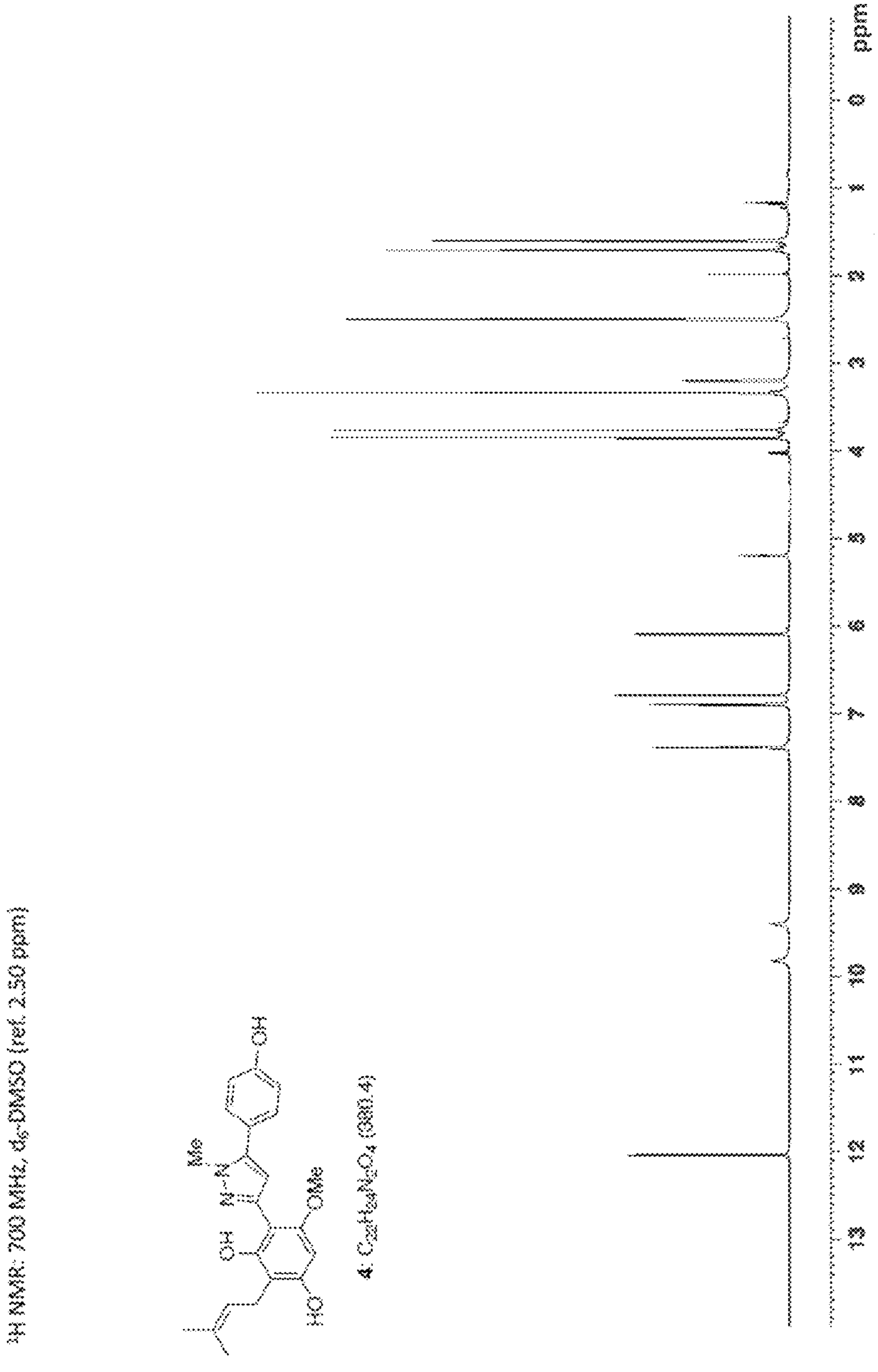
FIG. 7 is a $^{1}$H NMR spectrum for 4-(5-(4-hydroxyphenyl)-1-methyl-1H-pyrazol-3-yl)-5-methoxy-2-(3-methylbut-2-en-1-yl)benzene-1,3-diol in $d_6$-DMSO.
Figure 8:
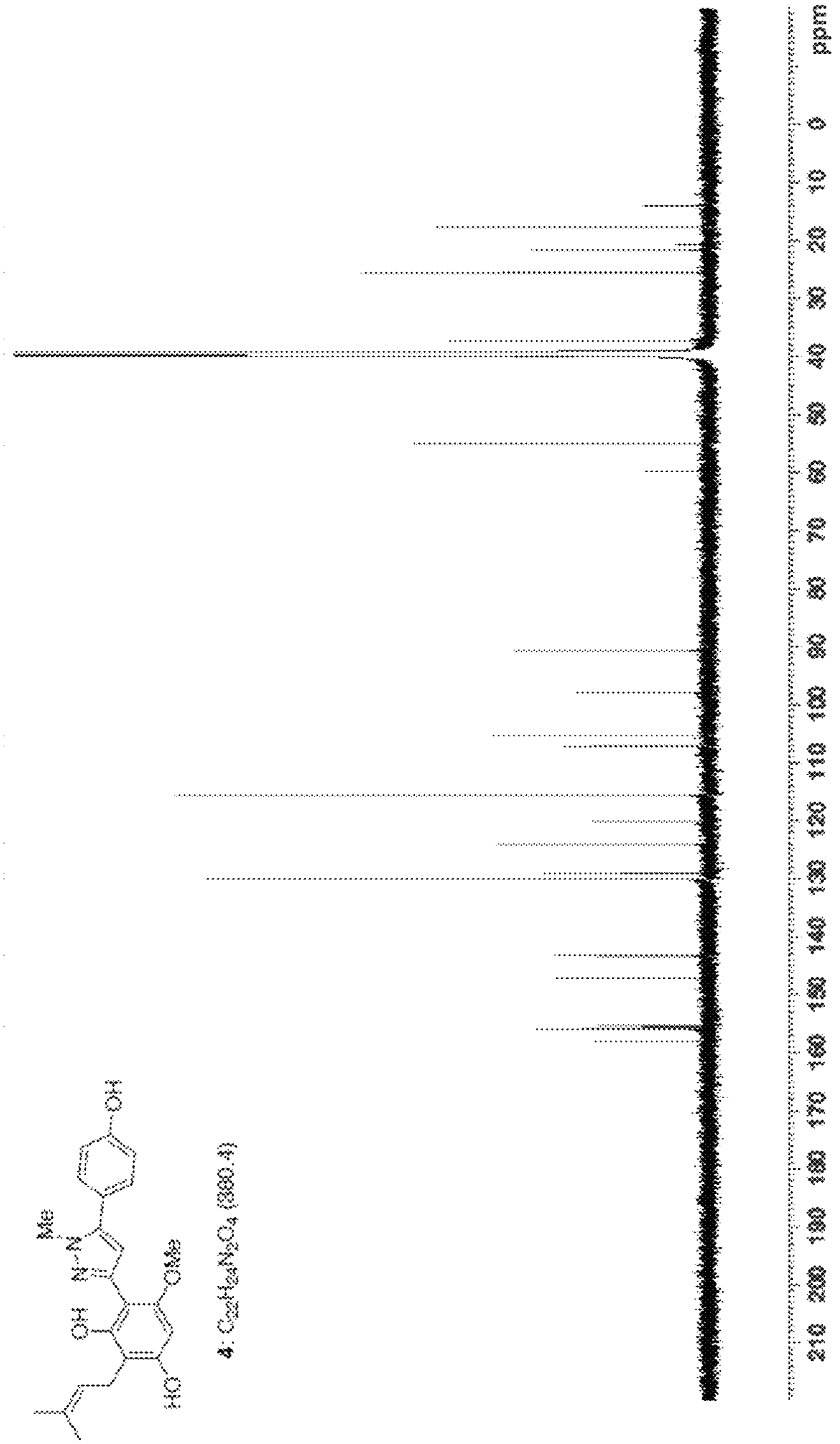
FIG. 8 is a $^{13}$C NMR spectrum for 4-(5-(4-hydroxyphenyl)-1-methyl-1H-pyrazol-3-yl)-5-methoxy-2-(3-methylbut-2-en-1-yl)benzene-1,3-diol in $d_6$-DMSO.
Figure 9:
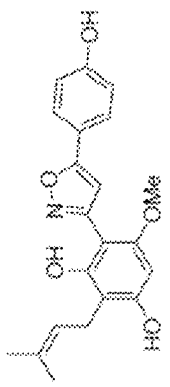
FIG. 9 is a $^{1}$H NMR spectrum for 4-(5-(4-hydroxyphenyl)isoxazol-3-yl)-5-methoxy-2-(3-methylbut-2-en-1-yl)benzene-1,3-diol in $d_6$-DMSO.
Figure 9:
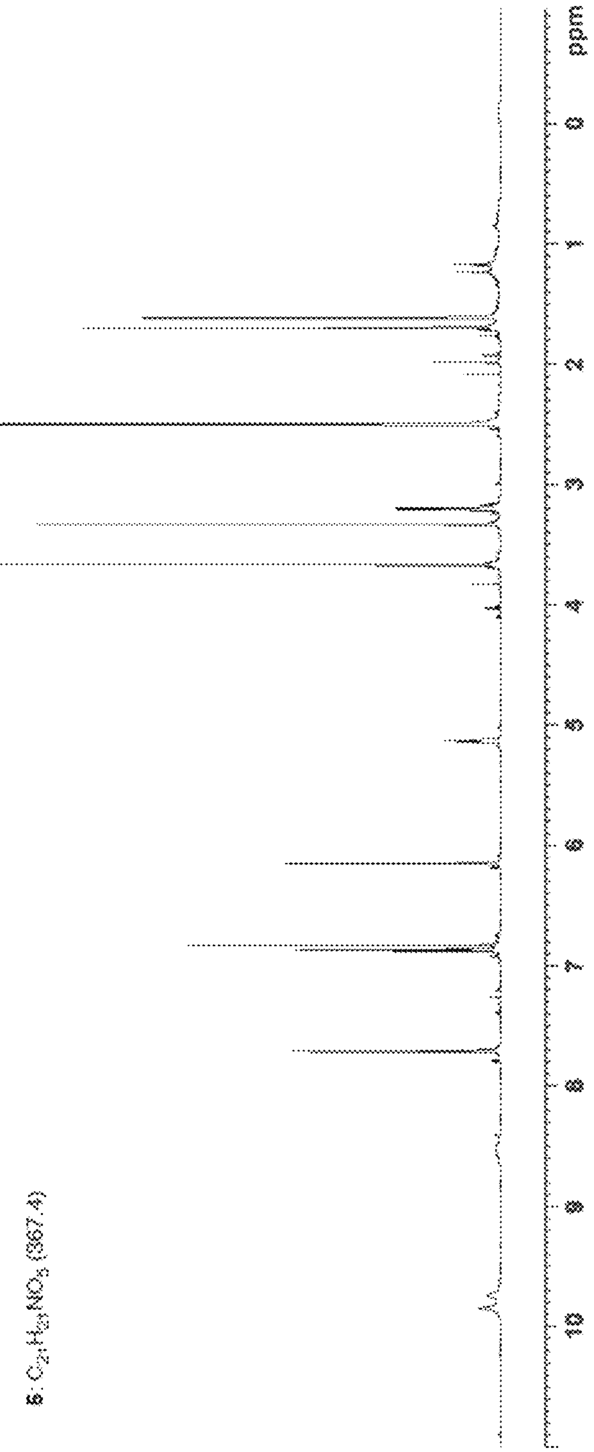
Figure 10:
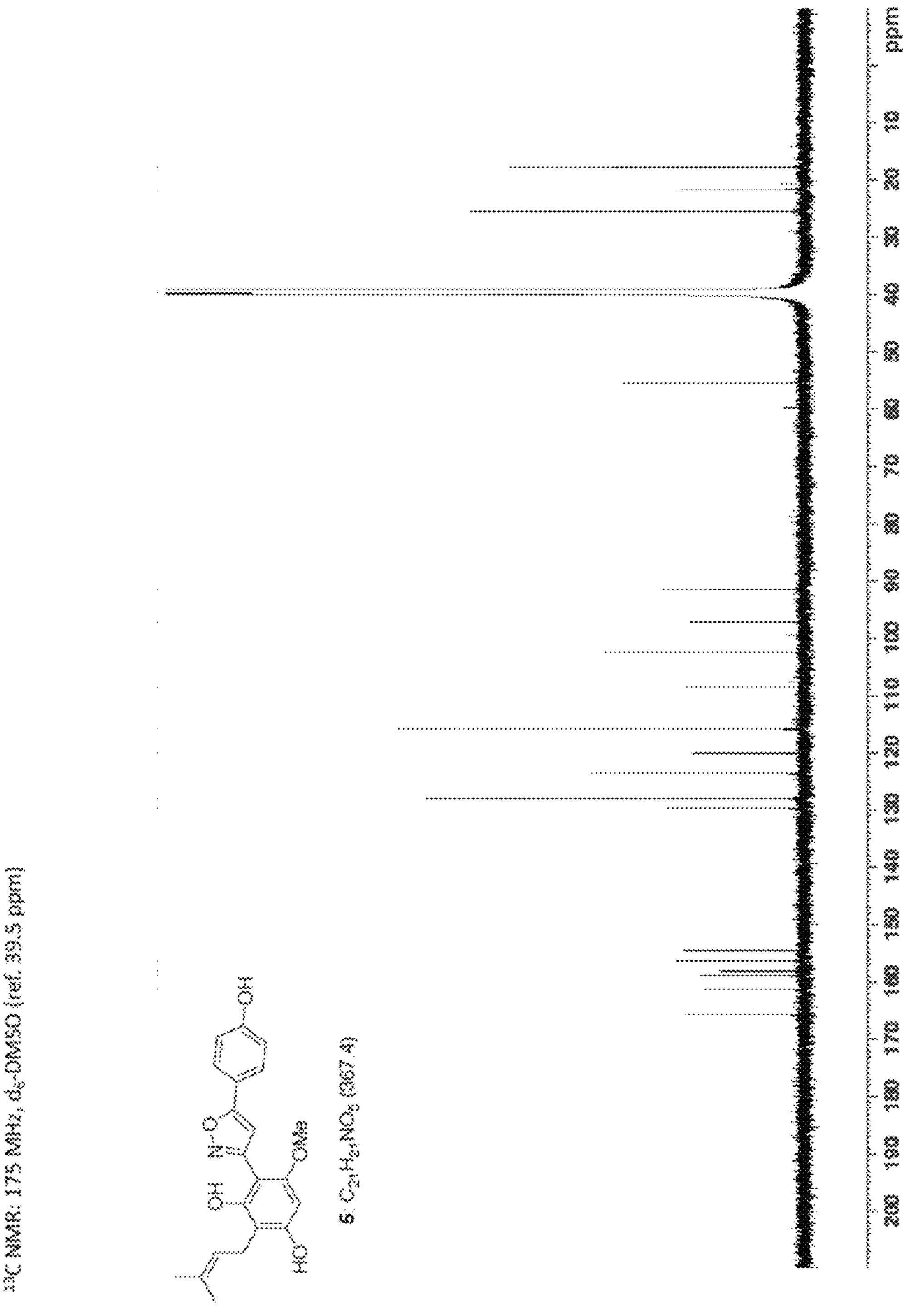
FIG. 10 is a $^{13}$C NMR spectrum for 4-(5-(4-hydroxyphenyl)isoxazol-3-yl)-5-methoxy-2-(3-methylbut-2-en-1-yl)benzene-1,3-diol in $d_6$-DMSO.

The following explanations of terms are provided to better describe the present disclosure and to guide those of ordinary skill in the art to make and use disclosed embodiments.

As used herein, "comprising" means "including."

The singular forms "a" or "an" or "the" include plural references unless the context clearly dictates otherwise.

The term "or" refers to a single element of stated alternative elements or a combination of two or more elements, unless the context clearly indicates otherwise.

Unless explained otherwise, all technical and scientific terms used herein have the same meaning as commonly understood by one of ordinary skill in the art to which this disclosure belongs. The compounds, methods, and examples are illustrative only and are not intended to be limiting, unless otherwise indicated.

Unless otherwise indicated, all numbers that are used in the specification or claims to express quantities of components, molecular weights, percentages, temperatures, times, etc., are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkanes (or alkynyl), including cyclic versions thereof, and further including straight- and branched-chain arrangements, and all stereo and positional isomers as well.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms, such as two to 25 carbon atoms, or 2 to 10 carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cylcoalkenyl), cis, or trans (e.g., E or Z).

Aryl: An aromatic carbocyclic group comprising at least five carbon atoms to carbon atoms, such as five to ten carbon atoms, having a single ring or multiple condensed rings, which condensed rings can or may not be aromatic provided that the point of attachment is through an atom of the aromatic carbocyclic group.

Derivative: A compound that is derived from a parent compound (e.g., a structurally similar compound), has functional groups or components that are present in a parent compound, or that can be imagined to arise from another compound, for example, if one atom or functional group is replaced with another atom, group of atoms, or another functional group.

Heteroaryl: An aryl group comprising at least one heteroatom to six heteroatoms within the ring, such as one to four heteroatoms in the ring, where the heteroatom can be selected from, but is not limited to, oxygen, nitrogen, sulfur, selenium, phosphorous, and oxidized forms thereof, and combinations thereof. Such heteroaryl groups can have a single ring or multiple condensed rings, wherein the condensed rings may or may not be aromatic and/or contain a heteroatom, provided that the point of attachment is through an atom of the aromatic heteroaryl group.

Mitochondrial Uncoupler: A compound that can allow protons to reenter a mitochondrial matrix and bypass ATP synthase, partially dissipating the electrochemical gradient established by the electron transport chain. Mitochondrial uncoupling alters the normal functioning of the electron transport chain and ATP synthase in the mitochondria. Additional reducing equivalents such as NADH and FADH2 are then needed to reestablish the proton gradient, resulting in higher energy expenditure and additional heat generation as the activity of electron transport chain proteins is increased and additional oxygen is reduced to water. Changes in cellular oxidative phosphorylation rates can therefore be estimated by the rate of oxygen consumption over time.

Prodrug: Prodrugs include compounds disclosed herein that comprise at least one progroup, also referred to as a promoiety. Prodrugs may be active in their prodrug form, or may be inactive until converted under physiological or other conditions to an active drug form. In some embodiments, one or more functional groups of the compounds disclosed herein are used to attach progroups that can be released from the compound such as through hydrolysis, enzymatic cleavage or some other cleavage mechanism, to yield the functional groups originally present on the compound prior to adding the progroup. Solely by way of example, hydroxyl groups may be reacted with another compound to form an ester, ether, phosphate, phosphonate, sulfonate, or sulfonyl progroup that cleaves under conditions of use to re-generate the hydroxyl group.

Subject: This term refers to any mammal, such as humans, and non-human mammals (e.g., domestic animals, non-domestic animals, companion animals, zoo animals, and farm animals).

A person of ordinary skill in the art will recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless affirmatively stated otherwise.

II. Compounds

Disclosed herein are representative embodiments of xanthohumol derivatives, and more particularly xanthohumol derivatives comprising a cyclic component, such as a pyrazole or isoxazole, that replaces the α,β-unsaturated carbonyl functional group

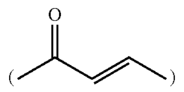

of xanthohumol. Disclosed xanthohumol derivatives are useful for treating various maladies, including metabolic syndrome, or risk factors associated with metabolic syndrome, such as obesity, diabetes, and/or cardiovascular disease. The compounds also can act as mitochondrial uncouplers.

In some embodiments, the compounds have structures satisfying Formula I

Formula I

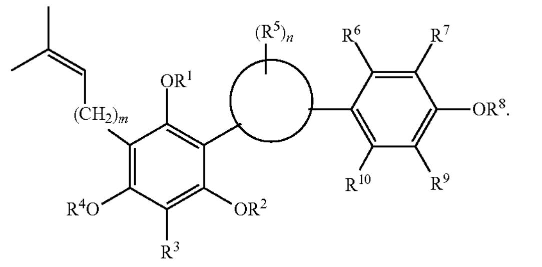

With reference to Formula I, m is 1-10, more typically 2-5, preferably 1, 2 or 3, with certain representative embodiments having m=1; n=0 for an unsubstituted ring and n has a maximum value equal to the total number of ring positions available for substitution, such as ring substitution with 1, 2 or 3 substituents, with certain representative embodiments having n=1; $R^1$-$R^4$ and $R^6$-$R^{10}$ are independently selected from H, $C_1$-$C_{10}$ alkyl, a protecting group or a promoiety; $R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl; $R^1$-$R^{10}$ are more typically selected from H, $C_1$-$C_6$ alkyl, even more typically $C_1$-$C_3$ alkyl, with $R^1$-$R^{10}$ preferably being selected from H and methyl, with certain representative embodiments having $R^1$, $R^3$, $R^4$ and $R^{6-10}$=hydrogen and $R^2$ and $R^5$=methyl; and the circle represents a cyclic structure, typically a cyclic structure, such as a heterocyclic or heteroaryl structure, having 4 to 6 ring atoms and at least one nitrogen atom, at least one oxygen atom, at least one sulfur atom, or combinations thereof. Currently preferred compounds comprise 5-membered cyclic structures, including pyrrolidines—

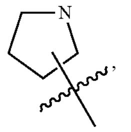

pyrroles—

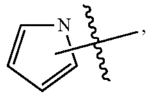

pyrazoles—

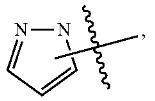

imidazoles—

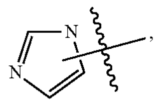

tetrahydrofurans—

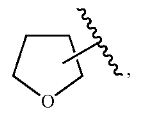

furans—

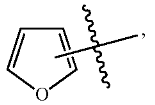

thiolane—

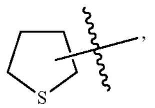

thiophene—

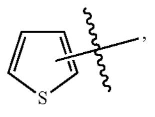

, oxazole—

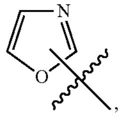

, isoxazoles—

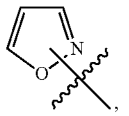

, and thiazoles—

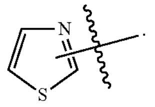

.

The bond with the wavy line indicates that the attachment of the cyclic structure to other portions of the molecule can be at any position available for bonding. A person of ordinary skill in the art will appreciate that such compounds may have two such "floating" bonds as the cyclic structure is located in a central portion of the derivatives and is coupled to two groups.

Certain disclosed embodiments of the present invention have a Formula II

Formula II

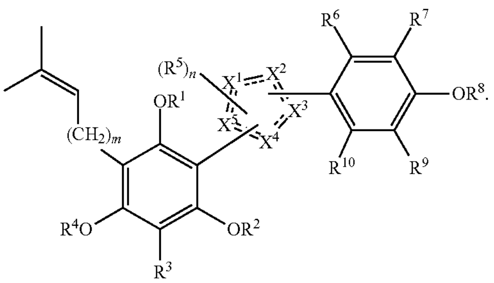

With reference to Formula II, m is 1-10, more typically 2-5, and m preferably is 1, 2 or 3, with certain representative embodiments having m=1; n=0 for an unsubstituted ring and n has a maximum value equal to the total number of ring positions available for substitution, such as ring substitution with 1, 2 or 3 substituents, with certain representative embodiments having n=1; $R^1$-$R^4$ and $R^6$-$R^{10}$ are independently selected from H, $C_1$-$C_{10}$ alkyl, a protecting group or a promoiety; $R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl; $R^1$-$R^{10}$ are more typically selected from H, $C_1$-$C_6$ alkyl, even more typically $C_1$-$C_3$ alkyl, with $R^1$-$R^{10}$ preferably being selected from H and methyl, with certain representative embodiments having $R^1$, $R^3$, $R^4$ and $R^{6-10}$=hydrogen and $R^2$ and $R^5$=methyl; and X is independently C, N, O, S, or combinations thereof. Formula II depicts bonds that are not directly coupled to an atom to indicate that such substituents may be coupled to any acceptable bonding position. One representative embodiment has $R^1$, $R^3$, $R^4$ and $R^{6-10}$=hydrogen; $R^2$ and $R^5$=methyl; and X=N, such as with pyrazole derivatives,

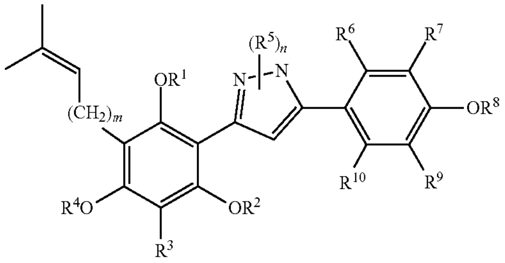

or oxygen and nitrogen for isoxazole derivatives,

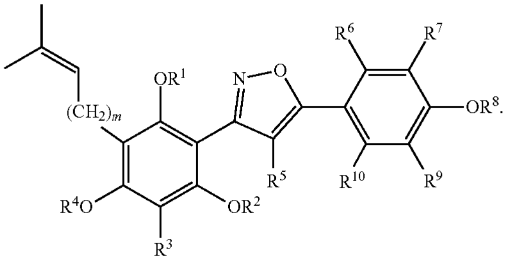

Yet additional pyrazole embodiments of the present disclosure may have a Formula III, as below.

Formula III

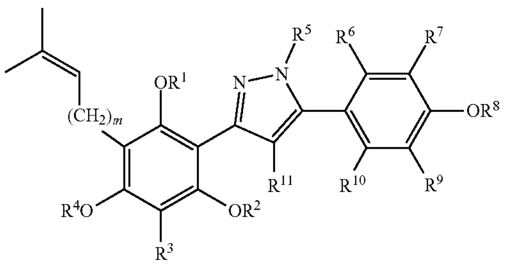

With reference to Formula III, m is 1-10, more typically 2-5, and preferably 1, 2 or 3, with one representative embodiment having m=1; $R^1$-$R^4$ and $R^6$-$R^{11}$ are independently selected from H, $C_1$-$C_{10}$ alkyl, a protecting group or a promoiety; $R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl; $R^1$-$R^{11}$ are more typically selected from H, $C_1$-$C_6$ alkyl, even more typically $C_1$-$C_3$ alkyl, with $R^1$-$R^{11}$ preferably being selected from H and methyl, with certain representative embodiments having $R^1$, $R^3$, $R^4$ and $R^{6-11}$=hydrogen and $R^2$ and $R^5$=methyl. Currently preferred pyrazole compounds have a Formula IV, below, where the substituents are as defined above.

Formula IV

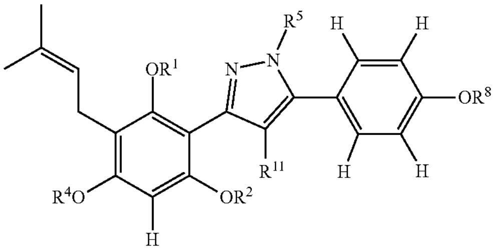

Particular representative compounds according to the present invention include XP

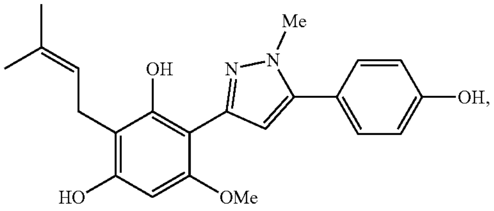 [SMILES: COc1cc(O)c(CC=C(C)C)c(O)c1-c1cc(-c2ccc(O)cc2)n(C)n1]

4-(5-(4-hydroxyphenyl)-1-methyl-1H-pyrazol-3-yl)-5-methoxy-2-(3-methylbut-2-en-1-yl)benzene-1,3-diol, and

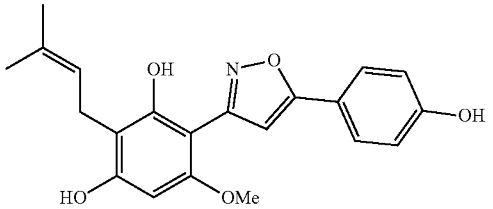 [SMILES: COc1cc(O)c(CC=C(C)C)c(O)c1-c1cc(-c2ccc(O)cc2)on1]

4-(5-(4-hydroxyphenyl)isoxazol-3-yl)-5-methoxy-2-(3-methylbut-2-en-1-yl)benzene-1,3-diol.

III. Compound Synthesis

A person of ordinary skill in the art will appreciate that compounds within the scope of the present invention can be made synthetically or semi-synthetically by any number of suitable routes. The following discussion should not be considered to limit the present invention to the particular features of the disclosed synthetic schemes. Instead, these schemes are intended solely to illustrate one suitable synthetic method. Additional information concerning the depicted compounds and synthetic procedures can be found in Examples 1-5 and FIGS. 1-10.

Scheme 1 below provides a synthetic protocol that was used to synthesize 4-(5-(4-hydroxyphenyl)-1-methyl-1H-pyrazol-3-yl)-5-methoxy-2-(3-methylbut-2-en-1-yl)benzene-1,3-diol. The particular embodiment of Scheme 1 starts with the known, naturally occurring xanthohumol.

Scheme 1

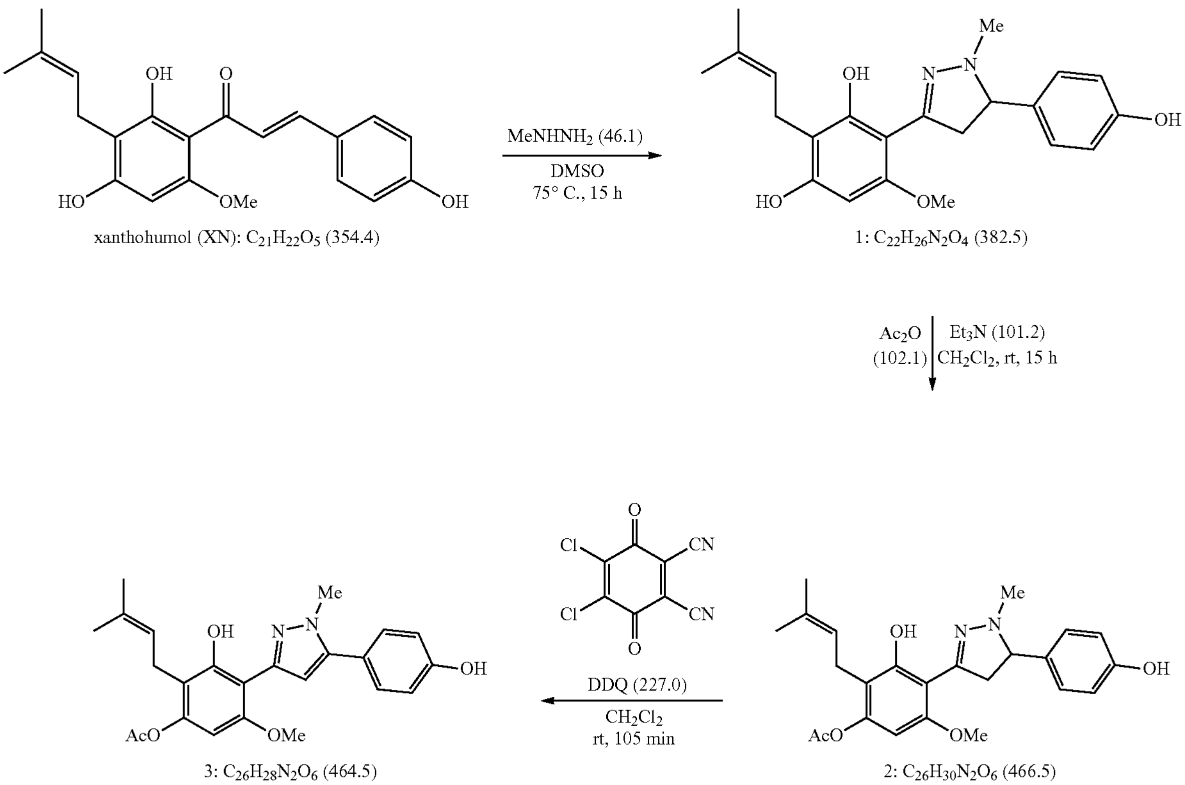

-continued

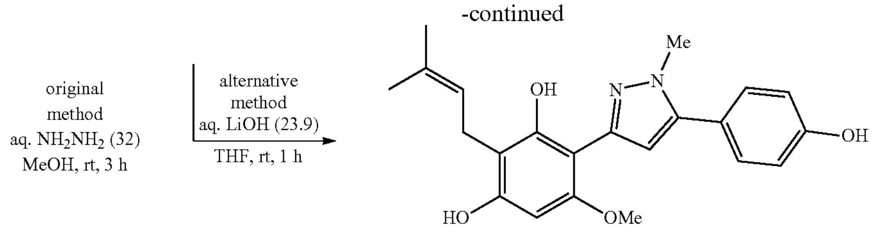

4

XN Me pyrazol (10): $C_{22}H_{24}N_2O_4$ (380.4)

With reference to Scheme 1, xanthohumol undergoes Michael addition with methylhydrazine ($MeNHNH_2$) in DMSO at 75° C. for 15 hours to form pyrazoline compound 1 in 77% yield. A person of ordinary skill in the art will appreciate that other hydrazine-based reagents can be used to provide ring substituents following Michael addition other than methyl. Accordingly, the methylhydrazine reagent can be represented as $R^5NHNH_2$, where $R^5$ refers to the generic formulas discussed above. That is, $R^5NHNH_2$ can be any compound where $R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl. $C_1$-$C_{10}$ alkyl is more typically $C_1$-$C_6$ alkyl, such as methyl, ethyl, propyl, butyl, pentyl and hexyl, including all structural and stereo isomers thereof. Cycloalkyl derivatives include cyclopropyl, cyclobutyl, cyclopentyl, cyclohexyl, and such rings may also include one or more heteroatoms selected from O, N and S. Aryl derivatives include phenyl and substituted phenyl, such as toluyl. Heteroaryl derivatives can be 5-, 6- or 7-membered rings comprising at least one heteroatom, selected from O, N and S, such as pyridinyl and pyrimidinyl.

Compound 1 includes several free hydroxyl groups that must be protected prior to the subsequent oxidation step that produces compound 3. As a result, compound 1 was treated with acetic anhydride and triethyl amine in methylene chloride at room temperature to produce diacetate-protected compound 2.

Compound 2 was then converted to pyrazole derivative 3 in a 56% yield by reaction with DDQ at room temperature for 105 minutes. The acetate protecting groups were then removed from compound 3 to produce 4-(5-(4-hydroxyphenyl)-1-methyl-1H-pyrazol-3-yl)-5-methoxy-2-(3-methylbut-2-en-1-yl)benzene-1,3-diol, compound 4. Deprotection can be accomplished in any of a number of ways. For example, compound 3 can be treated with aqueous hydrazine in methanol at room temperature for 3 hours. Alternatively, the acetate protecting groups can be removed using aqueous lithium hydroxide in tetrahydrofuran at room temperature for about 1 hour.

As discussed above, ring structures other than pyrazoles also are derivatives within the scope of the present invention. For example, isoxazoles can be made as indicated below by Scheme 2.

Scheme 2

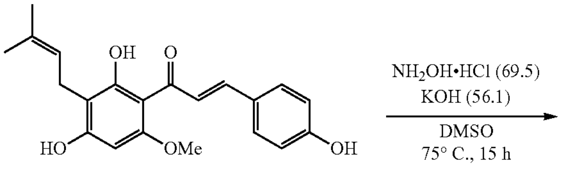

xanthohumol (XN): $C_{21}H_{22}O_5$ (354.4)

-continued

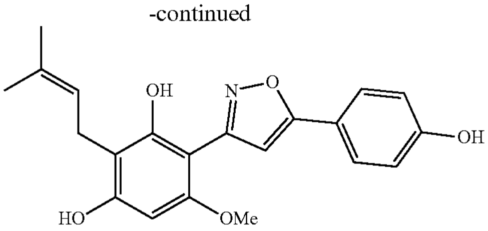

xanthohumol isoxazole (5): $C_{21}H_{21}No_5$ (367.4)

For this reaction, xanthohumol was reacted with hydroxylamine hydrochloride and potassium hydroxide in DMSO at 75° C. for 15 hours to form isoxazole derivative 5.

IV. Compositions Comprising Disclosed Compounds

Also disclosed herein are embodiments of compositions (e.g., pharmaceutical compositions) useful for treating, preventing, or ameliorating maladies, such as metabolic syndrome, or risk factors associated with metabolic syndrome, such as obesity, diabetes, and/or cardiovascular disease. In particular disclosed embodiments, the compositions are formulated for administration as a dietary supplement. The compositions can comprise one or more compounds satisfying formulas disclosed above. In particular disclosed embodiments, the compositions can comprise one or more mitochondrial uncoupler compounds satisfying any of the formulas disclosed above. In some embodiments, the compositions can further comprise one or more pharmacologically active agents, xanthohumol, pharmaceutically acceptable excipients, vitamins (e.g., vitamin C, vitamin D, or the like), herbal or botanical products or their extracts (e.g., turmeric, curcumin, resveratrol, grape seed extract, or the like), amino acids, metabolites (e.g., XN—O-glucuronides), extracts (e.g., hop extracts, Ashitaba (*Angelica keiskei*) extracts, licorice, bitter melon (*Mormordica charantia*) extracts, or the like), other ingredients, and any and all combinations thereof. Examples of pharmacologically active compounds that can be used in combination with disclosed compounds include statins, such as atorvastatin and simvastatin.

Exemplary pharmaceutically acceptable excipients can include, but are not limited to, binding agents (e.g., starch, polyvinylpyrrolidone, hydroxypropyl methylcellulose, and the like), fillers (e.g., lactose, cellulose, calcium hydrogen phosphate, and the like), lubricants (e.g., talc, silica, stearates, and the like), emulsifiers/solubilizers (e.g., lecithin; polysorbates; alkylene polyols, such as propylene glycol; or fatty acids, such as long-chain fatty acids with aliphatic chains of at least 13 carbon atoms, medium-chain fatty acids with aliphatic chains of between 6 and 12 carbon atoms, and short-chain fatty acids with aliphatic chains of between 2 and 5 carbon atoms), or combinations thereof. Exemplary polysorbates include, but are not limited to, polysorbate 80, polysorbate 60, polysorbate 40, polysorbate 20, or combinations thereof. Exemplary fatty acids include, but are not limited to myristoleic acid, palmitoleic acid, sapienic acid, oleic acid, elaidic acid, vaccenic acid, linoleic acid, arachidonic acid, eicosapentaenoic acid, or combinations thereof. In particular disclosed embodiments, the pharmaceutically acceptable excipient can be selected from oleic acid, propylene glycol, polysorbate 80, and combinations thereof.

In particular disclosed embodiments, the composition may be formulated as a dietary supplement. The term “dietary supplement” in this context concerns a composition comprising an ingestible compound that includes one or more compounds satisfying any of the formulas described herein, or any composition thereof, that provides nutrients (e.g., amino acids, phytochemicals) consumable by a subject for promoting good health, for protective benefits, or to maintain a normal, healthy lifestyle (such as by preventing, ameliorating or eliminating disease) as compared to a subject who does not receive the dietary supplement. In exemplary embodiments, the compositions and dietary supplements disclosed herein can comprise 4-(5(4-hydroxyphenyl)-1-methyl-1H-pyrazol-3-yl)-5-methoxy-2-(3-methylbut-2-en-1-yl)benzene-1,3-diol, 4-(5-(4-hydroxyphenyl)isoxazol-3-yl)-5-methoxy-2-(3-methylbut-2-en-1-yl)benzene-1,3-diol, or combinations thereof. One or more of these compounds can also be used in combination with xanthohumol, α,β-dihydroxanthohumol, tetrahydroxanthohumol, isoxanthohumol, or derivatives thereof (e.g., prodrugs). In some embodiments, the dietary supplement can further comprise one or more of the pharmaceutically acceptable excipients disclosed herein.

Compounds according to the present invention, or compositions comprising such compounds, can be formulated as a dietary supplement for administration using any suitable administration route, such as oral, nasal, injection, topical, transdermal, or in a form suitable for administration by inhalation or insufflation. In particular disclosed embodiments, the compounds (or compositions thereof) are formulated for oral administration. In some embodiments, the compounds (or compositions thereof) are formulated for oral administration by combining at least one compound disclosed herein with one or more pharmaceutically acceptable excipients to form a pharmaceutical composition that is then further formulated into capsules, lozenges, or tablets that are made of, or contain, the pharmaceutical composition. In yet other embodiments, the compound(s) need not be combined with a pharmaceutically acceptable excipient and can instead be administered neat. The pharmaceutical compositions, such as capsules, lozenges, or tablets, can be coated with films, enteric coatings, sugars, or the like.

In some embodiments, the compounds (and compositions thereof) can be formulated for oral administration by combining at least one compound disclosed herein with one or more pharmaceutically acceptable excipients and an aqueous or non-aqueous delivery medium. Such formulations can be liquid preparations that can take the form of elixirs, solutions, syrups, suspensions, or the like. In some embodiments, the compound (or composition thereof) can be provided as a dry component that can be mixed with an aqueous or non-aqueous delivery medium during administration. Such liquid formulations can further comprise buffer salts, preservatives, flavoring, or coloring.

In some embodiments, the compound (or composition thereof) can be formulated for delayed or controlled compound release. For example, the compound can be a prodrug that comprises a progroup that is released (e.g., by metabolic cleavage, hydrolytic cleavage, enzymatic cleavage, or the like) from the compound after administration.

In particular disclosed embodiments, compositions are formulated to provide a therapeutically acceptable amount of the compound or the compounds. A person of ordinary skill in the art will understand how to determine a therapeutically acceptable amount. For certain embodiments, however, a therapeutically acceptable amount of the compound comprises an amount ranging from greater than 0 mg to 1,000 mg of the compound, such as 5 mg to 500 mg, or 10 mg to 250 mg, or 20 mg to 200 mg, or 50 mg to 150 mg, administered once or twice daily. In particular disclosed embodiments, the compositions comprise a therapeutically effective amount of the compound ranging from 60 mg to 240 mg, or from 45 mg to 180 mg, or from 20 mg to 80 mg, or from 80 g to 320 mg, administered once or twice daily. In yet additional embodiments, the compositions can be formulated to deliver 0.1 mg/day to 500 mg/day of active compound according to the present invention, such as 20 mg/day to 280 mg/day, or 60 mg/day to 240 mg/day, to the subject to which it is administered.

In some embodiments, the pharmaceutically acceptable excipients are selected from a fatty acid, an alkylene glycol, and a polysorbate. In some embodiments, the amount of the pharmaceutically excipient can range from greater than 0% to 99% by weight, such as 5% by weight to 90% by weight, or 10% by weight to 80% by weight, or 25% by weight to 45% by weight, or 30% by weight to 35% by weight. In some embodiments, the total volume of the pharmaceutical composition can range from greater than 0 mL to 35 mL per dosage form, such as 0.1 mL to 30 mL per dosage form, or 0.1 mL to 28 mL per dosage form, or 0.6 mL to 1 mL. In exemplary embodiments wherein the pharmaceutical composition is administered via a capsule to a human subject, the volume of the composition that is administered may range from 0.1 mL to 2 mL. In some embodiments wherein the composition is formulated for veterinary use, the composition can be administered in amounts ranging from 0.1 mL to 30 mL, such as 1.0 mL to 25 mL. In some embodiments, animal doses can be derived from the doses described herein by using the FDA formula for allometric interspecies scaling of dose. Such formulas are described in “Guidance for Industry Estimating the Maximum Safe Starting Dose in Initial Clinical Trials for Therapeutics in Adult Healthy Volunteers,” U.S. Department of Health and Human Services, Food and Drug Administration, and Center for Drug Evaluation and Research, July 2005, http://www.fda.gov/cder/guidance/index.htm, which is incorporated herein by reference.

V. Biological Materials, Methods and Data

The materials and methods used to obtain and analyze disclosed biological information are discussed below in Example 6.

Figure 11A:
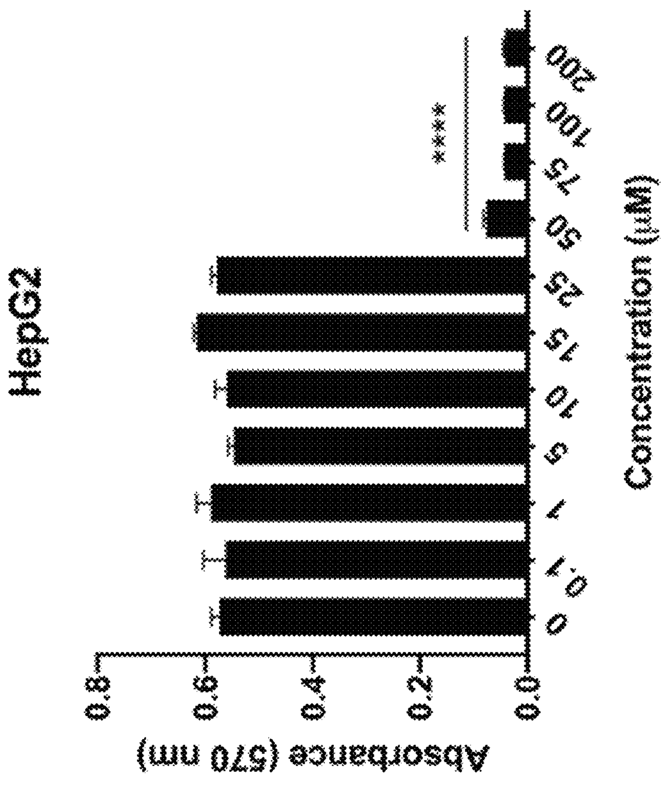
FIGS. 11A-11C are graphs of absorbance (570 nm) versus concentration (μM) providing data establishing that exposure of cells to 4-(5-(4-hydroxyphenyl)-1-methyl-1H-pyrazol-3-yl)-5-methoxy-2-(3-methylbut-2-en-1-yl)benzene-1,3-diol did not affect cell viability for concentrations up to 25 μM in (A) HepG2 and (B) C2C12 cells, and up to 5 μM in (C) 3T3L1 cells.
Figure 11B:
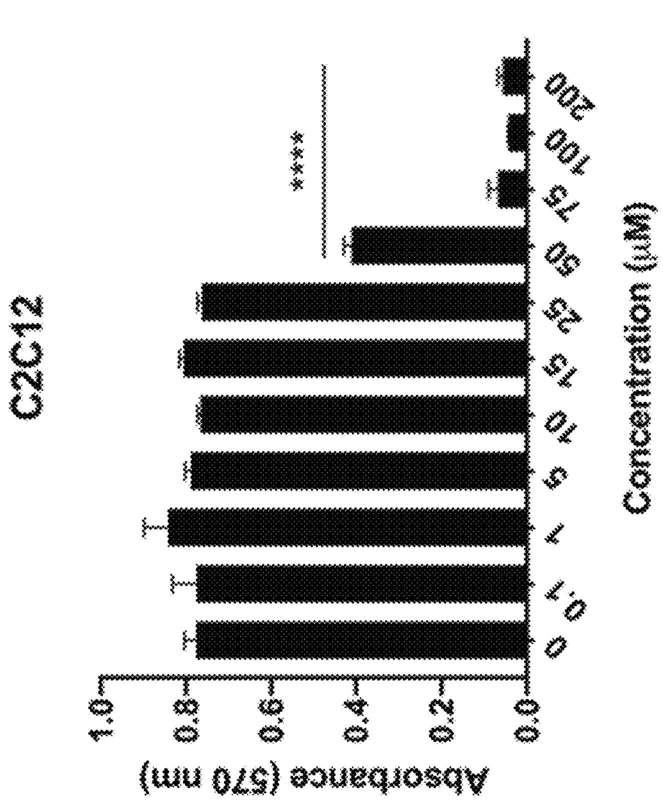
Figure 11D:
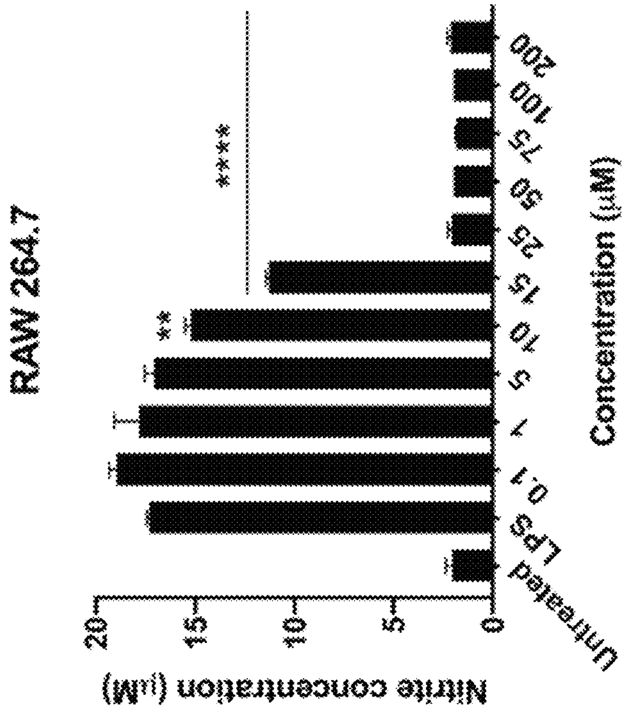
FIG. 11D is a graph of nitric oxide concentration (μM) versus concentration of 4-(5-(4 hydroxyphenyl)-1-methyl-1H-pyrazol-3-yl)-5-methoxy-2-(3-methylbut-2-en-1-yl)benzene-1,3-diol (μM) providing data concerning the inhibitory effect of 4-(5-(4-hydroxyphenyl)-1-methyl-1H-pyrazol-3-yl)-5-methoxy-2-(3-methylbut-2-en-1-yl)benzene-1,3-diol on nitric oxide (NO) production by LPS-stimulated macrophages.
Figure 11C:
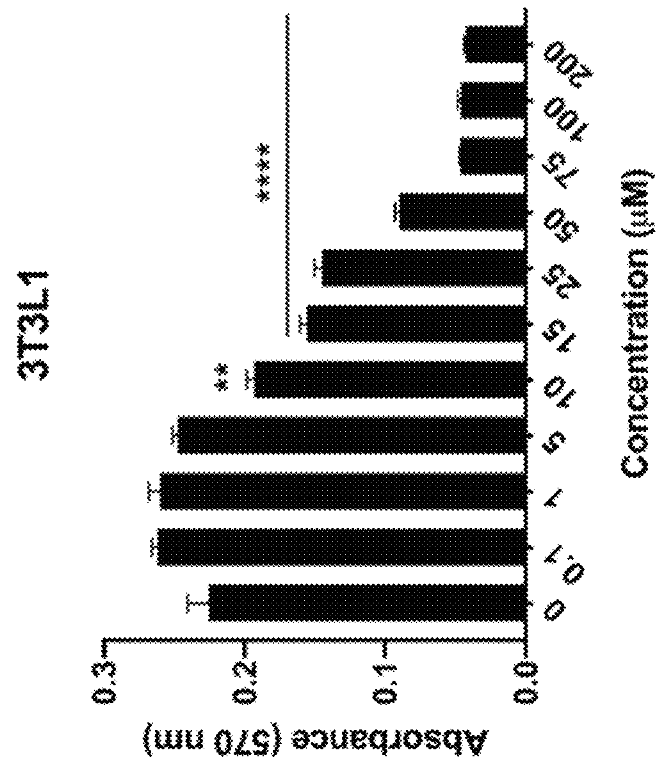

1. Effect of 4-(5-(4-hydroxyphenyl)-1-methyl-1h-pyrazol-3-yl)-5-methoxy-2-(3-methylbut-2-en-1-yl) benzene-1,3-diol on Cell Viability In Vitro To assess the toxicity of 4-(5-(4-hydroxyphenyl)-1-methyl-1h-pyrazol-3-yl)-5-methoxy-2-(3-methylbut-2-en-1-yl)benzene-1,3-diol (XP), in vitro cell viability assays were performed on several cell lines. HepG2, 3T3L1 and C2Cl2 cells were exposed to XP and cell viability was assessed using an MTT assay. At concentrations lower than 50 μM, XP had no effect on the viability of the human liver cancer cell lines HepG2 and murine myoblast cell lines C2Cl2 with respect to the control treatment (FIGS. 11A-11B). Xanthohumol is cytotoxic in HepG2 and C2Cl2 cells at concentrations above 25 μM, which shows that xanthohumol and XP have similar toxicity profiles. This establishes that XP is safe to use in vivo at dosages similar to xanthohumol. The dose-dependent reduction in cell viability occurred at lower concentrations of XP (10 μM) in the differentiated murine adipocyte cell lines 3T3L1 (FIG. 11C) and suggests a toxicity of XP specific to adipocytes.

Figure 11E:
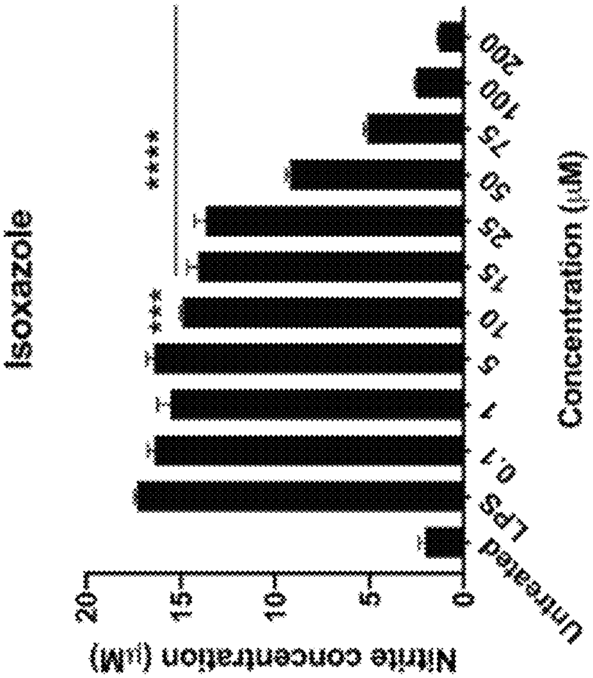
FIG. 11E is a graph of nitric oxide concentration (μM) versus concentration of 4-(5-(4 hydroxyphenyl)isoxazol-3-yl)-5-methoxy-2-(3-methylbut-2-en-1-yl)benzene-1,3-diol (μM) providing data concerning the inhibitory effect of 4-(5-(4-hydroxyphenyl)isoxazol-3-yl)-5-methoxy-2-(3-methylbut-2-en-1-yl)benzene-1,3-diol on nitric oxide (NO) production by LPS-stimulated macrophages.
Figure 11F:
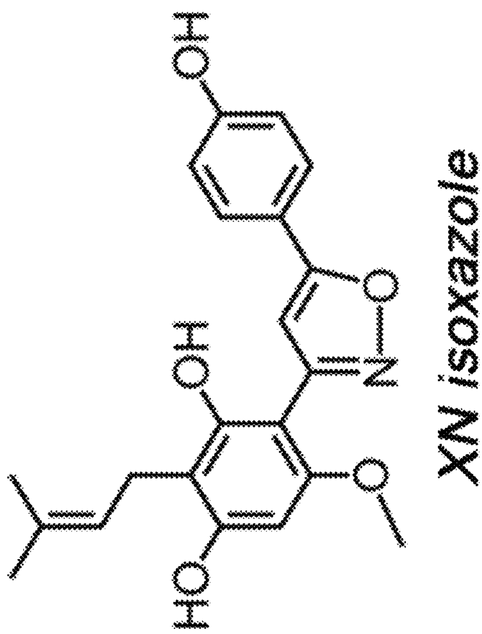
FIG. 11F provides the structure of an exemplary isoxazole derivative of XN, specifically 4-(5-(4-hydroxyphenyl)isoxazole-3-yl)-5-methoxy-2-(3-methylbut-2-en-1-yl)benzene-1,3-diol.

Nitric oxide (NO) production was decreased in macrophages exposed to LPS after treatment with pyrazole and isoxazole derivatives of xanthohumol. XP displayed anti-inflammatory activities starting at doses of 10 μM (FIG. 11D), similar to the isoxazole derivative (FIGS. 11E-F). This suggests these derivatives might improve HFD-induced inflammation in vivo.

Figure 12A:
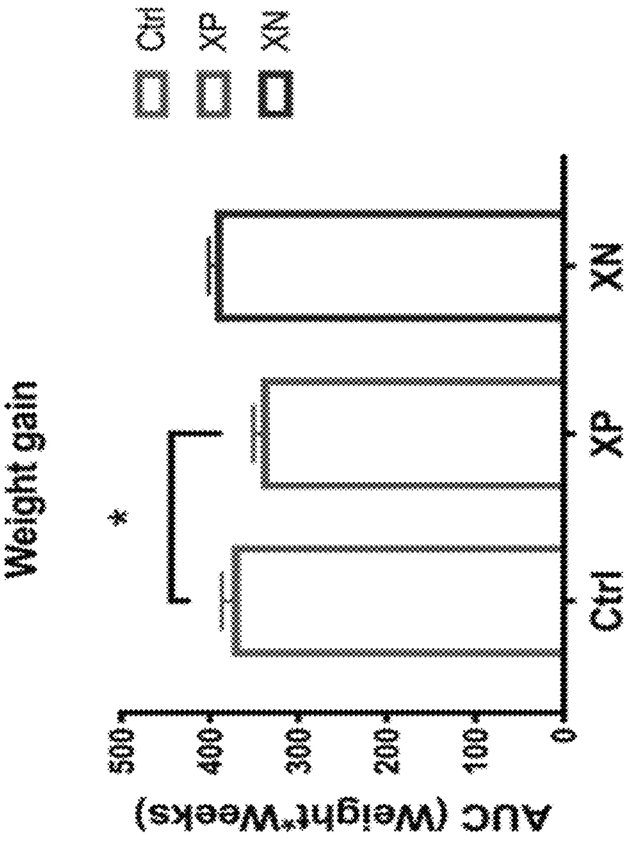
FIG. 12A is a graph of weight gain (grams) for mice administered 4-(5-(4-hydroxyphenyl)-1-methyl-1H-pyrazol-3-yl)-5-methoxy-2-(3-methylbut-2-en-1-yl)benzene-1,3-diol establishing that 4-(5-(4-hydroxyphenyl)-1-methyl-1H-pyrazol-3-yl)-5-methoxy-2-(3-methylbut-2-en-1-yl)benzene-1,3-diol decreased weight gain in HFD-fed mice relative to a control and xanthohumol (data is represented as mean±SEM (n=4-8 per group). *$p<0.05$; $p<0.01$; *$p<0.001$; ****$p<0.0001$, repeated measures ANOVA).
Figure 12B:
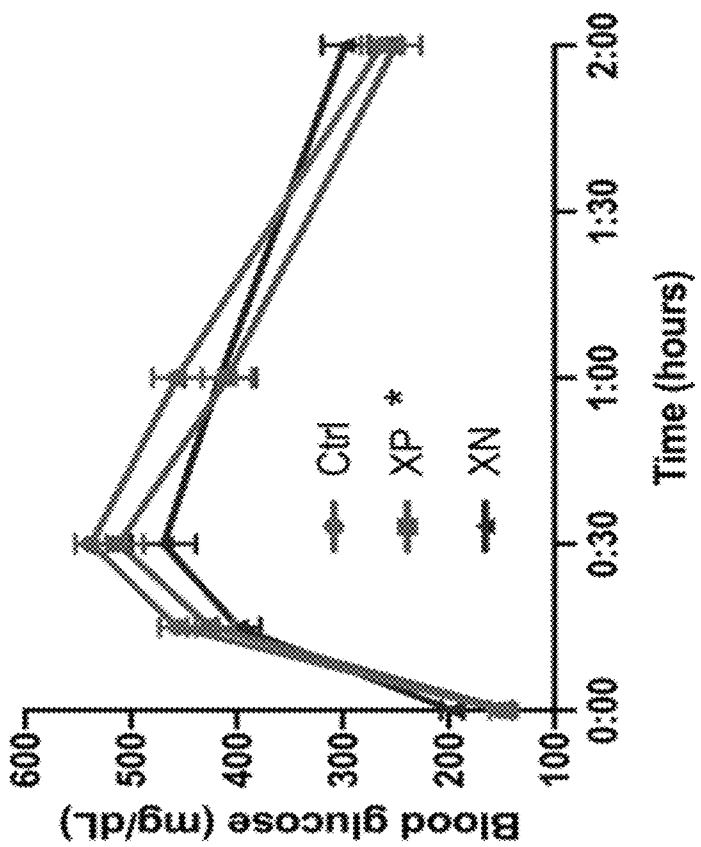
FIG. 12B is a graph of blood glucose (mg/dl) versus time (hours) for mice administered 4-(5-(4-hydroxyphenyl)-1-methyl-1H-pyrazol-3-yl)-5-methoxy-2-(3-methylbut-2-en-1-yl)benzene-1,3-diol establishing that 4-(5-(4-hydroxyphenyl)-1-methyl-1H-pyrazol-3-yl)-5-methoxy-2-(3-methylbut-2-en-1-yl)benzene-1,3-diol improved glucose metabolism in HFD-fed mice relative to the control (data is represented as mean±SEM (n=4-8 per group). *$p<0.05$; $p<0.01$; *$p<0.001$; ****$p<0.0001$, repeated measures ANOVA).

2. 4-(5-(4-hydroxyphenyl)-1-methyl-1h-pyrazol-3-yl)-5-methoxy-2-(3-methylbut-2-en-1-yl)benzene-1,3-diol Decreased Weight Gain and Improved Glucose Metabolism HFD-fed mice supplemented with XP gained significantly less weight over the feeding period than control HFD-fed mice (p<0.0001, FIG. 12A). On the other hand, mice treated with XN exhibited no change in weight compared to the control mice. After 4 weeks of feeding, a glucose tolerance test (GTT) was performed and established that XP improved glucose tolerance in mice fed a HFD (p=0.03, FIG. 12B), while xanthohumol had no effect on glucose clearance assessed by GTT. After 11 weeks of feeding, the Homeostatic Model Assessment of Insulin Resistance (HOMA-IR), known as the insulin resistance score, was decreased by 77.9% (p=0.01, Tablet) in HFD-fed 4-(5-(4-hydroxyphenyl)-1-methyl-1h-pyrazol-3-yl)-5-methoxy-2-(3-methylbut-2-en-1-yl)benzene-1,3-diol-treated mice. These results establish that XP improves insulin sensitivity, which leads to more effective regulation of blood glucose concentrations.

3. 4-(5-(4-hydroxyphenyl)-1-methyl-1h-pyrazol-3-yl)-5-methoxy-2-(3-methylbut-2-en-1-yl)benzene-1,3-diol Did Not Change Plasma Concentrations of Pro-Inflammatory Cytokines and Markers of Liver Damage Plasma concentrations of inflammatory cytokines often associated with obesity were measured. The monocyte chemoattractant protein-1 (MCP-1/CCL2) levels were not decreased in 4-(5-(4-hydroxyphenyl)-1-methyl-1h-pyrazol-3-yl)-5-methoxy-2-(3-methylbut-2-en-1-yl)benzene-1,3-diol-treated mice, while pro-inflammatory cytokine IL-6 was not significantly different in 4-(5-(4-hydroxyphenyl)-1-methyl-1h-pyrazol-3-yl)-5-methoxy-2-(3-methylbut-2-en-1-yl)benzene-1,3-diol-treated mice compared to control mice. To assess liver toxicity associated with the treatment, enzymatic activities of Aspartate Aminotransferase (AST) and Alanine Aminotransferase (ALT) in liver homogenates of control and treated mice were measured. AST and ALT tests results did not change substantially in 4-(5-(4-hydroxyphenyl)-1-methyl-1h-pyrazol-3-yl)-5-methoxy-2-(3-methylbut-2-en-1-yl)benzene-1,3-diol-treated mice or in xanthohumol-treated mice compared to control mice, which indicates that the test compounds do not cause liver damage in vivo. See Table 1, below, which provides a list of metabolic parameters measured in male mice upon 4 weeks ([a]) or 11 weeks of HFD±test compounds. Data displayed as mean±SEM (n-4-8 per group). Significant differences are marked as *p<0.05, p<0.01, *p<0.001, one-way ANOVA. There were no changes in triglycerides (TG) and total cholesterol concentrations in the plasma of 4-(5-(4-hydroxyphenyl)-1-methyl-1h-pyrazol-3-yl)-5-methoxy-2-(3-methylbut-2-en-1-yl)benzene-1,3-diol-treated mice (Table 1). An increase of plasma TGs in XN-treated mice (Table 1) was observed. The plasma concentrations of the proprotein convertase subtilisin/kexin type 9 (PCSK9) that induces LDL receptor degradation in hepatocytes and regulates plasma LDL-cholesterol were not affected by XP or XN (Table 1).

TABLE 1

| Parameter Measured | Control | 4-(5-(4-hydroxyphenyl)-1-methyl-1h-pyrazol-3-yl)-5-methoxy-2-(3-methylbut-2-en-1-yl)benzene-1,3-diol | Xanthohumol |
|---|---|---|---|
| Initial body weight (g) | 24.97 ± 0.73 | 23.66 ± 0.70 | 26.37 ± 0.22 |
| Final body weight (g) | 40.42 ± 1.94 | 37.87 ± 1.72 | 44.25 ± 1.97 |
| Fasting glucose [a] (mg/dL) | 150.87 ± 10.55 | 143.62 ± 7.54 | 196.75* ± 10.68 |
| Fasting glucose (mg/dL) | 120.39 ± 13.50 | 128.98 ± 7.18 | 142.67 ± 6.29 |
| Insulin (μU/mL) | 77.71 ± 29.15 | 34.36 ± 3.73 | 71.17 ± 34.38 |
| HOMA-IR | 49.56 ± 18.19 | 10.94* ± 1.52 | 26.76 ± 13.47 |
| AST (U/mL) | 0.45 ± 0.13 | 0.30 ± 0.06 | 0.16 ± 0.03 |
| ALT (U/mL) | 0.55 ± 0.22 | 0.38 ± 0.07 | 0.22 ± 0.06 |
| MCP1 (pg/mL) | 69.20 ± 14.07 | 45.00 ± 4.68 | 57.34 ± 15.74 |
| IL-6 (pg/mL) | 1.43 ± 0.53 | 5.78 ± 2.04 | 5.03 ± 3.3 |
| PCSK9 (ng/mL) | 211 ± 15.80 | 217.166 ± 26.88 | 215 ± 35.12 |
| Plasma TG (mg/dL) | 87.39 ± 13.17 | 81.81 ± 4.33 | 173.13** ± 23.24 |
| Plasma cholesterol (mg/dL) | 175.56 ± 5.70 | 160.47 ± 4.73 | 170.88 ± 6.76 |

[a] = measured in male mice at 4 weeks.

To assess liver toxicity associated with the treatment, enzymatic activities of AST and ALT in liver homogenates of control and treated mice were measured. 4-(5-(4-hydroxyphenyl)-1-methyl-1h-pyrazol-3-yl)-5-methoxy-2-(3-methylbut-2-en-1-yl)benzene-1,3-diol-treated mice had 30% decrease in liver enzymes; the decrease was not significant, but it indicates that the treatment did not induce liver toxicity (Table 1).

Figure 13B:
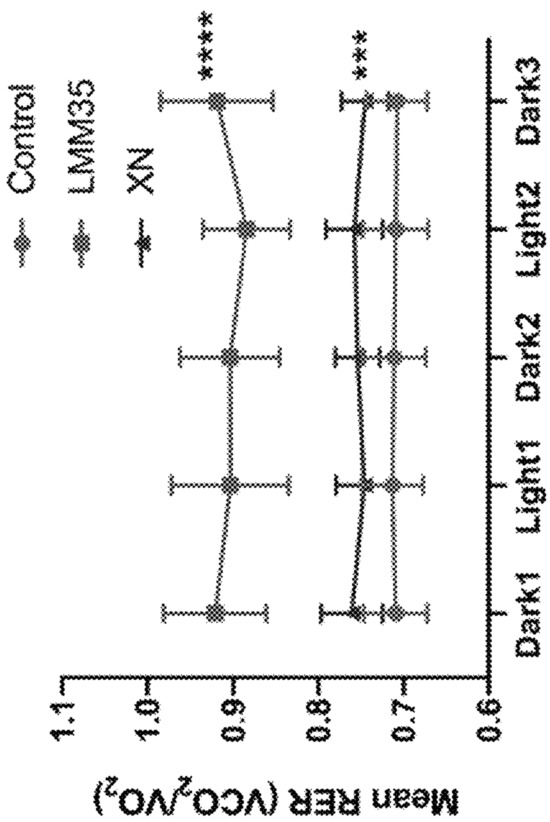
FIG. 13B is a graph of mean respiratory exchange ratio ($VCO_2/VO_2$) during light and dark cycles establishing that 4-(5-(4-hydroxyphenyl)-1-methyl-1H-pyrazol-3-yl)-5-methoxy-2-(3-methylbut-2-en-1-yl)benzene-1,3-diol increased respiratory exchange ratio in HFD-fed mice relative to mice administered xanthohumol and control.
Figure 13A:
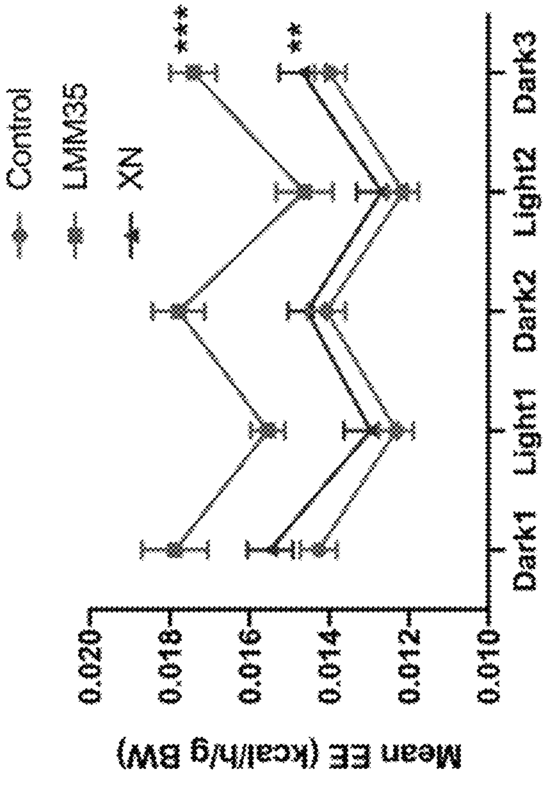
FIG. 13A is a graph of mean energy expenditure (kcal/h/g body weight) during light and dark cycles establishing that 4-(5-(4-hydroxyphenyl)-1-methyl-1H-pyrazol-3-yl)-5-methoxy-2-(3-methylbut-2-en-1-yl)benzene-1,3-diol increased energy expenditure in HFD-fed mice relative to mice administered xanthohumol and a control.
Figure 13C:
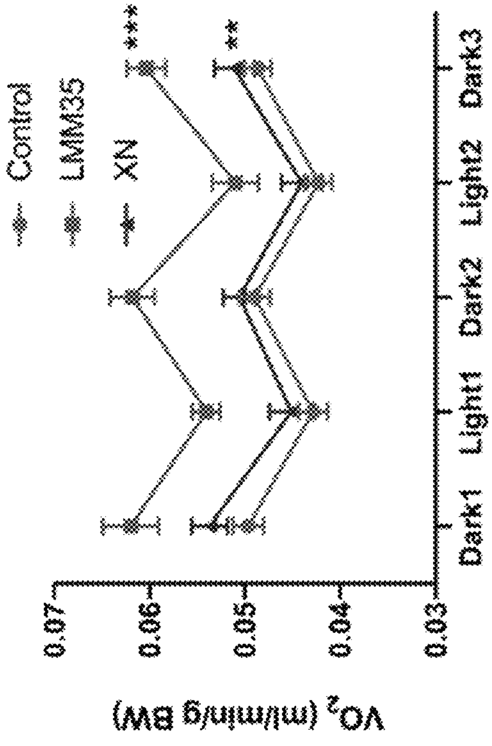
FIG. 13C is a graph of consumed 02 volume (ml/min/g body weight) during dark and light cycles establishing that 4-(5-(4-hydroxyphenyl)-1-methyl-1H-pyrazol-3-yl)-5-methoxy-2-(3-methylbut-2-en-1-yl)benzene-1,3-diol increased 02 consumption in HFD-fed mice relative to mice administered xanthohumol and control.
Figure 13D:
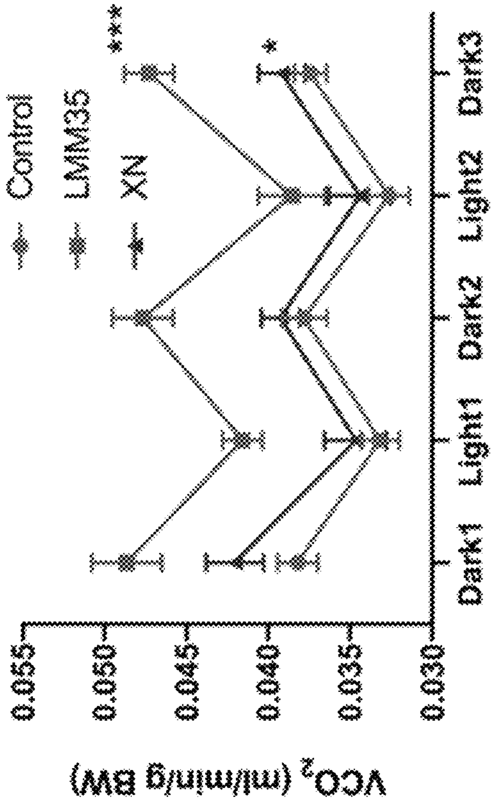
FIG. 13D is a graph of released $CO_2$ volume (ml/min/g body weight) during dark and light cycles establishing that 4-(5-(4-hydroxyphenyl)-1-methyl-1H-pyrazol-3-yl)-5-methoxy-2-(3-methylbut-2-en-1-yl)benzene-1,3-diol increased $CO_2$ emission in HFD-fed mice relative to mice administered xanthohumol and control.
Figure 13F:
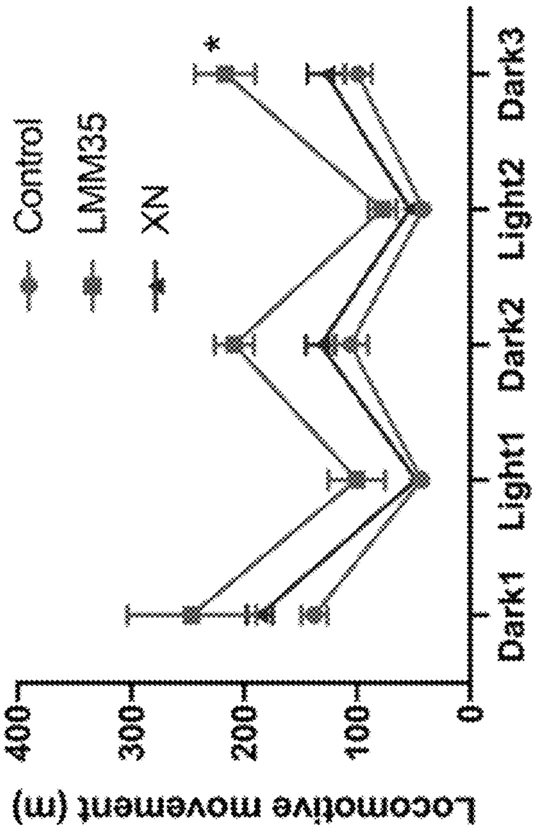
FIG. 13F is a graph of locomotive movement (m) during dark and light cycles establishing that 4-(5-(4-hydroxyphenyl)-1-methyl-1H-pyrazol-3-yl)-5-methoxy-2-(3-methylbut-2-en-1-yl)benzene-1,3-diol increased locomotive movement in HFD-fed mice relative to xanthohumol and a control.
Figure 13E:
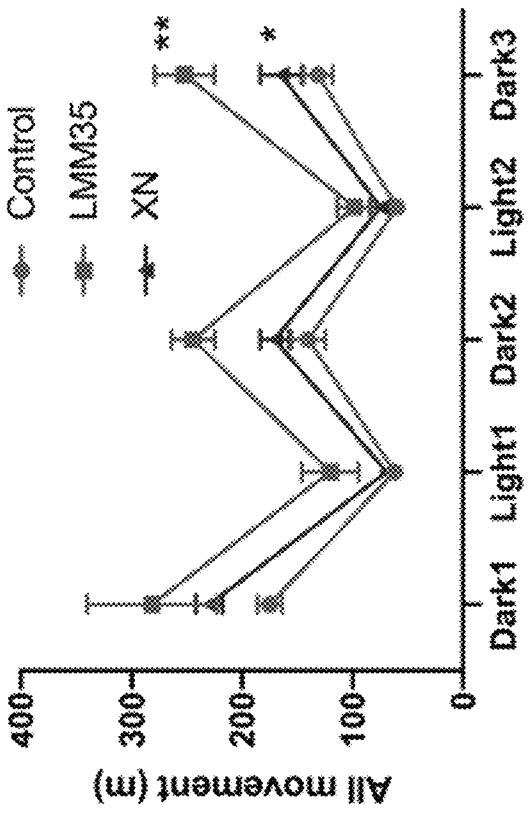
FIG. 13E is a graph of all movement (m) during dark and light cycles establishing that 4-(5-(4-hydroxyphenyl)-1-methyl-1H-pyrazol-3-yl)-5-methoxy-2-(3-methylbut-2-en-1-yl)benzene-1,3-diol increased all movement in HFD-fed mice relative to xanthohumol and a control.
Figure 13G:
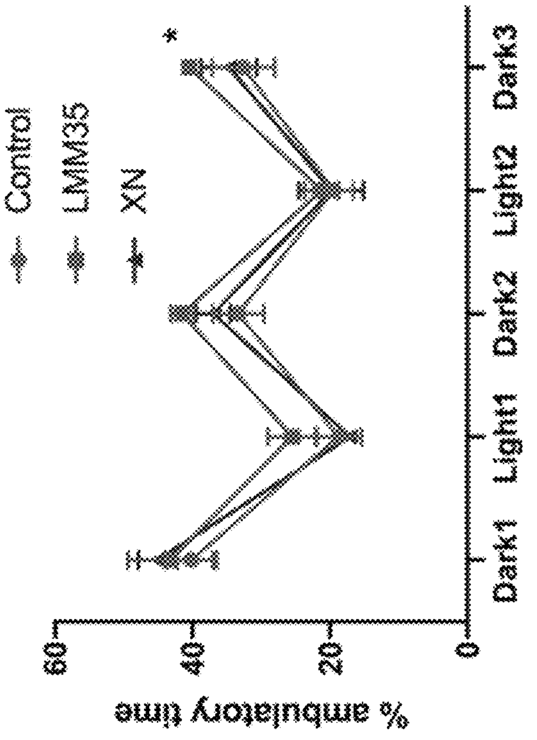
FIG. 13G is a graph of % ambulatory time during dark and light cycles establishing that 4-(5-(4 hydroxyphenyl)-1-methyl-1H-pyrazol-3-yl)-5-methoxy-2-(3-methylbut-2-en-1-yl)benzene-1,3-diol increased ambulatory time in HFD-fed mice relative to xanthohumol and a control.
Figure 13H:
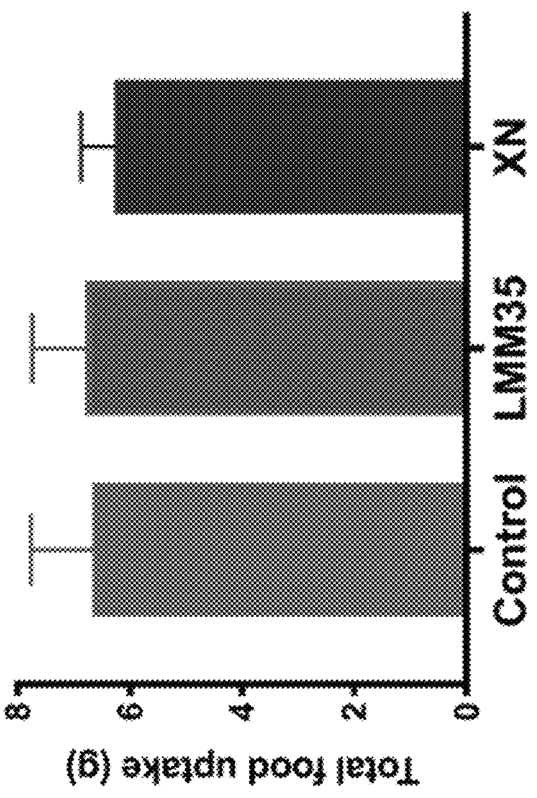
FIG. 13H is a bar graph of total food intake (grams) for HFD-fed mice that also received 4-(5-(4-hydroxyphenyl)-1-methyl-1H-pyrazol-3-yl)-5-methoxy-2-(3-methylbut-2-en-1-yl)benzene-1,3-diol or xanthohumol relative to control.
Figure 14A:
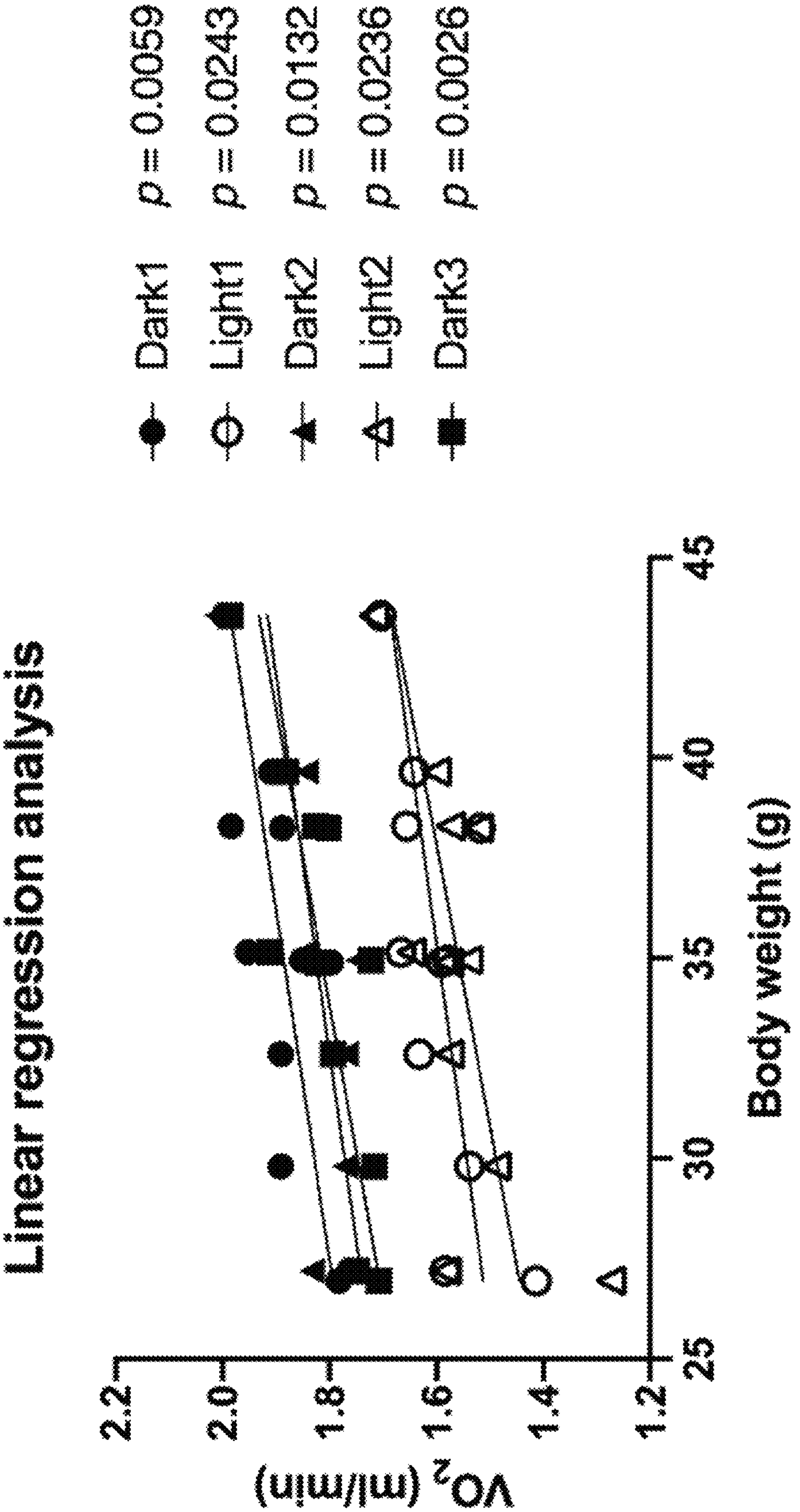
FIG. 14A is a graph of body weight (g) versus $VO_2$ (ml/min).
Figure 14B:
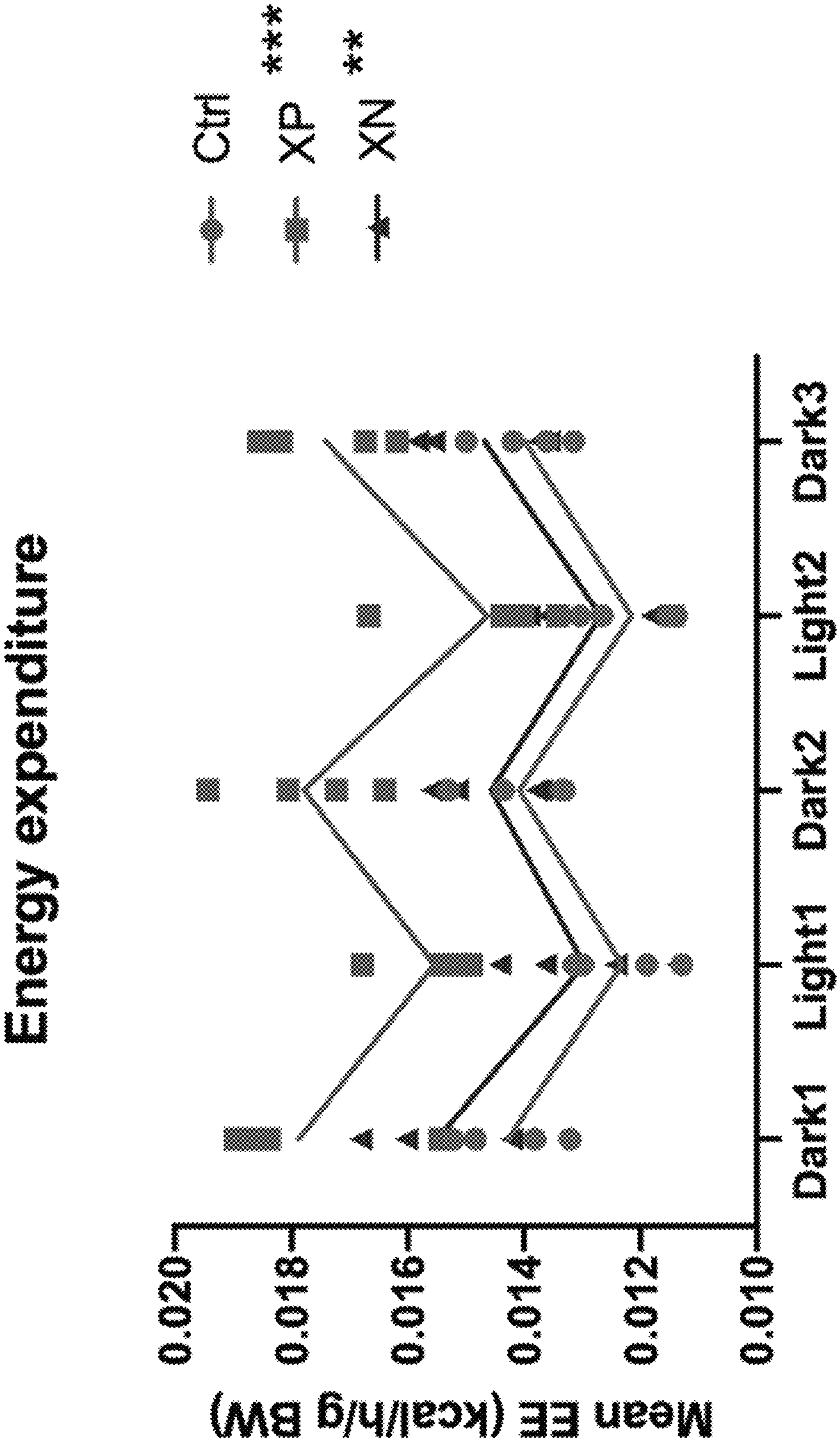
FIG. 14B is a graph of mean energy expenditure (kcal/h/g body weight) during light and dark cycles establishing that 4-(5-(4-hydroxyphenyl)-1-methyl-1H-pyrazol-3-yl)-5-methoxy-2-(3-methylbut-2-en-1-yl)benzene-1,3-diol increased energy expenditure in HFD-fed mice relative to mice administered xanthohumol and a control.
Figure 14C:
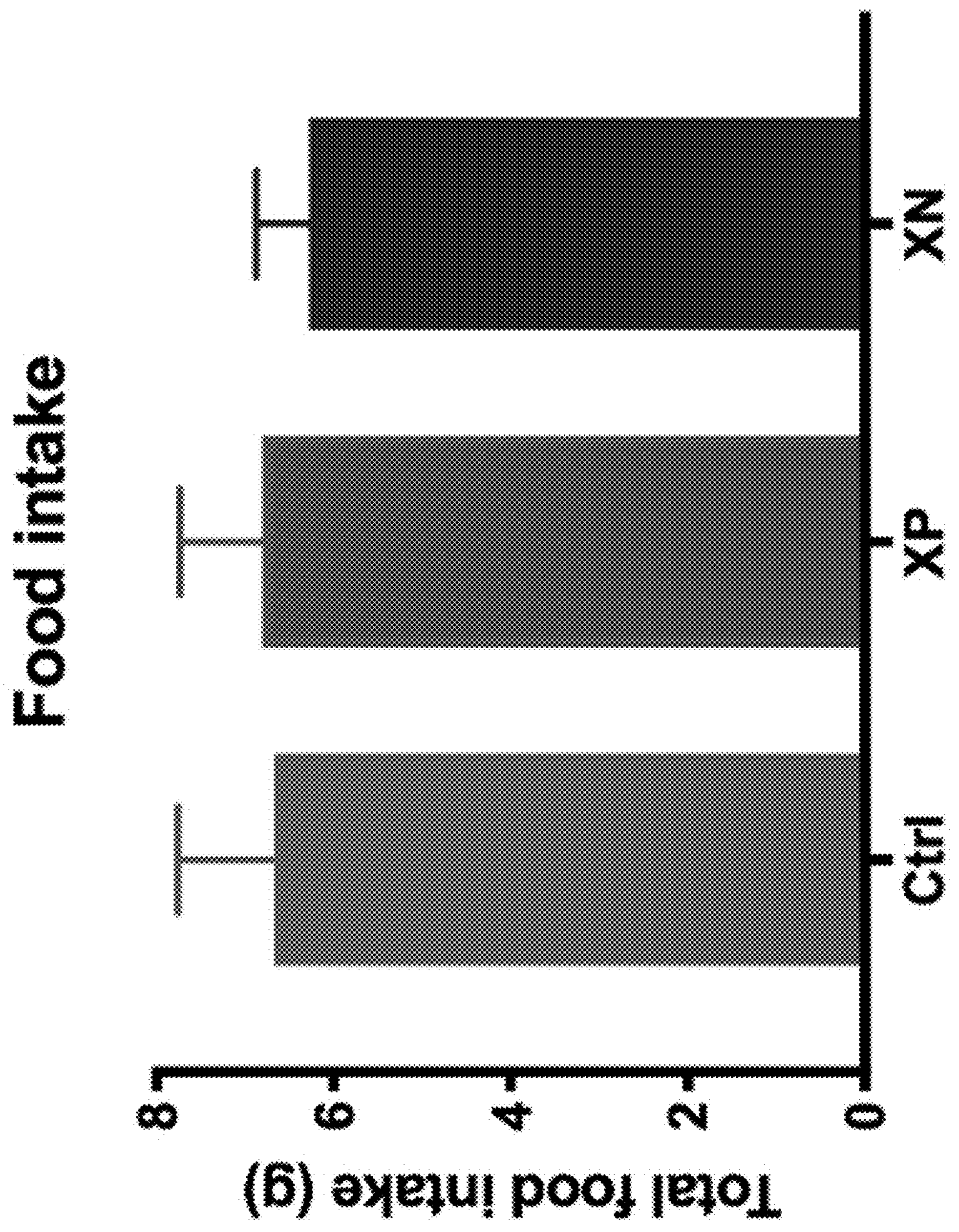
FIG. 14C is a bar graph of total food intake (grams) for HFD-fed mice that also received 4-(5-(4-hydroxyphenyl)-1-methyl-1H-pyrazol-3-yl)-5-methoxy-2-(3-methylbut-2-en-1-yl)benzene-1,3-diol or xanthohumol relative to a control.

4. 4-(5-(4-hydroxyphenyl)-1-methyl-1h-pyrazol-3-yl)-5-methoxy-2-(3-methylbut-2-en-1-yl)benzene-1,3-diol Increased Energy Expenditure in HFD-Fed Mice Energy expenditure (EE) was measured in XP-treated HEF-fed mice during three successive dark and light cycles using metabolic cages. The metabolic parameters were normalized on body weight to correct for the changes in weight between treatment groups. FIG. 14A. Mean EE, a measure of the amount of energy mice burn per hour, was increased by 20-27% in 4-(5-(4-hydroxyphenyl)-1-methyl-1h-pyrazol-3-yl)-5-methoxy-2-(3-methylbut-2-en-1-yl)benzene-1,3-diol-treated mice (p=0.0002) and 4-8% in xanthohumol-treated mice (p=0.01, FIG. 13A and FIG. 14B). Mean respiratory exchange ratio (RER), which reflects the respiratory exchange of $CO_2$ and 02, was increased in 4-(5-(4-hydroxyphenyl)-1-methyl-1h-pyrazol-3-yl)-5-methoxy-2-(3-methylbut-2-en-1-yl)benzene-1,3-diol-treated mice ($p<0.0001$) and xanthohumol-treated mice (p=0.0004, FIG. 13B). This indicates higher ventilation rates in the treatment groups. As expected, volumes of 02 consumed and $CO_2$ produced were also increased in both treatment groups (FIGS. 13C-D). There was no change in food intake measured during the calorimetric experiment (FIG. 13H, FIG. 14C). These data indicate that both XN and XP increased daily EE, tipping the balance between energy intake and energy output.

Figure 15A:
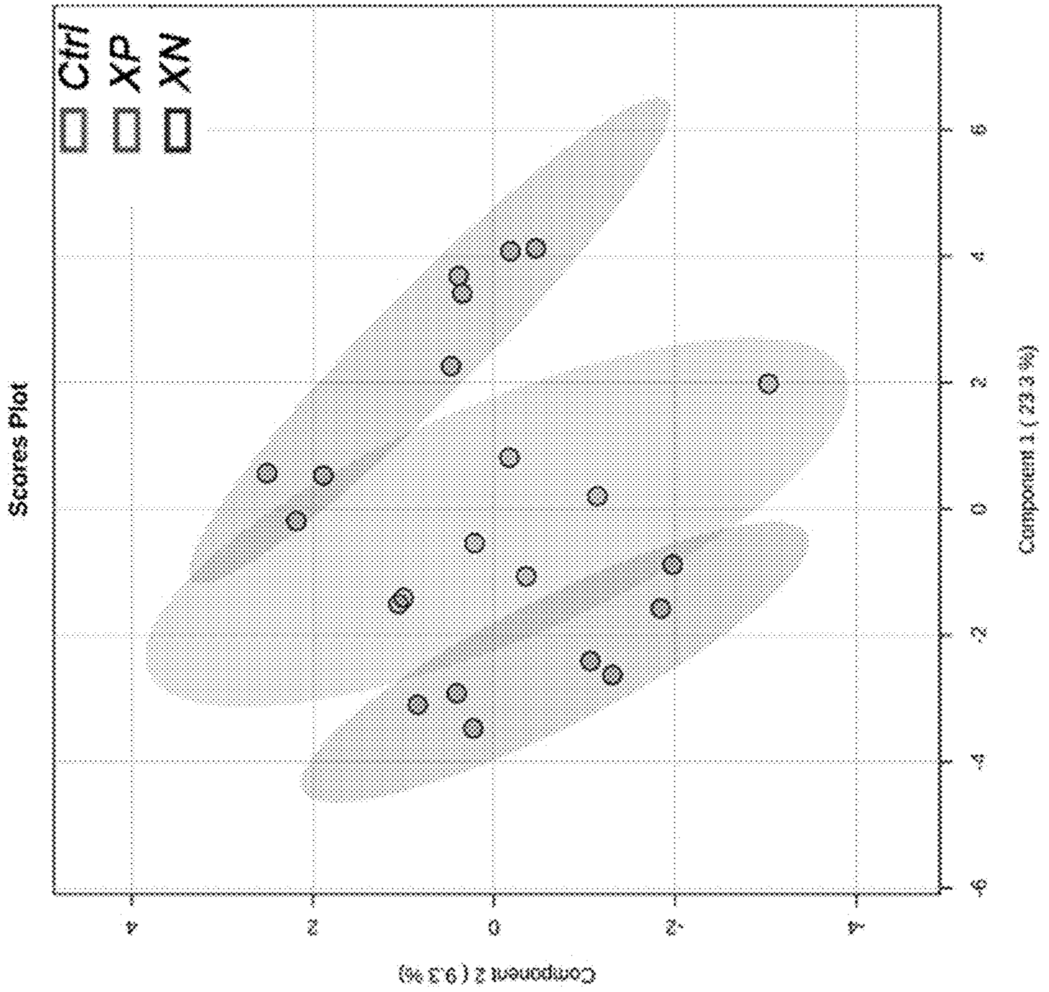
FIG. 15A is a scores plot for 4-(5-(4-hydroxyphenyl)-1-methyl-1H-pyrazol-3-yl)-5-methoxy-2-(3-methylbut-2-en-1-yl)benzene-1,3-diol or xanthohumol relative to control.
Figure 16A:
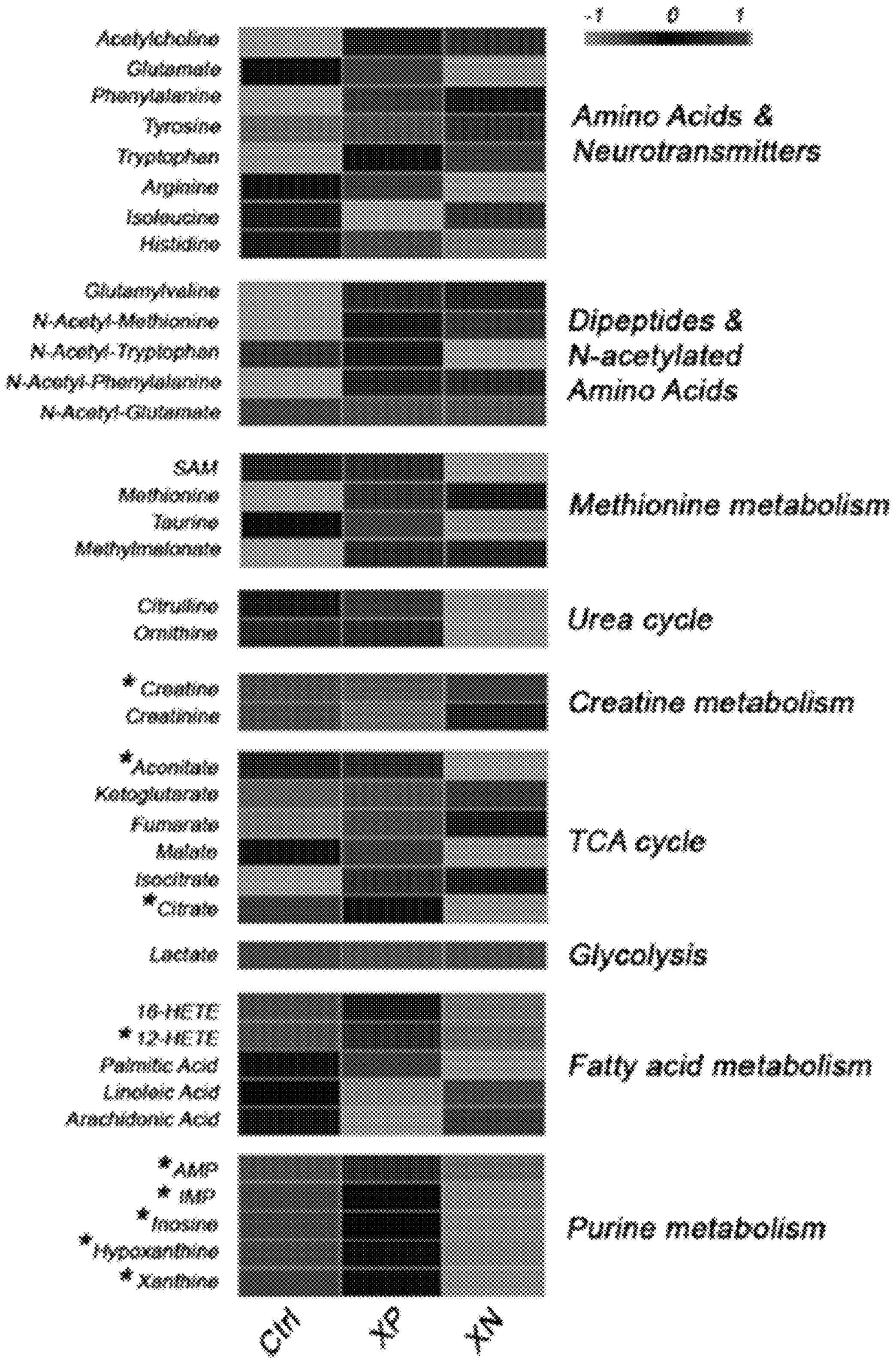
FIG. 16A is a heatmap of relative abundances of individual plasma metabolites.

5. 4-(5-(4-hydroxyphenyl)-1-methyl-1h-pyrazol-3-yl)-5-methoxy-2-(3-methylbut-2-en-1-yl)benzene-1,3-diol Modulates Plasma Metabolome in HFD-Fed Mice An untargeted plasma metabolomics analysis was performed to identify metabolite alterations secondary to increased EE in treated mice and to gain more insight into XP mechanisms of action (FIG. 15A and Table 3, below). 155 metabolites, categorized into major biological processes (FIG. 16A), were annotated. In the plasma of XP-treated mice, a non-significant yet uniform increase in amino acids, dipeptides, and TCA cycle metabolites was inferred by the presence of more intense red cells in the heatmap rows corresponding to analytes from these groups (FIG. 16A). On the other hand, metabolites involved in adenosine triphosphate (ATP) anabolism and catabolism such as creatine, fatty acids (12-HETE), purine metabolites including adenosine monophosphate (AMP), inosine monophosphate (IMP), inosine, hypoxanthine, and xanthine were significantly decreased by XP. In XN-treated mice, 12-HETE, citrate, aconitate, creatine, and purine metabolites were also significantly decreased.

Figure 16B:
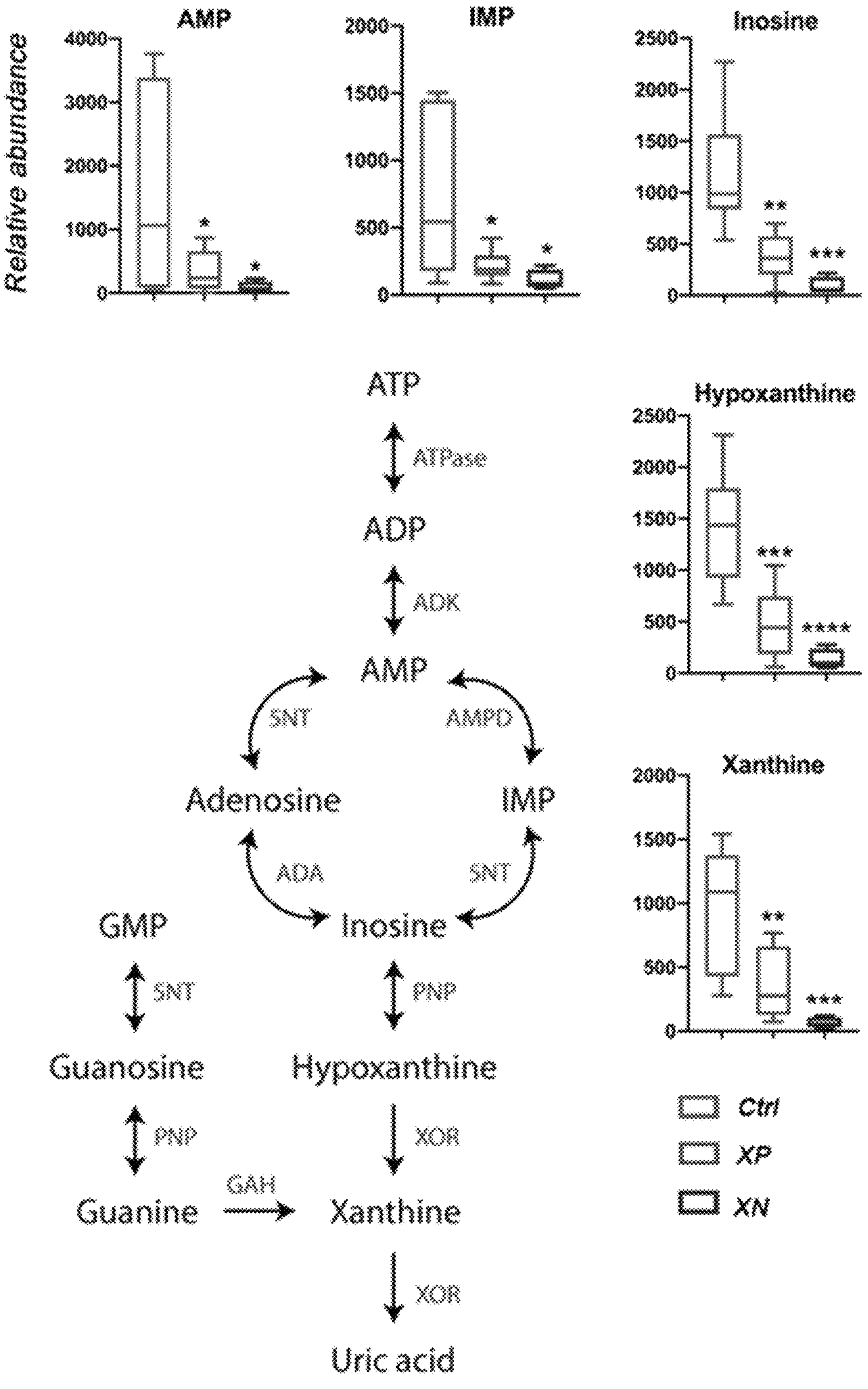
FIG. 16B is a graphical representation of the purine degradation pathway with relative abundances of AMP, IMP, inosine, hypoxanthine, and xanthine in the plasma of HFD-fed mice treated with XP and XN.
Figure 17B:
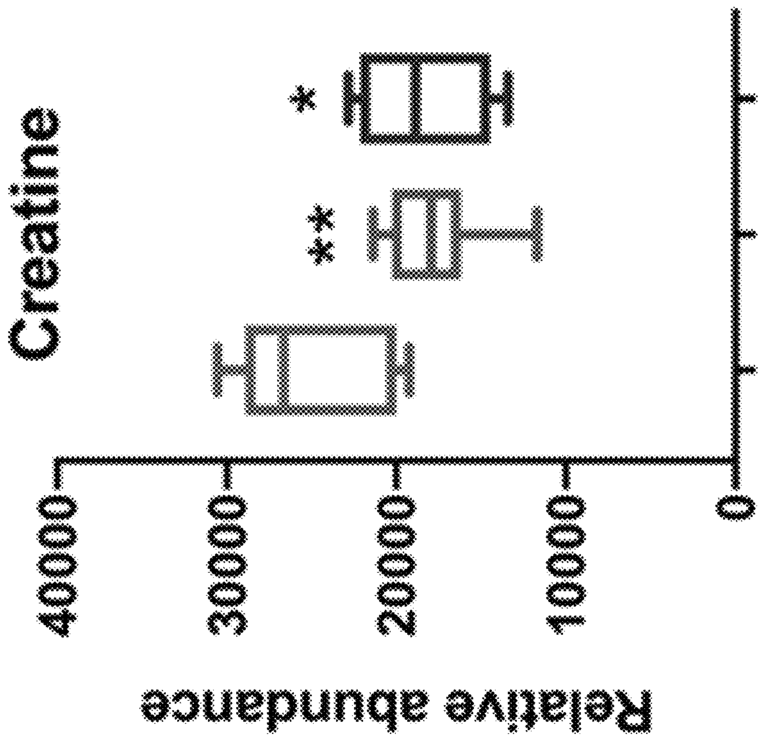
FIGS. 17A-17F are graphs of relative abundances for (A) creatinine, (B) citrate, (C) aconitate, (D) 12-HETE, (E) deoxycytidine and (F) biliverdin in the plasma of HFD-fed mice untreated, treated with XP or treated with XN, where significant differences are marked as *$p<0.05$, $p<0.01$, *$p<0.001$ for effect of treatment, one-way ANOVA.
Figure 17A:
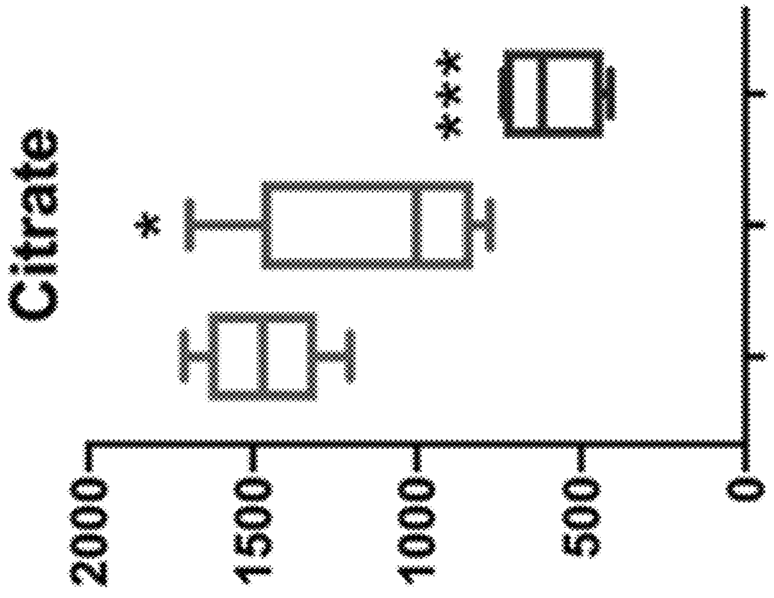
Figure 17C:
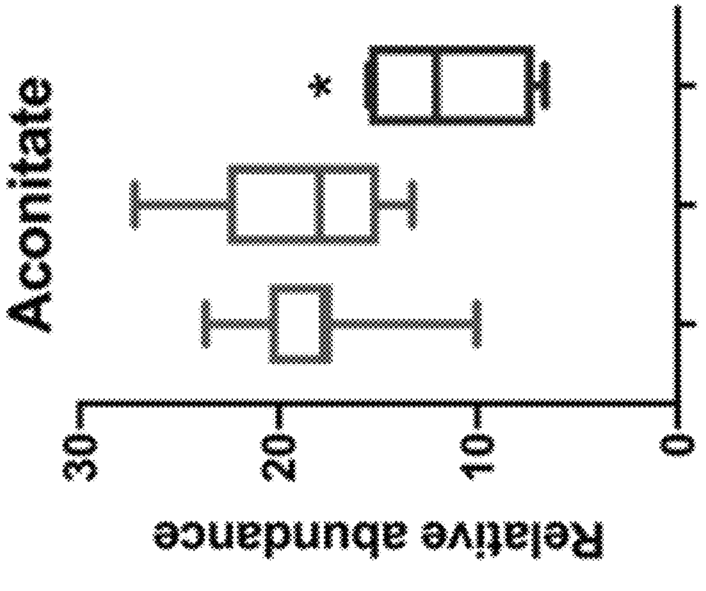
Figure 17D:
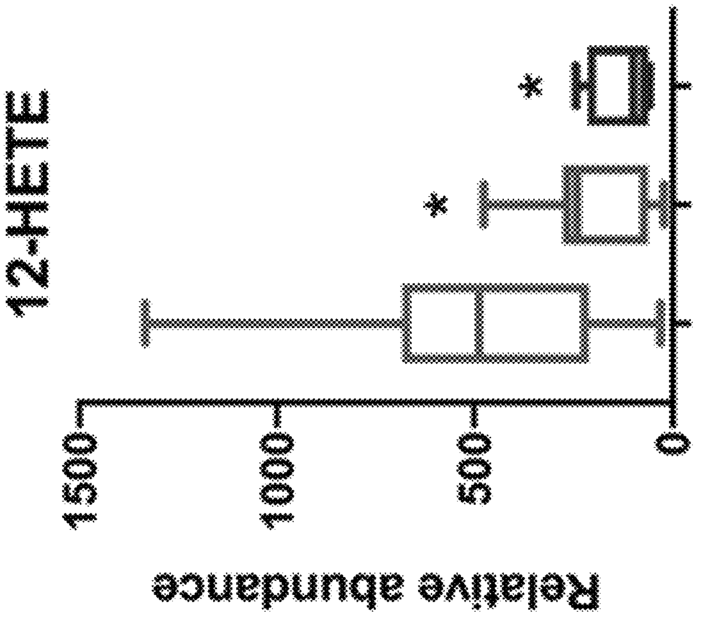
Figure 17F:
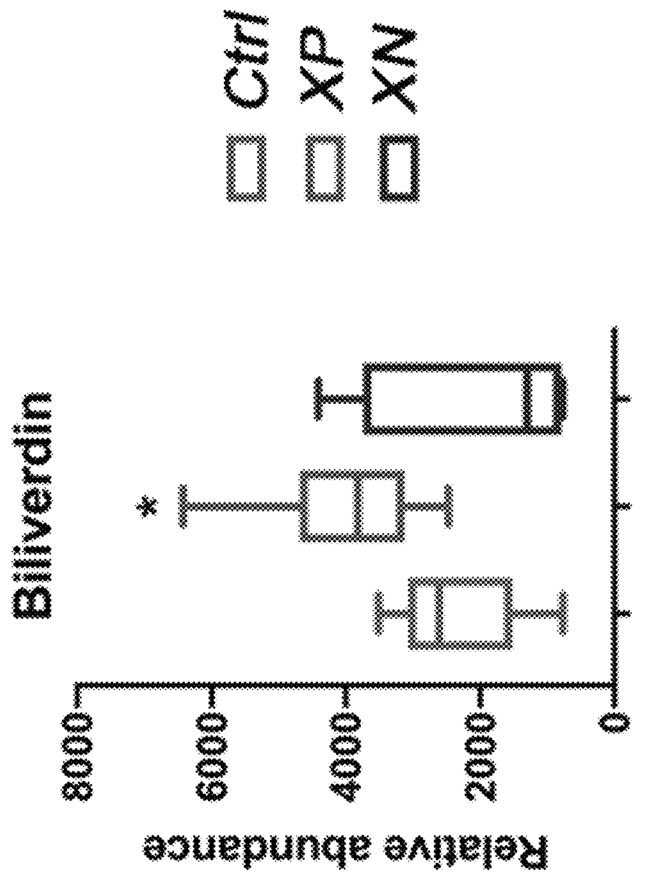
Figure 17E:
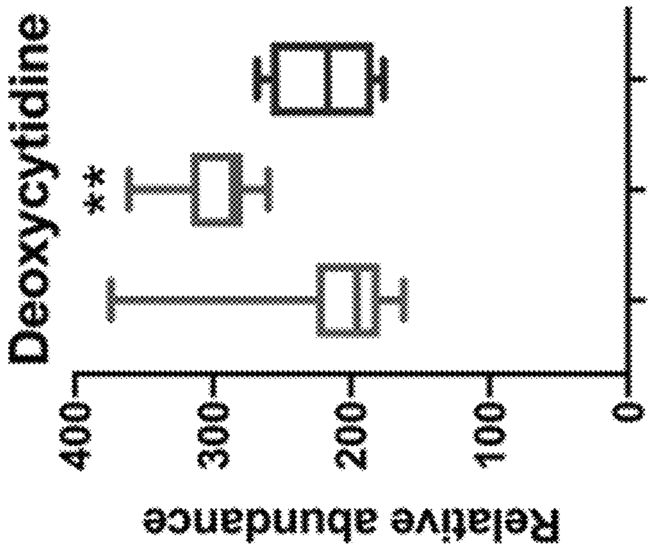

A secondary cellular source of anaerobic ATP is the myokinase reaction converting 2 ADP into AMP and ATP. Therefore, intracellular purine nucleotides act as a reservoir that promotes ATP regeneration by converting excess AMP into IMP and driving forward the myokinase reaction. Out of the 11 metabolites significantly affected by XP or XN treatment, 5 metabolites belonged to purine metabolism pathways (FIG. 16B and FIG. 17). These data indicate that increased EE is associated with the down-regulation of plasma metabolites involved in energy metabolism in XP- and XN-treated mice.

Figure 18A:
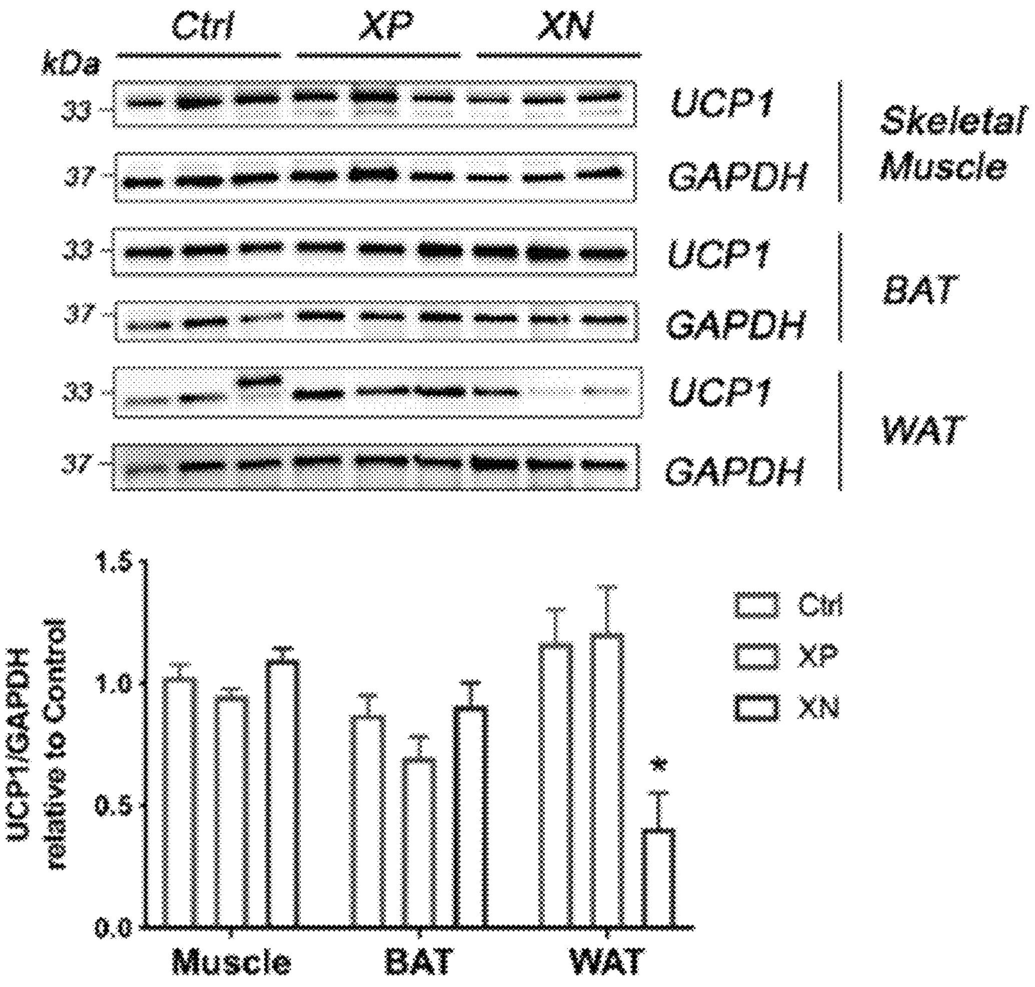
FIG. 18(A) provides Western blots and protein quantification of UCP1 in skeletal muscle, BAT, and WAT of HFD-fed mice control treated with XP or treated with XN.
Figure 18B:
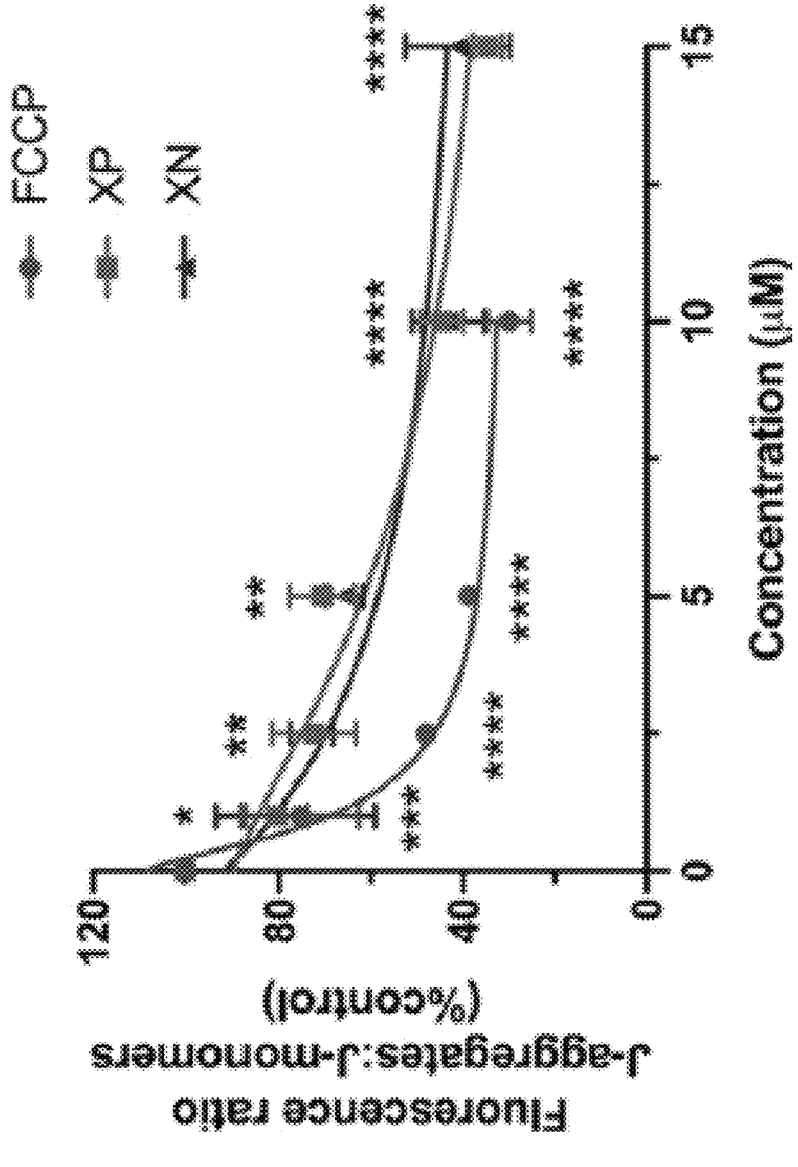
FIG. 18(B) is a graph of fluorescence ratio of JC-1 aggregates and JC-1 monomers versus concentration (μM) in C2C12 cells treated with FCCP, XP, or XN, where data is represented as mean±SEM (n=3 per group). *$p<0.05$, $p<0.01$, *$p<0.001$, and ****$p<0.0001$, one-way ANOVA.

6. 4-(5-(4-hydroxyphenyl)-1-methyl-1h-pyrazol-3-yl)-5-methoxy-2-(3-methylbut-2-en-1-yl)benzene-1,3-diol Uncouples Oxidative Phosphorylation in C2C12 Cells Mitochondrial respiration is coupled to ATP synthesis through an electrochemical proton gradient. Proton leak across the inner membrane results in depolarization of the mitochondrial transmembrane without deleteriously lowering the ATP synthesis. Proton leak can be mediated by UCPs and leads to the dissipation of the energy derived from substrate oxidation as heat. Considering the XP and XN effect on EE, the thermogenic activity was evaluated by assessing changes in UCP1 protein expression in the skeletal muscle, BAT, and WAT of HFD-fed mice. Unexpectedly, XP had no effect in UCP1 in the skeletal muscle, BAT, or WAT of HFD-fed mice (FIG. 18A). The UCP1 protein expression was decreased in the WAT of XN-treated mice, and no significant changes were observed in the UCP1 protein expression in the skeletal muscle and BAT of these mice (FIG. 18A). These data indicate that the XP and XN thermogenic effect is not mediated by UCP1 upregulation in HFD-fed mice. Therefore, the XP intrinsic protonophore properties were investigated by measured variations of mitochondrial membrane potential ($\Delta\psi M$) in C2C12 cells stained with JC-1 dye. In cells with low $\Delta\psi M$, JC-1 remains in the monomeric form and exhibits green fluorescence, while in cells with high $\Delta\psi M$, JC-1 aggregates to exhibit red fluorescence. In C2C12 cells treated for 60 minutes, XP and XN decreased the ratio of JC-1 aggregates to JC-1 monomers at concentrations as low as 1 μM (FIG. 18B). The effects of XP and XN were dose-dependent and milder than that of protonophore FCCP, a potent uncoupler of oxidative phosphorylation. The decrease in the ratio of red-to-green fluorescence is indicative of a lower polarization of the mitochondrial membrane in XP-treated cells, suggesting that XP acts as a protonophore.

7. 4-(5-(4-hydroxyphenyl)-1-methyl-1h-pyrazol-3-yl)-5-methoxy-2-(3-methylbut-2-en-1-yl)benzene-1,3-diol Increase Ambulatory Locomotor Activity in HFD-Fed Mice Motor activity along with EE was measured during three successive dark cycles and two successive light cycles. All movements including direct locomotion and fine movements such as grooming an scratching were increased in 4-(5-(4-hydroxyphenyl)-1-methyl-1h-pyrazol-3-yl)-5-methoxy-2-(3-methylbut-2-en-1-yl)benzene-1,3-diol-treated mice (p=0.009) and xanthohumol-treated mice (p=0.04, FIG. 13E). Locomotor movement, an exclusive measure of direct locomotion, increased by 75-135% in 4-(5-(4-hydroxyphenyl)-1-methyl-1h-pyrazol-3-yl)-5-methoxy-2-(3-methylbut-2-en-1-yl)benzene-1,3-diol-treated mice (p=0.009, FIG. 13F) but not xanthohumol-treated mice (p=0.06). Percent ambulatory time—a sum of animal's time spent in ambulatory locomotion, as a percentage of cycle—was increased in 4-(5-(4-hydroxyphenyl)-1-methyl-1h-pyrazol-3-yl)-5-methoxy-2-(3-methylbut-2-en-1-yl)benzene-1,3-diol-treated mice (FIG. 13G). There was no change in food intake measured during the calorimetric experiment (FIG. 13H).

These data suggest that XP also has a central effect, resulting in increased physical activity to enhance the EE and prevent weight gain.

Xanthohumol was previously reported as a mild mitochondrial uncoupler in vitro. Miranda, C. L., Johnson, L. A., de Montgolfier, O., Elias, V. D., et al., Non-estrogenic Xanthohumol Derivatives Mitigate Insulin Resistance and Cognitive Impairment in High-Fat Diet-induced Obese Mice. Sci Rep 2018, 8, 613. Data presented herein suggest that both xanthohumol and 4-(5-(4-hydroxyphenyl)-1-methyl-1h-pyrazol-3-yl)-5-methoxy-2-(3-methylbut-2-en-1-yl)benzene-1,3-diol are mitochondrial uncouplers. This also indicates that 4-(5-(4-hydroxyphenyl)-1-methyl-1h-pyrazol-3-yl)-5-methoxy-2-(3-methylbut-2-en-1-yl)benzene-1,3-diol has an additional central mechanism of action, which enhances its weight gain reduction effects.

Figure 19:
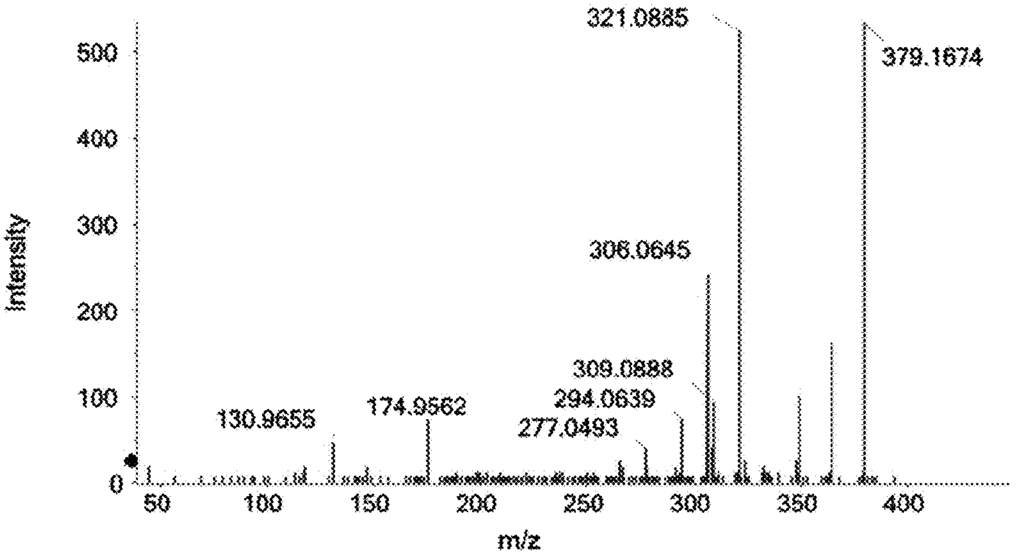
FIG. 19 is a negative ion mode MS/MS spectrum of XP acquired from an AB SCIEX 5600 Triple TOF mass spectrometer with a proposed fragmentation pattern, where HRMS (ES−) m/z: $(M-H]^-$ calculated for $C_{22}H_{23}N_2O_4$ 379.1663, found 379.1674.
Figure 19:
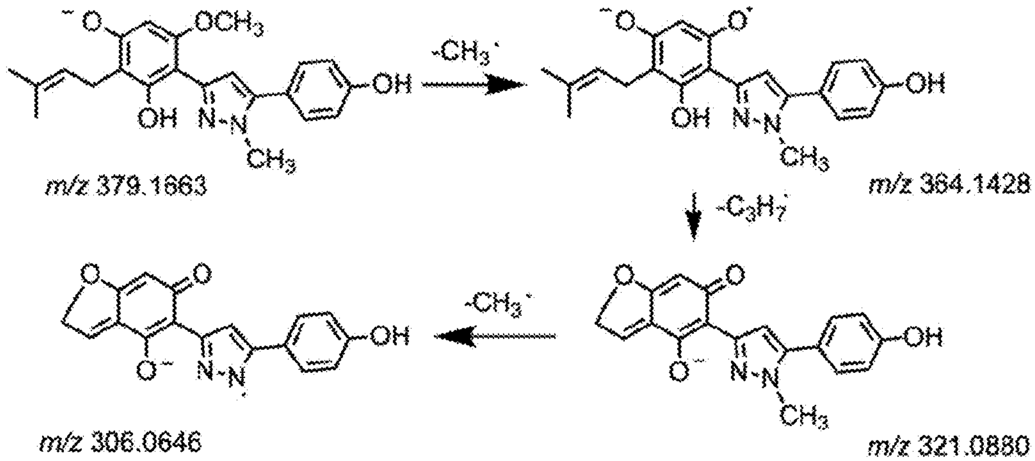

To answer the question whether XP crossed the blood-brain barrier (BBB), concentrations of XP were measured in the cortex and plasma of treated mice by UPLC-MS (Table 2 and FIG. 19).

TABLE 2

Concentrations of XP and XN in the Plasma and Cortex of Treated Mice Following Glucuronidase Digestion or without Glucuronidase Digestion[a]

| | PLASMA (ng/mL) | | CORTEX (ng/g) | |
|---|---|---|---|---|
| | Non-glucuronidated | Glucuronidated + Non-glucuronidated | Non-glucuronidated | Glucuronidated + Non-glucuronidated |
| XP | 43.46 ± 3.54 | 193.81** ± 39.34 | 40.14 ± 2.8 | 39.85 ± 4.56 |
| XN | 13.23 ± 3.07 | 222.64* ± 37.99 | 59.70 ± 16.75 | 360 ± 188.35 |

[a]Concentrations of XP and XN in the plasma of treated mice given daily oral doses of 30 and 60 mg/kg body weight, respectively. Data displayed as mean ± SEM (n = 4-8 per group). Significant differences are marked as *p < 0.05, p < 0.01, and * p < 0.001 for comparisons between free and total pools, two-tailed unpaired t-test.

With glucuronidation being the predominant phase II metabolism for flavonoids including XN, the concentrations of XP with and without glucuronidase digestion were compared. In the plasma, total XP and XN pools measured following glucuronidase treatment were significantly more abundant than their respective aglycone pools. XP was detected in the cortex of XP-treated mice, where no differences were observed between unconjugated XP and total XP concentrations (Table 2). On the other hand, total XN pools were higher in some mice, indicating the presence of glucuronidated XN in the cortex, but there was no significant difference between unconjugated and total XN concentrations. These results suggest that a considerable portion of circulating XP is in the form of O-glucuronide, while non-conjugated XP is the form that crosses the BBB.

XP and XN in plasma were quantified as discussed below in Example 7. XP and XN concentrations were measured following glucuronidase digestion (to determine glucuronide conjugate concentrations) or without glucuronidase digestion (to determine non-conjugated, free compound concentrations). The data are displayed in Table 2 as mean±SEM (n=4-8 per group). Free and total concentrations were significantly different for each compound. The differences between total XP and total XN concentrations were not considered to be statistically significant (p>>0.05, two-tailed t-test).

As a product of metabolism, XP-glucuronide was the only metabolite of XP detected in the plasma samples obtained from mice treated with XP. Mass spectrometric analysis revealed that XP is not converted into its hypothetical O-demethylated metabolite and not converted into its hypothetical dihydro-pyrazole (pyrazoline) metabolite. XP is therefore resistant to phase 1 metabolism, which reduces or eliminates the possibility of side effects exerted by any metabolic products. In this respect, XP has an advantage over XN, as XN is subject to extensive phase 1 and phase 2 metabolism, the products of which may exert undesirable side effects, such as estrogenicity.

Considering that daily oral dosing with XP at 30 mg/kg body weight resulted in a steady-state plasma concentration that was not significantly different from the steady-state plasma concentration of XN following oral administration at twice the daily dose, the comparison indicates that either the bioavailability of XP is higher than that of XN or that XP has a smaller clearance rate than XN, or both. The greater bioavailability and/or smaller clearance rate give XP favorable pharmacokinetic properties compared to XN. Moreover, the absence of XN's α,β-unsaturated keto functionality in XP renders XP devoid of undesirable covalent reactivity towards proteins and nucleic acids.

Figure 15B:
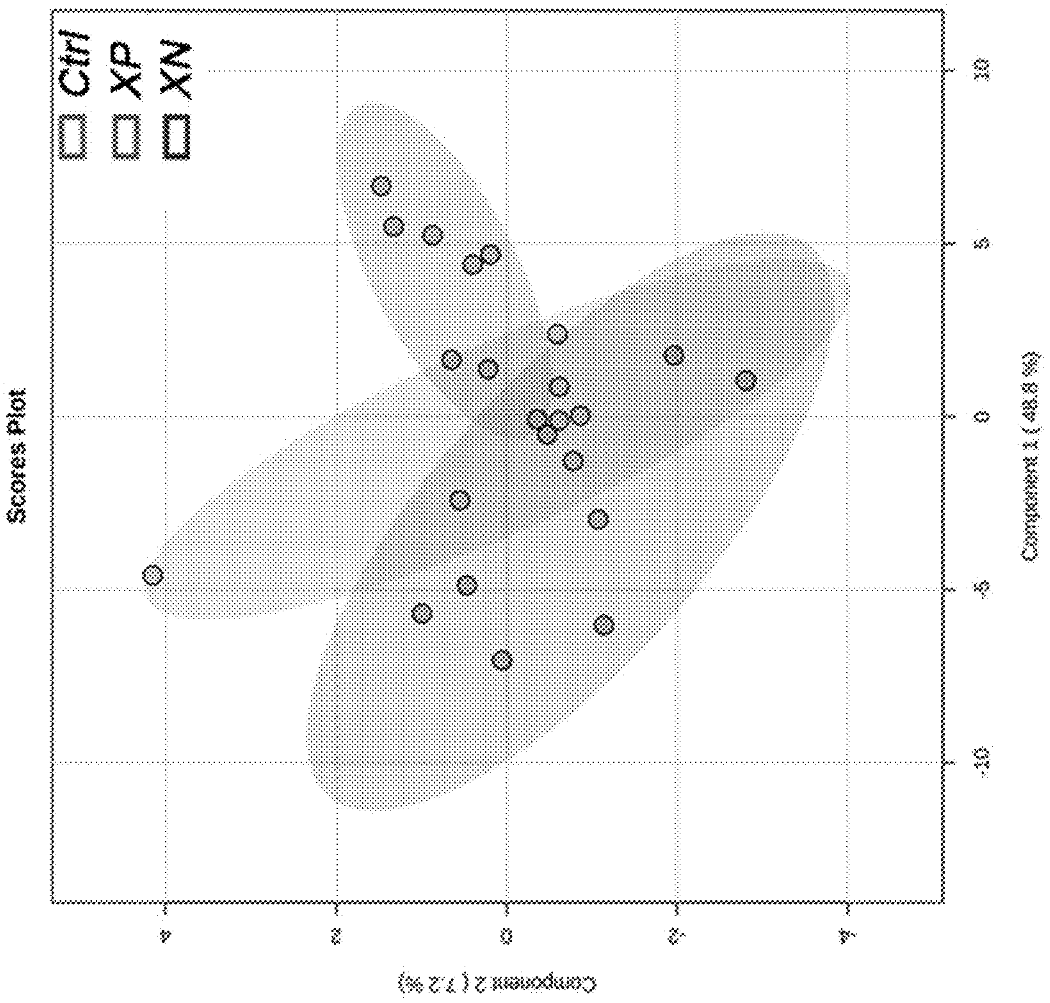
FIG. 15B is a scores plot for 4-(5-(4-hydroxyphenyl)-1-methyl-1H-pyrazol-3-yl)-5-methoxy-2-(3-methylbut-2-en-1-yl)benzene-1,3-diol or xanthohumol relative to control.
Figure 20A:
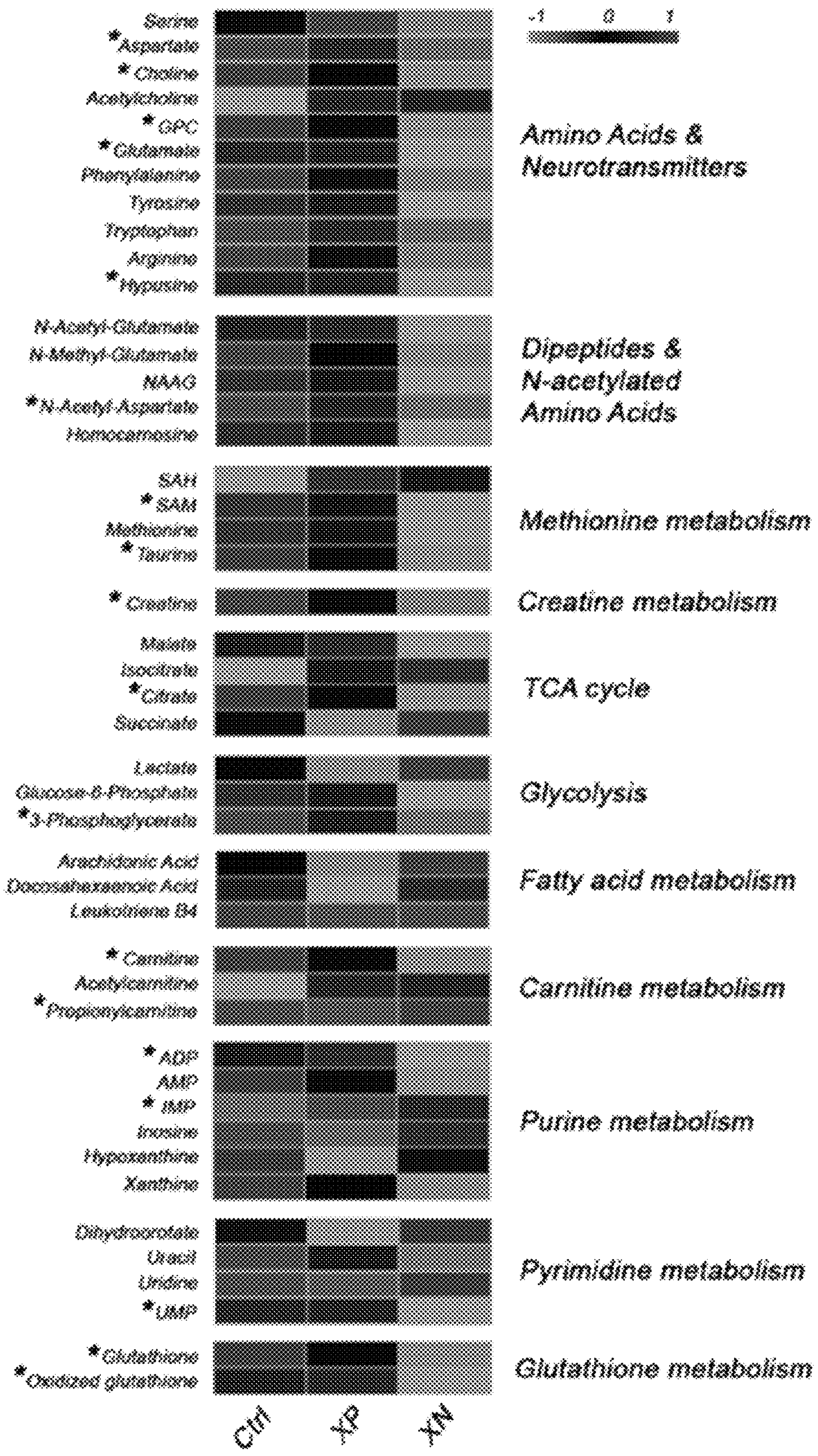
FIG. 20A provides a heat map of relative abundances of individual metabolites in the cortex of HFD-fed mice treated with XP or XN. Abbreviations: ADP: adenosine diphosphate; AMP: adenosine monophosphate; ATP: adenosine triphosphate; HETE: hydroxy-eicosatetraenoic acid; IMP: inosine monophosphate; GPC: glycerophosphocholine; NAAG: N-acetylaspartyl-glutamate; SAM: S-adenosyl-methionine; SAH: S-adenosyl-homocysteine; and UMP: uridine monophosphate.
Figure 20C:
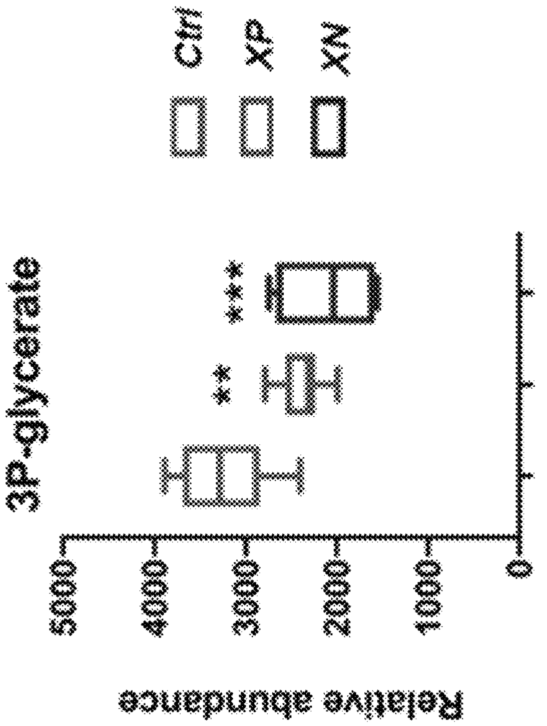
FIG. 20C is a graph illustrating relative abundance of 3-phospho-glycerate in the cortex of HFD-fed mice treated with XP or XN, with data displayed as mean±SEM, and significant differences marked as *$p<0.05$, $p<0.01$, and *$p<0.001$ for effect of treatment, one-way ANOVA.
Figure 20B:
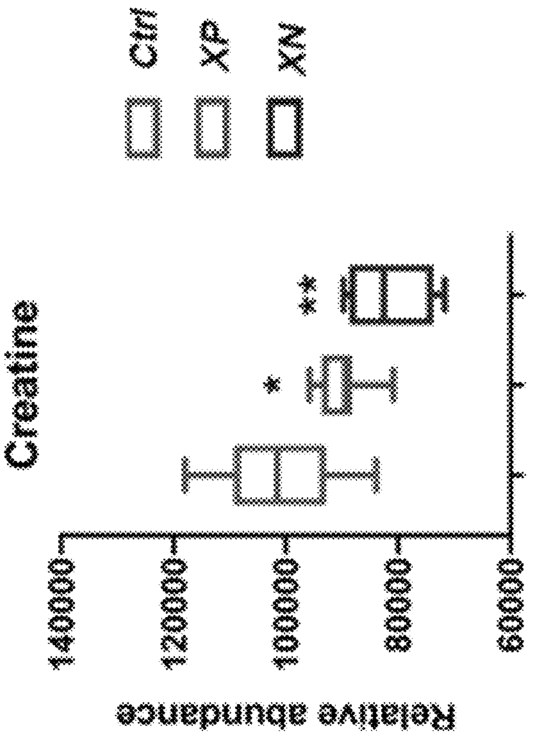
FIG. 20B is a graph illustrating relative abundance of creatinine in the cortex of HFD-fed mice treated with XP or XN, with data displayed as mean±SEM, and significant differences marked as *$p<0.05$, $p<0.01$, and *$p<0.001$ for effect of treatment, one-way ANOVA.
Figure 20E:
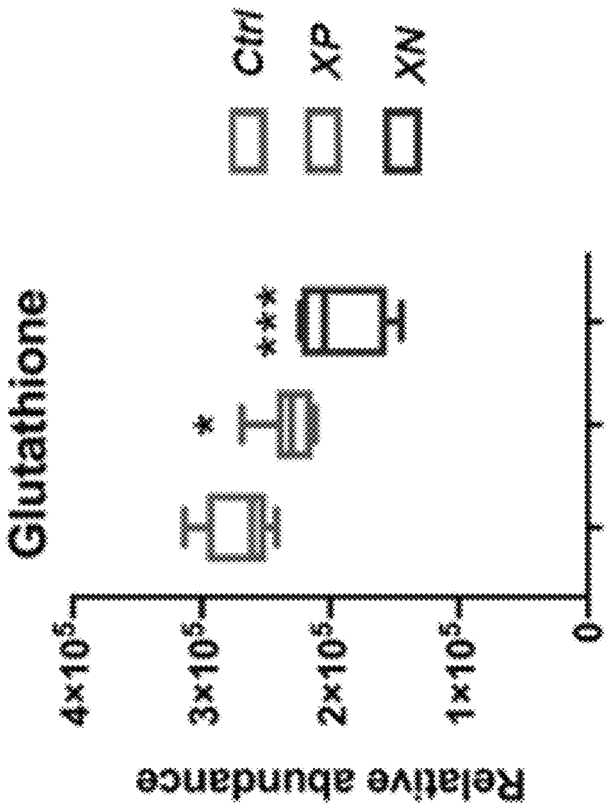
FIG. 20E is a graph illustrating relative abundance of glutathione in the cortex of HFD-fed mice treated with XP or XN, with data displayed as mean±SEM, and significant differences marked as *$p<0.05$, $p<0.01$, and *$p<0.001$ for effect of treatment, one-way ANOVA.
Figure 20D:
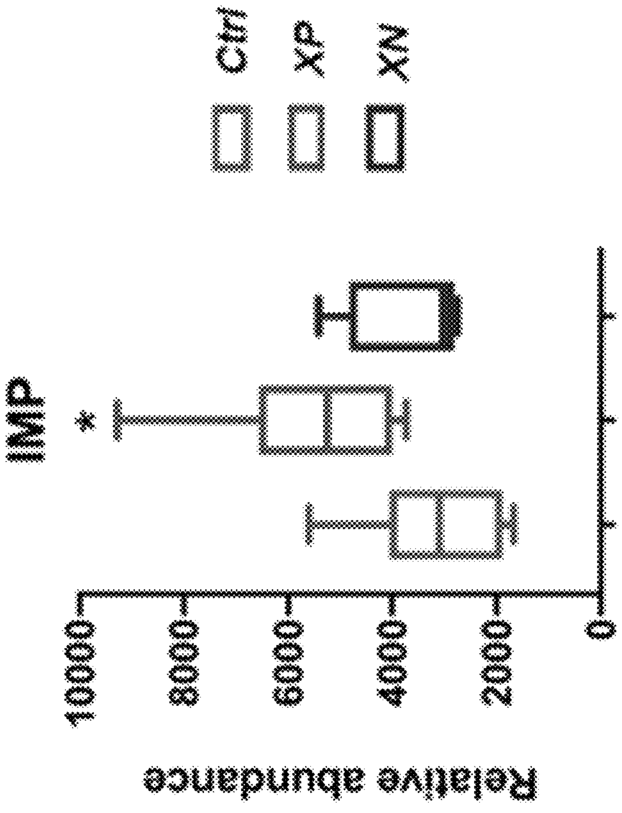
FIG. 20D is a graph illustrating relative abundance of IMP in the cortex of HFD-fed mice treated with XP or XN, with data displayed as mean±SEM, and significant differences marked as *$p<0.05$, $p<0.01$, and *$p<0.001$ for effect of treatment, one-way ANOVA.
Figure 21B:
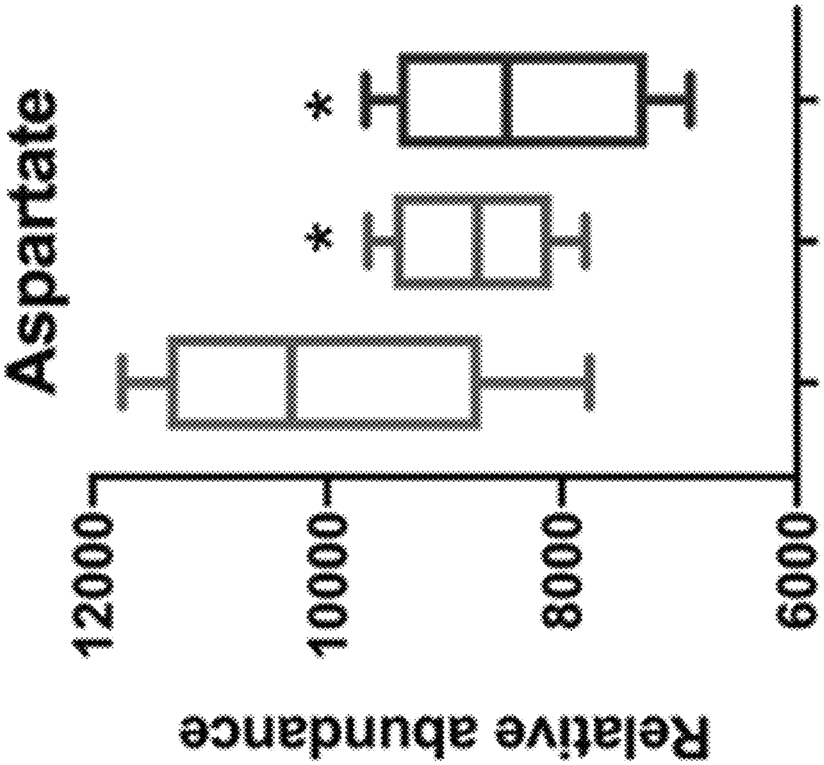
Figure 21A:
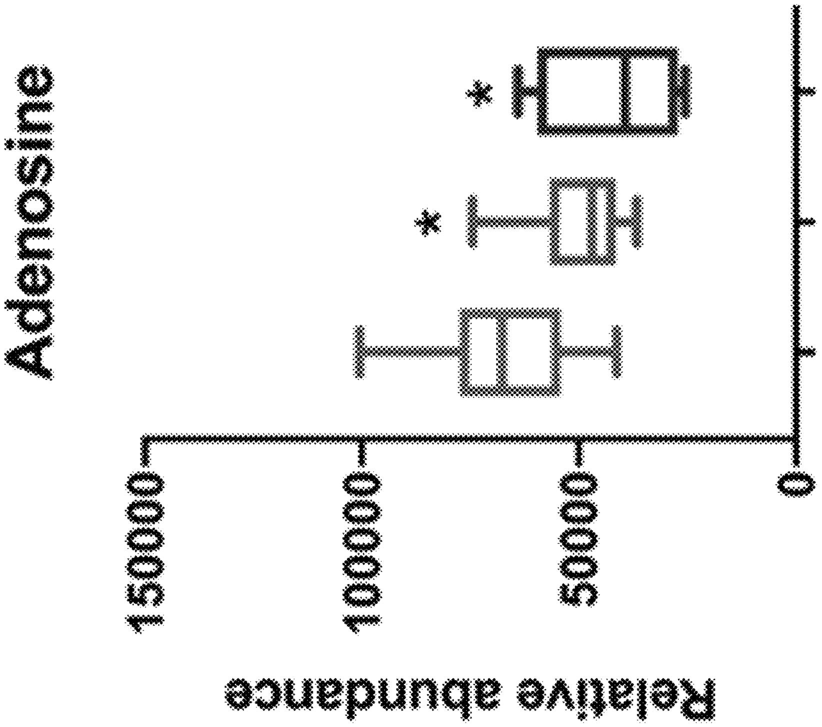
Figure 21D:
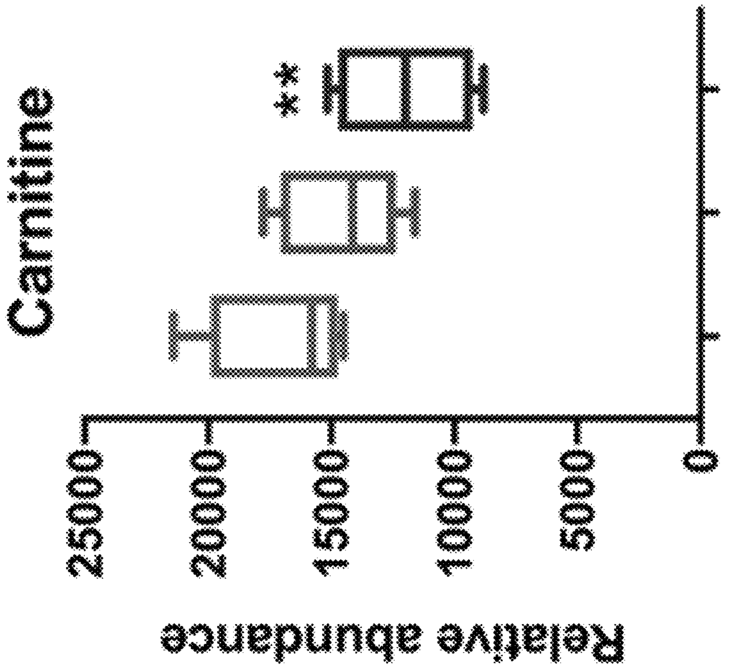
Figure 21C:
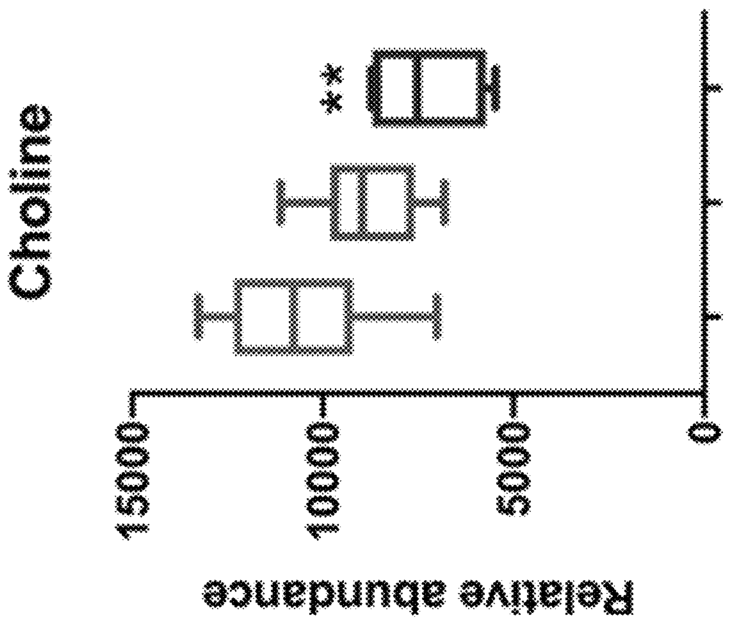
Figure 21F:
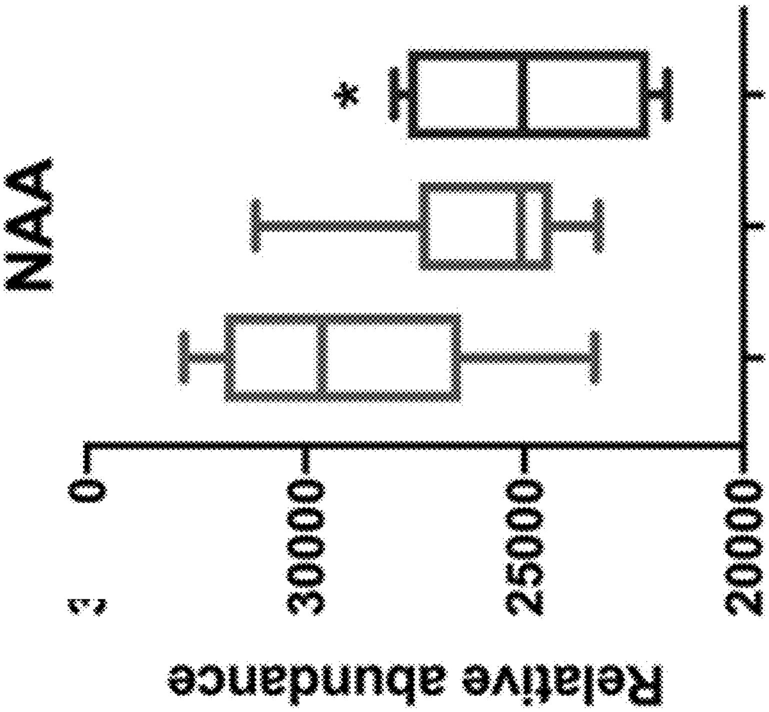
Figure 21E:
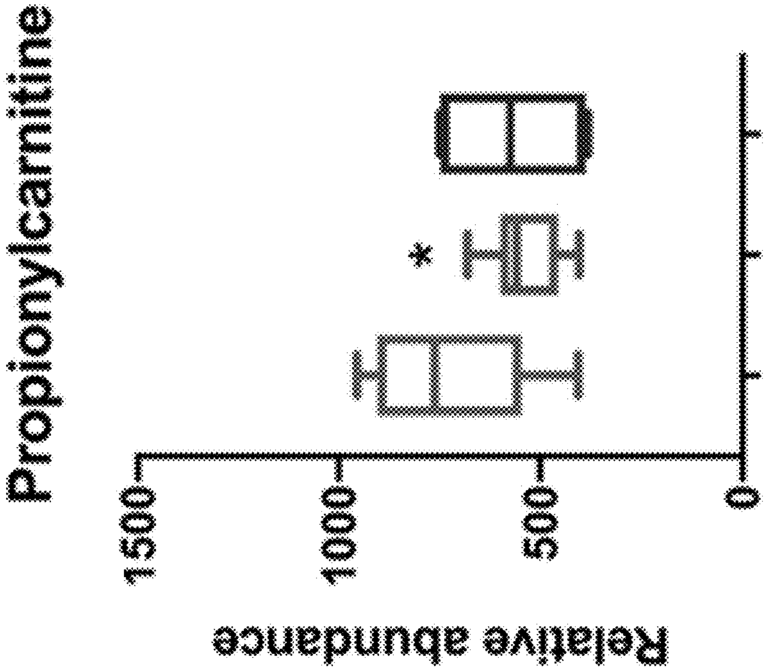
Figure 21G:
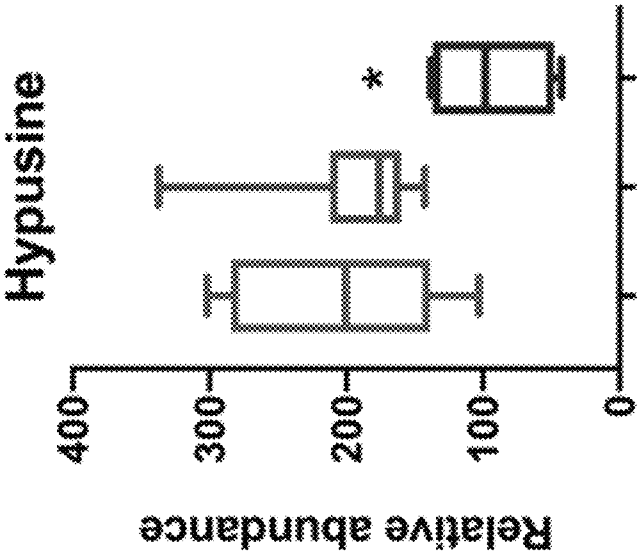
Figure 21H:
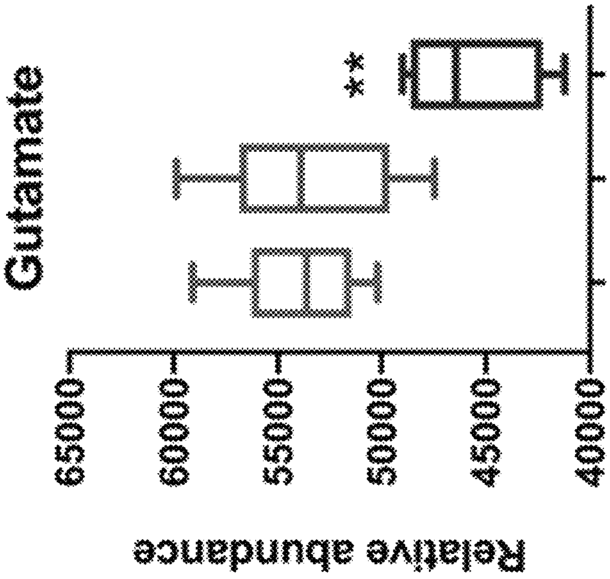
Figure 21I:
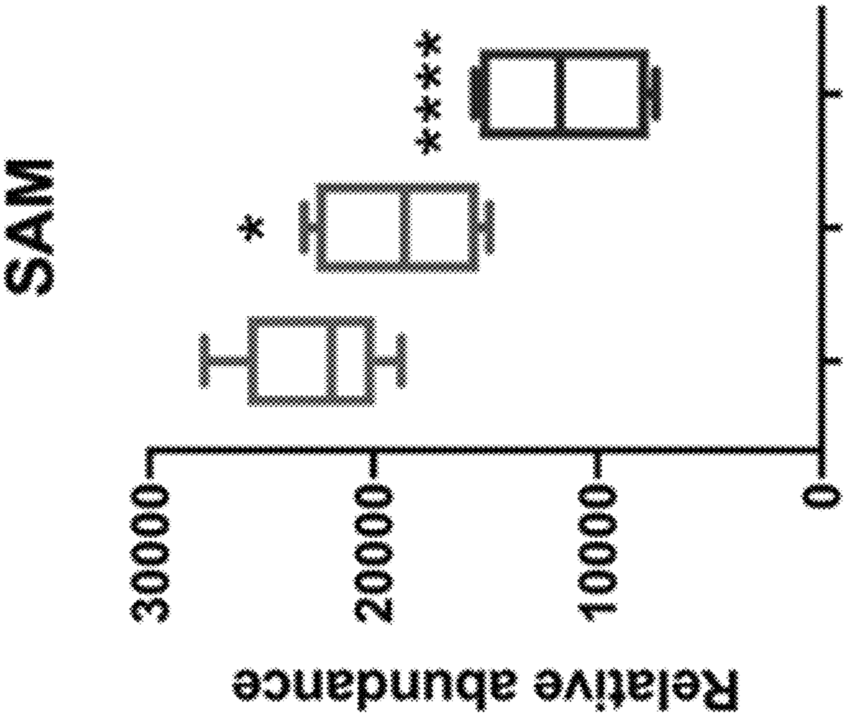
Figure 21J:
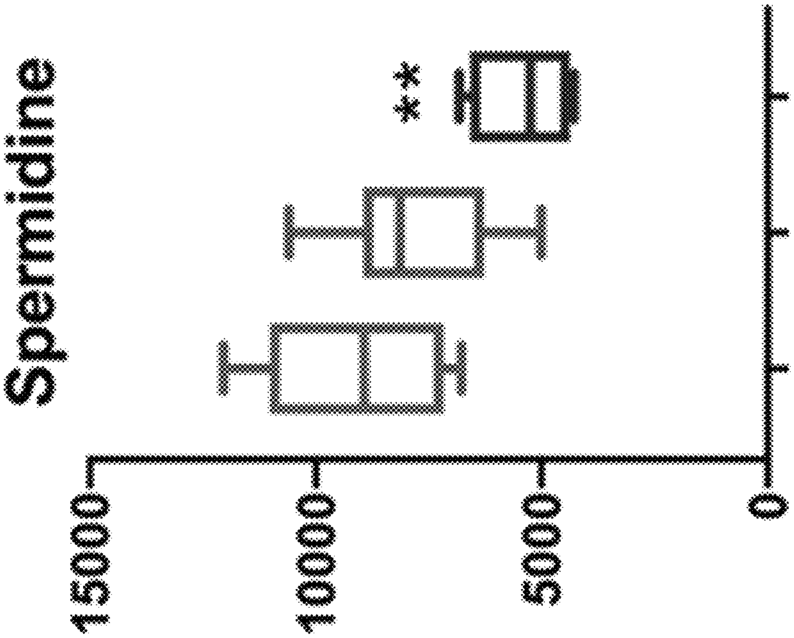
Figure 21L:
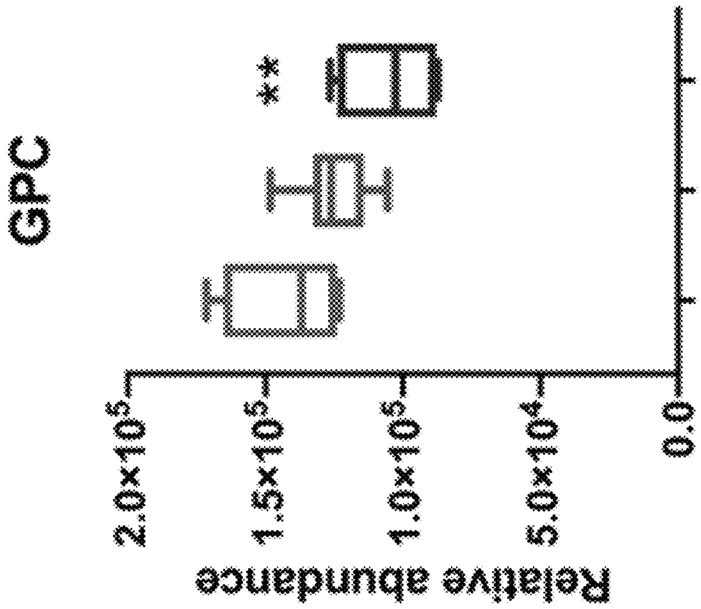
Figure 21K:
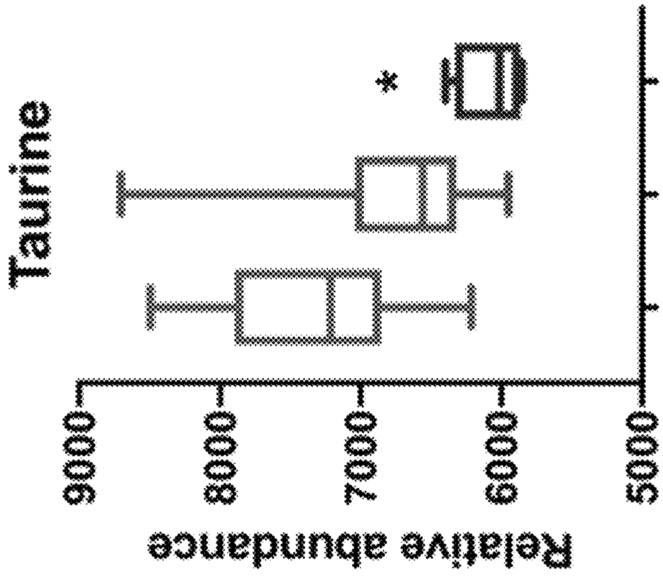
Figures 21M, 21N, 21O:
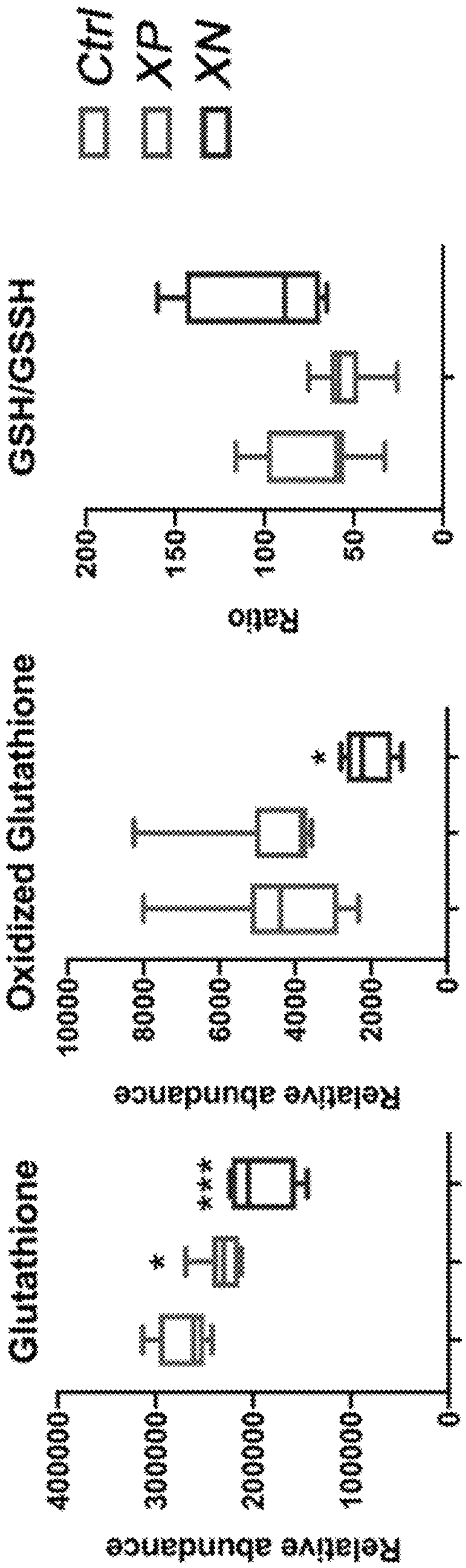
Figure 22A:
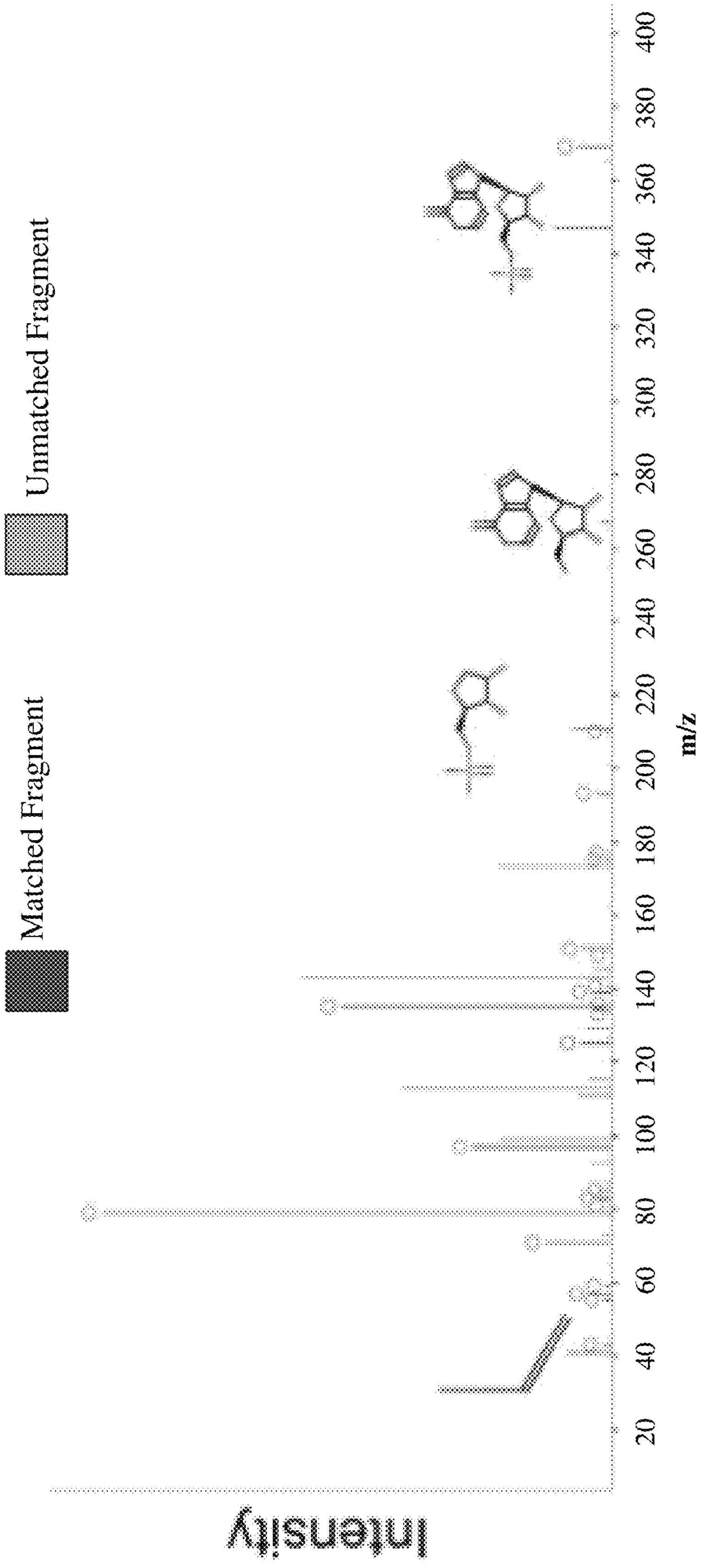
FIGS. 22A-22B are MS/MS spectrum of IMP from the QC of (A) cortex, and (B) plasma samples, where red fragments represent fragments from the library matched against the experimental data, and grey fragments are unmatched fragments.
Figure 22B:
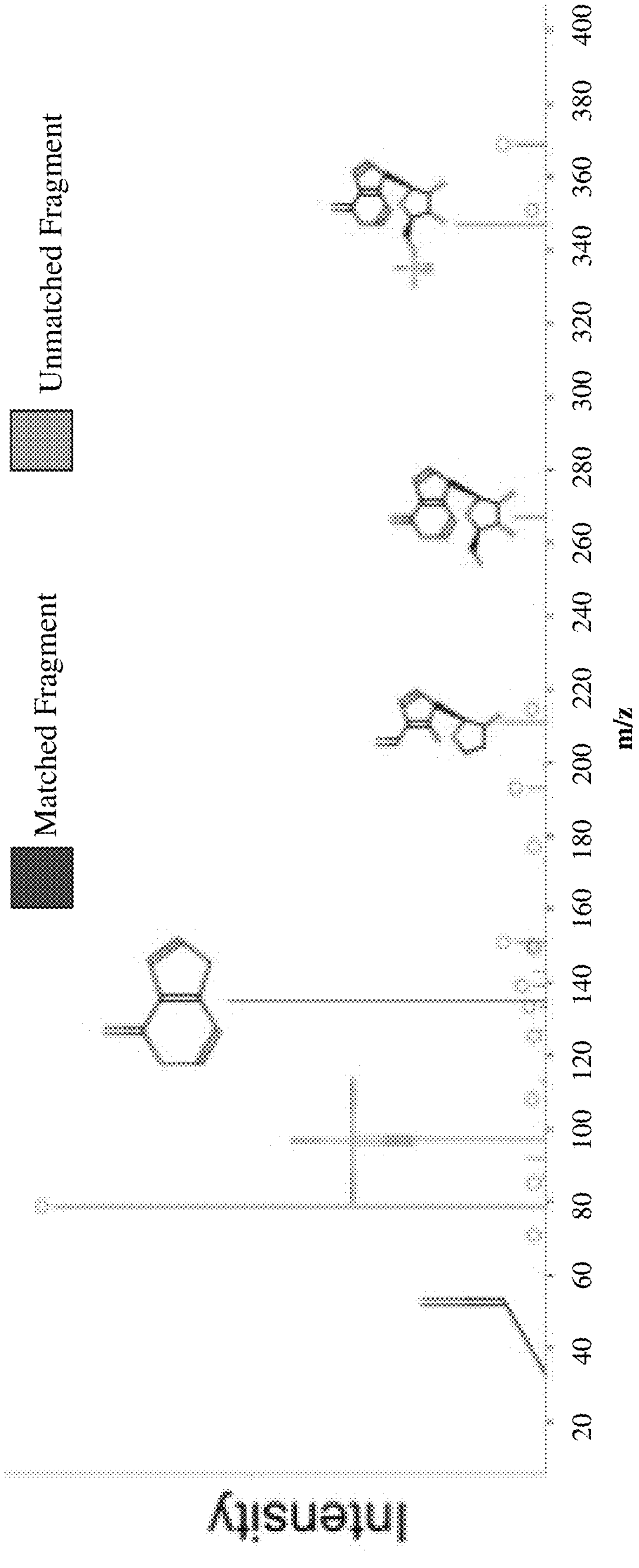
Figure 23A:
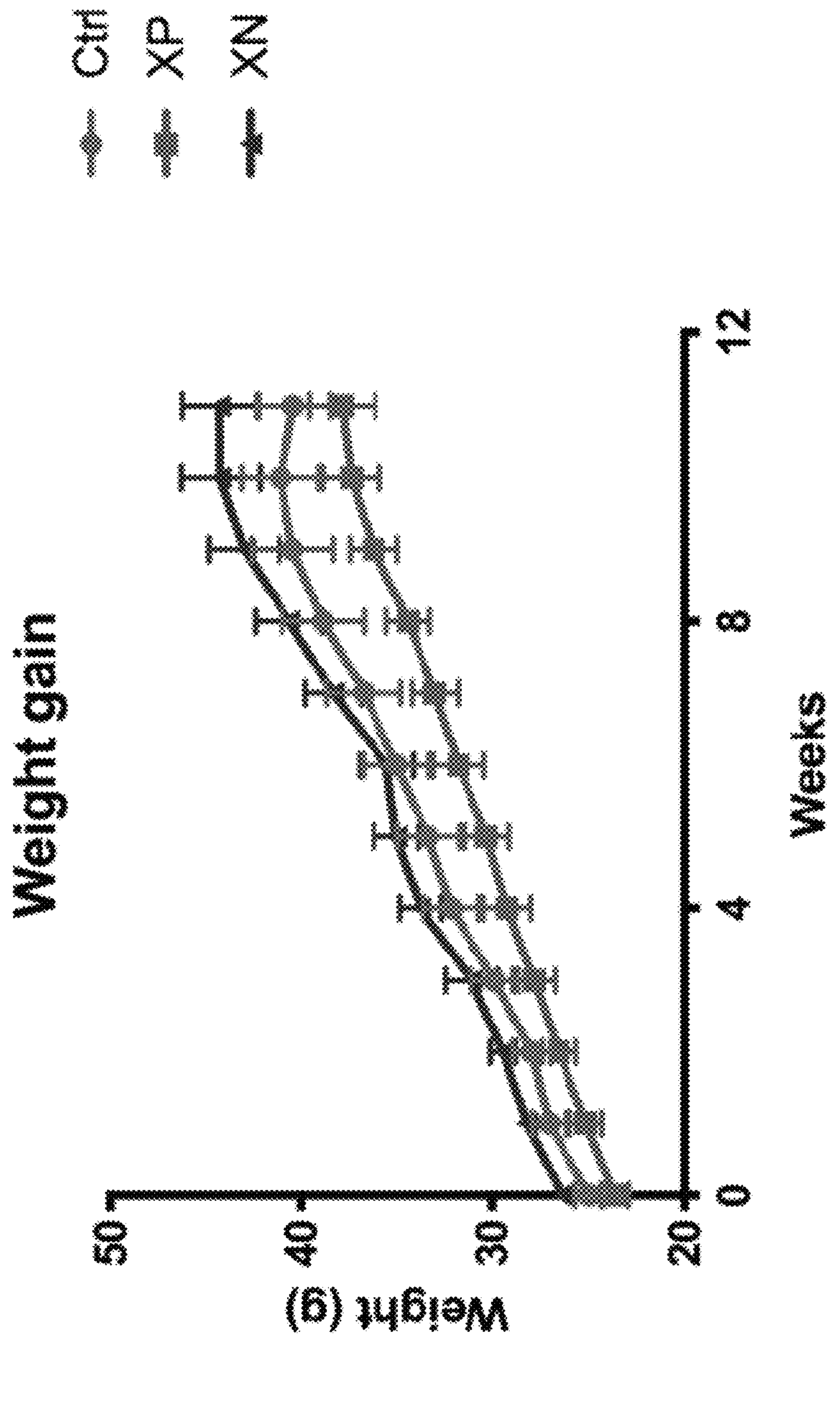
FIG. 23A is a graph of weight (g) versus time (weeks) illustrating weekly weight of HFD-fed mice untreated and treated with XP or XN relative to control, where data is represented as mean±SEM (n=4-8), no statistically significant differences, one-way ANOVA.
Figure 23B:
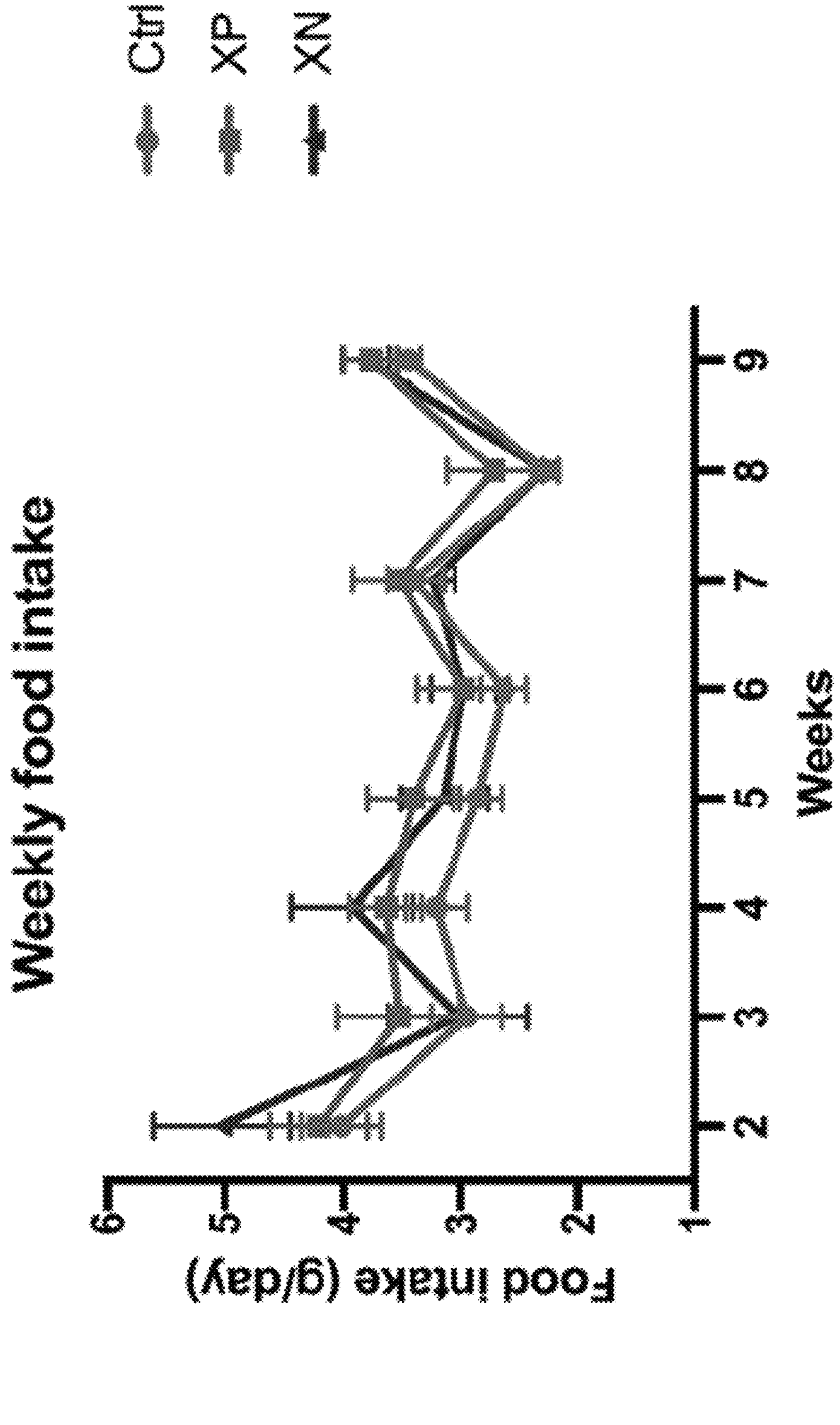
FIG. 23B is a graph of food intake (g/day) versus time (weeks) illustrating food intake of HFD-fed mice untreated and treated with XP or XN relative to control, where data is represented as mean±SEM (n=4-8), no statistically significant differences, one-way ANOVA.

8. Effect of 4-(5-(4-hydroxyphenyl)-1-methyl-1h-pyrazol-3-yl)-5-methoxy-2-(3-methylbut-2-en-1-yl) benzene-1,3-diol on Cortex Metabolites in HFD-Fed Mice An untargeted cortex metabolomics analysis was performed to gain insight into metabolic changes linked to the XP effect on locomotor activity (FIG. 15B, Table 4, below). Unexpectedly, in the cortex, XN had the most significant effect on the metabolome, and the most annotated features were decreased (FIG. 20A). Metabolites significantly decreased in both treatment groups including S-adenosylmethionine (SAM), creatine, 3-phosphoglycerate, reduced glutathione (GSH), and neurotransmitters such as aspartate (FIGS. 20A-E). Neurotransmitters such as dopamine and norepinephrine, known for their involvement in locomotor activity, were not detected using our untargeted metabolomics method. Other metabolites including N-acetyl-aspartate (NAA), choline, carnitine, and oxidized glutathione (GSSG) were also decreased in XN-treated mice. There were no significant changes in the GSH/GSSG ratio between the control and treatment groups (FIG. 21). Among the metabolites affected by XP, but not XN treatment, IMP was the only metabolite significantly increased in XP-treated mice (p=0.006, FIG. 22). This observation was especially striking as the 76% increase in cortical IMP was inconsistent with the IMP decrease observed in the plasma, suggesting that IMP might be involved in the central effects of XP on locomotor activity.

VI. Discussion of Biological Results

The biological activity of a representative pyrazole derivative of xanthohumol, 4-(5-(4-hydroxyphenyl)-1-methyl-1h-pyrazol-3-yl)-5-methoxy-2-(3-methylbut-2-en-1-yl)benzene-1,3-diol, that cannot be converted into the estrogenic metabolite, 8-prenylnaringenin, is presented herein. 4-(5-(4-hydroxyphenyl)-1-methyl-1h-pyrazol-3-yl)-5-methoxy-2-(3-methylbut-2-en-1-yl)benzene-1,3-diol improved markers of peripheral metabolism in HFD-fed mice without inducing liver toxicity, as indicated by hepatic AST and ALT concentrations. 4-(5-(4-hydroxyphenyl)-1-methyl-1h-pyrazol-3-yl)-5-methoxy-2-(3-methylbut-2-en-1-yl)benzene-1,3-diol reduced body weight gain, feed efficiency, and improved HFD-induced insulin resistance, more efficiently than xanthohumol. In the follow-up study of Example 8, 4-(5-(4-hydroxyphenyl)-1-methyl-1h-pyrazol-3-yl)-5-methoxy-2-(3-methylbut-2-en-1-yl)benzene-1,3-diol, administered orally after 4 weeks of pre-conditioning on the HFD to develop an obesity phenotype, caused significant weight gain attenuation. The weight gain decrease averaged to 5% between 9 and 12 weeks of treatment compared to HFD feeding without the investigational compound. A loss of body weight was not expected as mice, unlike humans, gain weight during their entire lifetime.

Insulin resistance is a requirement for the development of type 2 diabetes, which is closely linked to obesity (Kahn, B. B., Flier, J. S., Obesity and Insulin Resistance. The Journal of Clinical Investigation 2000, 106, 473-481). Increased release of cytokines, such as the tumor necrosis factor-α (TNF-α), IL-6 and MCP-1, might also have a role in the development of insulin resistance (Kahn, S. E., Hull, R. L., Utzschneider, K. M., Mechanisms linking obesity to insulin resistance and type 2 diabetes. Nature 2006, 444, 840-846). 4-(5-(4-hydroxyphenyl)-1-methyl-1h-pyrazol-3-yl)-5-methoxy-2-(3-methylbut-2-en-1-yl)benzene-1,3-diol decreased HOMA-IR index and improved the body's response to insulin following a sudden increase in glucose as assessed by the GTT.

Xanthohumol-mediated weight reduction might be partially due to xanthohumol being a mitochondrial uncoupler (Miranda, C. L., Elias, V. D., Hay, J. J., Choi, J., Reed, R. L., Stevens, J. F. Xanthohumol improves dysfunctional glucose and lipid metabolism in diet-induced obese C57BL/6J mice. Archives of biochemistry and biophysics 2016, 599, 22-30; Miranda, C. L., Johnson, L. A., de Montgolfier, O., Elias, V. D., et al., Non-estrogenic Xanthohumol Derivatives Mitigate Insulin Resistance and Cognitive Impairment in High-Fat Diet-induced Obese Mice. Sci Rep 2018, 8, 613). By acting as a protonophore dissipating the proton gradient necessary for ATP synthesis, xanthohumol reduces efficiency of the oxidative phosphorylation. In fact, endogenous mitochondrial uncoupling proteins (UCPs) are involved in various physiological processes including thermogenesis, autophagy, mitophagy, reactive oxygen species production and protein secretion (Demine, S., Renard, P., Arnould, T., Mitochondrial Uncoupling: A Key Controller of Biological Processes in Physiology and Diseases. Cells 2019, 8, 79528). Moreover, free fatty acids (FFAs) are a major class of natural uncouplers of oxidative phosphorylation in mitochondria (Wojtczak, L., Schonfeld, P., Effect of fatty acids on energy coupling processes in mitochondria. Biochim Biophys Acta 1993, 1183, 41-57). Therefore, mitochondrial uncoupling has been proposed as a mechanism to treat several human diseases, such as obesity and cardiovascular diseases (Demine S., et al. vide, supra). Data presented herein reveals an increase in respiratory rate and energy expenditure in 4-(5-(4-hydroxyphenyl)-1-methyl-1h-pyrazol-3-yl)-5-methoxy-2-(3-methylbut-2-en-1-yl)benzene-1,3-diol-treated C57BL/6J mice, supporting the mitochondrial uncoupling properties of the flavonoid in vivo. Moreover, respiratory rate and energy expenditure were higher in 4-(5-(4-hydroxyphenyl)-1-methyl-1h-pyrazol-3-yl)-5-methoxy-2-(3-methylbut-2-en-1-yl)benzene-1,3-diol-treated mice than in xanthohumol-treated mice. The enhanced energy expenditure observed in 4-(5-(4-hydroxyphenyl)-1-methyl-1h-pyrazol-3-yl)-5-methoxy-2-(3-methylbut-2-en-1-yl)benzene-1,3-diol-treated mice is likely due to the increase in locomotor activity. Similar induction of motor behavior has been consistently associated with the administration of dopamine agonists such as apomorphine and haloperidol. Low doses of the antipsychotic haloperidol (less than 0.1 mg/kg) induce a progressive increase in locomotor response, which has been interpreted as a result of the blockade of presynaptic auto-receptors that results in the dopamine levels rising, leading to increase in locomotor activity. The results presented herein indicate that 4-(5-(4-hydroxyphenyl)-1-methyl-1h-pyrazol-3-yl)-5-methoxy-2-(3-methylbut-2-en-1-yl)benzene-1,3-diol has a central mechanism of action, in addition to the mitochondrial uncoupling effect.

4-(5-(4-hydroxyphenyl)-1-methyl-1h-pyrazol-3-yl)-5-methoxy-2-(3-methylbut-2-en-1-yl)benzene-1,3-diol did not display liver cell toxicity in the range 1-50 μM, suggesting that the compound may not cause liver damage in mice receiving test compounds at a dose of 60 mg/kg/day or in humans at an equivalent dose of 350 mg/day for a 70 kg person.

Disclosed derivatives of xanthohumol, such as 4-(5-(4-hydroxyphenyl)-1-methyl-1h-pyrazol-3-yl)-5-methoxy-2-(3-methylbut-2-en-1-yl)benzene-1,3-diol, improve HFD-induced metabolic dysfunction and are safe at doses of 30 mg/kg/day in C57BL/6J mice. Similar to xanthohumol, 4-(5-(4-hydroxyphenyl)-1-methyl-1h-pyrazol-3-yl)-5-methoxy-2-(3-methylbut-2-en-1-yl)benzene-1,3-diol likely acts as a mitochondrial uncoupler to impair ATP synthesis and increase energy expenditure. Pyrazole derivatives of xanthohumol, such as 4-(5-(4-hydroxyphenyl)-1-methyl-1h-pyrazol-3-yl)-5-methoxy-2-(3-methylbut-2-en-1-yl)benzene-1,3-diol, represent a promising alternative for the treatment of obesity-related metabolic impairments.

XN is known to have beneficial effects on obesity. However, due to its poor bioavailability and extensive metabolism, the clinical applications of XN remain limited. The low biological efficacy of XN native extracts administered orally, and stable derivatives of XN were shown to be more potent in vivo. Several factors might contribute to the discrepancies in XN-induced weight loss as presented herein in comparison to previous reports. Under the same feeding and housing conditions, some animals are more prone to develop obesity, and these phenotypic pharmacodynamics of XN. Moreover, recently published data shows that XN requires the intestinal microbiota to improve glucose metabolism in diet-induced obese mice, suggesting that gut microbiota composition is another potential variable.

Certain disclosed embodiments concern the assessed biological activity of XP, a pyrazole derivative of XN that cannot be converted to 8-PN. XP improved metabolic markers in HFD-fed mice without inducing liver toxicity, as indicated by hepatic AST and ALT concentrations. XP reduced body weight gain, feed efficiency, and improved HFD-induced insulin resistance. Insulin resistance is a requirement for the development of type 2 diabetes, which is closely linked to obesity. Increased release of cytokines such as tumor necrosis factor-α, IL-6, and MCP-1 might also have a role in the development of insulin resistance. No significant changes were observed in cytokine levels in vivo, but XP improved the animals' response to insulin secretion following a sudden increase in glucose as assessed by the GTT and the decreased HOMA-IR index.

XN-mediated weight reduction may be partially due to XN being a mitochondrial uncoupler. By acting as a protonophore dissipating the proton gradient necessary for ATP synthesis, XN reduces the efficiency of the oxidative phosphorylation. In fact, endogenous mitochondrial UCPs dissipate the proton gradient and are involved in various physiological processes including thermogenesis autophagy, mitophagy, reactive oxygen species (ROS) production, and protein secretion. Therefore, mitochondrial uncoupling has been proposed as a mechanism to treat several human diseases, such as obesity and cardiovascular diseases. XN depolarizes the mitochondrial membrane, which is associated with an increase in respiratory rate and EE in XN-treated C57BL/6J mice, independent from UCP1 protein expression. These data support that XN mitochondrial uncoupling properties are due to proton translocation by the flavonoid across the mitochondrial inner membrane. UCP1 protein expression in WAT was lower in XN-treated mice, contrary to previous reports of browning of white adipocytes by XN in vitro. This suggests a compensatory regulation of UCP levels in vivo to prevent complete impairment of the mitochondrial respiration.

Although the protonophore effect of XP in vitro was comparable to XN, daily EE was higher in XP-treated mice than in XN-treated mice. The marked increase in EE in XP-treated mice was, at least partially, due to the increase in locomotor activity. In fact, daily EE consists of the basal metabolic rate, diet-induced thermogenesis, and energy cost of physical activity. During physical activity, EE matches the sum of heat loss and work output. As both thermogenesis and physical activity contribute to EE, we observed higher EE in XP-treated mice, with up to 27% increase in daily EE compared to control mice. An induction in motor behavior, similar to that observed in XP-treated mice, is associated with the administration of dopamine agonists such as haloperidol. Haloperidol induces an increase in locomotor response as a result of the blockade of presynaptic autoreceptors, which disrupts negative feedback and increases release of dopamine. Several compounds with thermogenic and fat-oxidizing potentials also possess sympathomimetic stimulatory activity. Higher IMP levels were observed in the cortex of XP-treated mice, which might be related to the changes in motor behavior. In fact, inosine and inosine metabolites including IMP activate adenosine receptors such as adenosine 2A receptor (A2AR) and stimulate A2AR-mediated intracellular cAMP production. The activation of adenosine receptors is known to induce anxiolytic effects in mice and A2AR mediates psychostimulant-mediated effects on locomotor activity. IMP also has a central effect on mood and behavior in mice by reversing HFD-induced excess in neuronal NO synthase in the cerebellum. These reports combined with data presented herein establish the involvement of IMP in increased locomotor activity in XP-treated mice. A dual mechanism involving direct and indirect mitochondrial uncoupling appears is responsible for XP-mediated increase in EE in HFD-fed mice.

Untargeted metabolomics suggested that XP and XN influence cellular energy metabolism in HFD-fed mice, leading to decreased purine metabolites and creatine in the plasma. Purine metabolism consists of de novo synthesis, catabolism, and salvage pathways, and purine molecules form the scaffold of the key molecule for storing cellular energy. Although mitochondrial and glycolytic pathways are used to produce energy, instantaneous energy needs are satisfied through the phosphocreatine shuttle and the combined efforts of AMP deaminase (AMPD), AMP-activated protein kinase (AMPK), and adenylate kinase (ADK). These enzymes regulate AMP conversion to IMP to keep AMP levels low during times of high ATP utilization and to favor the production of ATP and AMP from two ADPs. IMP may then be degraded to inosine and then to hypoxanthine and potentially further degraded to xanthine and uric acid.

Several mechanisms might explain the decrease in purine metabolites observed in treated mice. First, the downregulation of the purine degradation pathway by XP and XN may reflect a decrease in oxidative stress. In fact, purine degradation is regulated by oxidative stress, and increased purine degradation serves as an indication of an increased inflammatory response. In inflammatory diseases such as periodontitis, purine metabolites are significantly increased at the disease sites. This hypothesis is further supported by the notion that other metabolites associated with oxidative stress such as 12-HETE in the plasma and glutathione metabolites in the brain were decreased by XP and XN. GSH scavenges ROS and reactive nitrogen species to protect cells from oxidative stress. Obesity has been associated with a decrease in GSH in the liver and kidney, but GSH was shown to be increased in cardiac tissues of obese rats in an effort to protect cells against oxidative damage. Moreover, there is evidence that under the right conditions, GSH depletion and ROS may prevent type 2 diabetes. The decreased abundances of both GSH and GSSG in the cortex of treated mice might indicate decreased oxidative stress in the brain of XP- and XN-treated mice. Second, the downregulation of plasma purine metabolites may be secondary to mitochondrial uncoupling and increased EE in XP-treated and XN-treated mice. Purine metabolite concentrations fluctuate with physical activity and acute muscular exercise results in increased plasma hypoxanthine levels. Paradoxically, long-lasting exercise and endurance training cause a decrease in pre- and post-exercise plasma hypoxanthine concentrations in periods of specific preparation and competition in male athletes. The constant mitochondrial uncoupling induced by chronic administration of XP and XN leads to enhanced consumption of fatty acids, sugars, and proteins to make ATP, creating a situation that could be comparable to mild endurance training.

Previous studies have shown that XN is detected in the brain of XN-treated mice. Similar to XN, XP was measured in the cortex of treated mice and the compounds might cross the BBB as aglycones. UDP-glucuronosyltransferases (UGTs) such as UGT1a6a and UGT2b35 have been identified in mouse brain and might mediate the glucuronidation of xenobiotics in the brain. Together, these results demonstrate that XP improved HFD-induced metabolic dysfunction, increased EE, and locomotor activity in HFD-fed mice. XP did not cause liver damage in mice administered the compound at a dose of 30 mg/kg body weight/day, which is equivalent to a dose of 175 mg/day in a 70 kg person. As managing obesity by stimulating thermogenesis and EE remains a promising concept in the search of potent anti-obesity agents, XP is a safe and promising option for treating obesity-related metabolic impairments.

VI. Examples

The following examples are provided to illustrate certain features of the present invention. A person of ordinary skill in the art will appreciate that the scope of the invention is not limited to the particular features exemplified by these Examples.

Example 1

This example describes synthesis of 4-(5-(4-hydroxyphenyl)-1-methyl-4,5-dihydro-1H-pyrazol-3-yl)-5-methoxy-2-(3-methylbut-2-en-1-yl)benzene-1,3-diol, compound 1, Scheme 1. A stirred solution of xanthohumol (2.00 g, 5.64 mmol) in DMSO (45 mL) at room temperature was treated with methylhydrazine (2.97 mL, d=0.875, 2.60 g, 56.0 mmol, 10 equivalents). The resulting red mixture was heated to 75° C. and stirred for 15 hours. After this time, the reaction mixture was cooled to room temperature and partitioned between saturated aqueous $NH_4Cl$ (100 mL) and EtOAc (100 mL). The layers were separated, and the aqueous layer was extracted with EtOAc (4×70 mL). The combined organic phases were washed with $H_2O$ (2×100 mL), dried ($Na_2SO_4$), and concentrated in vacuo. The residue was purified by column chromatography ($SiO_2$, eluting with 40% EtOAc in hexanes) to afford pyrazoline 1 (1.65 g, 4.32 mmol, 77%) as a beige solid: IR (neat) 3351, 2919, 1614, 1517, 1448, 1346, 1211, 1103 $cm^{-1}$; $^1H$ NMR (700 MHz, $d_6$-DMSO) δ 12.32 (1H, s), 9.68 (1H, s), 9.41 (1H, s), 7.25 (2H, d, J=8.1 Hz), 6.75 (2H, d, J=8.2 Hz), 6.02 (1H, s), 5.15 (1H, t, J=6.5 Hz), 3.82 (1H, dd, J=14.5, 9.5 Hz), 3.67 (1H, dd, J=17.3, 9.5 Hz), 3.65 (3H, s), 3.16 (2H, d, J=6.8 Hz), 2.96 (1H, dd, J=17.3, 14.5 Hz), 2.60 (3H, s), 1.70 (3H, s), 1.60 (3H, s) ppm; $^{13}C$ NMR (175 MHz, $d_6$-DMSO) δ 157.8 (0), 157.1 (0), 157.0 (0), 156.8 (0), 152.9 (0), 129.6 (0), 129.4 (0), 128.7 (2C, 1), 123.6 (1), 115.2 (2C, 1), 107.2 (0), 98.2 (0), 90.7 (1), 71.3 (1), 55.3 (3), 46.9 (2), 41.5 (3), 25.5 (3), 21.5 (2), 17.7 (3) ppm; MS (ES+) m/z 383 (M+H)+; HRMS (ES+) m/z 383.1981 (calcd. for $C_{22}H_{27}N_2O_4$: 383.1971).

Example 2

This example describes the synthesis of 1-acetoxy-3-hydroxy-4-[5-(4-acetoxyphenyl)-1-methyl-4,5-dihydro-1H-pyrazol-3-yl]-5-methoxy-2-(3-methylbuten-1-yl)benzene, compound 2, Scheme 1. A stirred suspension of the phenolic pyrazoline 1 (1.64 g, 4.29 mmol) in $CH_2Cl_2$ (30 mL) at room temperature was treated with triethylamine (5.36 mL, d=0.726, 3.89 g, 38.4 mmol, 9 equivalents) and acetic anhydride (1.62 mL, d=1.08, 1.75 g, 17.1 mmol, 4 equivalents). The resulting red suspension was stirred at room temperature for 15 hours, during which time it became a yellow solution. The reaction mixture was washed with $H_2O$ (3×20 mL) and the combined aqueous phases were extracted with $CH_2Cl_2$ (2×30 mL). The combined organic phases were washed with brine (50 mL), dried ($Na_2SO_4$), and concentrated in vacuo. The residue was purified by column chromatography ($SiO_2$, eluting with 30% EtOAc in hexanes) to afford the diacetate 2 (1.78 g, 3.82 mmol, 89%) as a colorless solid: IR (neat) 2918, 1757, 1623, 1508, 1369, 1205, 133, 1054 $cm^{-1}$; $^1H$ NMR (700 MHz, $CDCl_3$) δ 12.52 (1H, br s), 7.47 (2H, d, J=7.6 Hz), 7.09 (2H, d, J=7.6 Hz), 6.12 (1H, s), 5.18 (1H, t, J=6.1 Hz), 3.96 (1H, dd, J=14.1, 10.0 Hz), 3.79 (1H, dd, J=17.4, 9.9 Hz), 3.70 (3H, s), 3.26 (2H, d, J=6.7 Hz), 3.16 (1H, dd, J=17.4, 14.2 Hz), 2.76 (3H, s), 2.32 (3H, s), 2.31 (3H, s), 1.76 (3H, s), 1.68 (3H, s) ppm; $^{13}C$ NMR (175 MHz, $CDCl_3$) δ 169.7 (0), 169.5 (0), 158.6 (0), 156.7 (0), 152.5 (0), 150.4 (2C, 0), 137.8 (0), 131.6 (0), 128.7 (2C, 1), 122.4 (1), 121.9 (2C, 1), 114.6 (0), 104.5 (0), 96.5 (1), 72.0 (1), 55.5 (3), 47.8 (2), 42.0 (3), 25.9 (3), 23.0 (2), 21.3 (3), 21.1 (3), 18.0 (3) ppm; MS (ES+) m/z 467 (M+H)+; HRMS (ES+) m/z 467.2183 (calcd. for $C_{26}H_{31}N_2O_6$: 467.2182).

Example 3

This example describes the synthesis of 1-Acetoxy-3-hydroxy-4-[5-(4-acetoxyphenyl)-1-methyl-1H-pyrazol-3-yl]-5-methoxy-2-(3-methylbuten-1-yl)benzene, compound (3), Scheme 1. A stirred solution of the pyrazoline 2 (1.45 g, 3.11 mmol) in $CH_2Cl_2$ (20 mL) at room temperature was treated with 2,3-dichloro-5,6-dicyano-1,4-benzoquinone (DDQ, 1.07 g, 4.71 mmol, 1.5 equivalents). After stirring for 90 min, a second portion of DDQ (0.213 g, 0.94 mmol, 0.3 equivalent) was added and the reaction mixture stirred for a further 15 minutes. The mixture was then filtered, and the solid filter process residue washed with EtOAc (20 mL) and $CH_2Cl_2$ (20 mL). The filtrate and washings were combined and concentrated in vacuo. The residue resulting from the evaporation process was purified by column chromatography ($SiO_2$, eluting with 30% EtOAc in hexanes) to afford the pyrazole 3 (809 mg, 1.74 mmol, 56%) as a colorless solid: IR (neat) 2922, 1757, 1622, 1368, 1198, 1108, 1064 $cm^{-1}$; $^1H$ NMR (700 MHz, $CDCl_3$) δ 12.21 (1H, br s), 7.49 (2H, d, J=8.6 Hz), 7.21 (2H, d, J=8.6 Hz), 7.00 (1H, s), 6.24 (1H, s), 5.23 (1H, tm, J=6.9 Hz), 3.90 (3H, s), 3.86 (3H, s), 3.30 (2H, d, J=6.9 Hz), 2.35 (3H, s), 2.32 (3H, s), 1.78 (3H, s), 1.68 (3H, s) ppm; $^{13}C$ NMR (175 MHz, $CDCl_3$) δ 169.7 (0), 169.5 (0), 156.6 (0), 156.3 (0), 151.1 (0), 149.1 (0), 147.6 (0), 142.9 (0), 131.3 (0), 130.3 (2C, 1), 128.0 (0), 122.8 (1), 122.2 (2C, 1), 114.5 (0), 107.9 (1), 104.4 (1), 96.7 (1), 55.7 (3), 37.5 (3), 25.9 (3), 23.2 (2), 21.3 (3), 21.2 (3), 18.0 (3) ppm; HRMS (ES+) m/z 465.2030 (calcd. for $C_{26}H_{29}N_2O_6$: 465.2026).

Example 4

This example describes the synthesis of 4-(5-(4-hydroxyphenyl)-1-methyl-1H-pyrazol-3-yl)-5-methoxy-2-(3-methylbut-2-en-1-yl)benzene-1,3-diol (4). A solution of diacetate 3 (208 mg, 0.448 mmol) in MeOH (5 mL) was treated with hydrazine hydrate (0.087 mL, d=1.030, 90 mg, 64 wt % in $N_2H_4$, 1.80 mmol, 4 equivalents) and the resulting mixture stirred for 3 hours at room temperature. The reaction mixture was then concentrated in vacuo and the residue dissolved in EtOAc (30 mL) and washed with $H_2O$ (2×20 mL). The aqueous phases were extracted with EtOAc (2×10 mL) and the combined organic phases were dried ($Na_2SO_4$) and concentrated in vacuo. The residue was purified by columns chromatography ($SiO_2$, 30% EtOAc in hexanes) to afford N-methyl pyrazole xanthohumol derivative 4 (166 mg, 0.436 mmol, 97%) as a colorless solid.

An alternative saponification method is also illustrated by Scheme 1. A solution of diacetate 3 (500 mg, 1.08 mmol) in THE (10 mL) was treated with aqueous LiOH (10 mL, 2.0 M, 20.0 mmol, 20 equivalents) and the resulting mixture stirred at room temperature for 1 hour. After this time, 5 wt. % aq. $NH_4Cl$ was added to adjust the pH to 7.0 and the biphasic system was extracted with EtOAc (5×10 mL). The combined organic extracts were dried ($Na_2SO_4$) and concentrated in vacuo. The residue was purified by column chromatography ($SiO_2$, eluting with 40% EtOAc in hexanes) to afford N-methyl pyrazole xanthohumol derivative 4 (370 mg, 0.973 mmol, 90%) as a colorless foamy solid: IR (neat) 3392, 2919, 1703, 1615, 1501, 1431, 1268, 1105, 1067 $cm^{-1}$; $^1H$ NMR (700 MHz, $d_6$-DMSO) δ 12.04 (1H, s), 9.82 (1H, br s), 9.40 (1H, br s), 7.39 (2H, d, J=7.9 Hz), 6.90 (2H, d, J=7.9 Hz), 6.79 (1H, s), 6.10 (1H, s), 5.20 (1H, t, J=6.9 Hz), 3.86 (3H, s), 3.77 (3H, s), 3.20 (2H, d, J=7.0 Hz), 1.72 (3H, s), 1.61 (3H, s) ppm; $^{13}C$ NMR (175 MHz, $CDCl_3$) δ 158.0 (0), 156.0 (0), 155.9 (0), 155.4 (0), 147.2 (0), 143.2 (0), 130.0 (2C, 1), 129.1 (0), 124.0 (1), 120.2 (0), 115.6 (2C, 1), 107.2 (0), 105.4 (1), 97.8 (0), 90.7 (1), 55.2 (3), 37.1 (3), 25.5 (3), 21.8 (2), 17.7 (3) ppm; HRMS (ES+) m/z 381.1796 (calcd. for $C_{22}H_{25}N_2O_4$: 381.1814).

Example 5

This example describes the synthesis of 4-(5-(4-hydroxyphenyl)isoxazol-3-yl)-5-methoxy-2-(3-methylbut-2-en-1-yl)benzene-1,3-diol, compound 5, Scheme 2. A stirred solution of xanthohumol (20 mg, 0.0564 mmol) in DMSO (0.5 mL) at room temperature was treated with hydroxylamine hydrochloride (37 mg, 0.532 mmol). After 10 minutes, powdered KOH (19 mg, 0.339 mmol) was added and the resulting mixture heated to 75° C. and stirred at that temperature for 15 hours. The reaction mixture was then allowed to cool to room temperature and subsequently neutralized by the addition of 5% w/w aq. $NH_4Cl$. EtOAc (5 mL) was added and the layers shaken and separated. The aqueous phase was extracted with EtOAc (2×5 mL) and the combined organic phases washed with $H_2O$ (3×10 mL). The combined aqueous washings were extracted with EtOAc (2×10 mL) and all organic phases combined, dried ($Na_2SO_4$), and concentrated in vacuo. The residue was purified by column chromatography ($SiO_2$, eluting with 40% EtOAc in hexanes) to afford xanthohumol isoxazole derivative 5 (17 mg, 0.0463 mmol, 82%) as a yellow solid: IR (neat) 3369, 2923, 1614, 1532, 1446, 1412, 1345, 1275, 1209, 1173, 1142, 1079, 803 cm-1; 1H NMR (700 MHz, $d_6$-DMSO) δ 9.85 (1H, br s), 9.74 (1H, br s), 8.54 (1H, br s), 7.71 (2H, d, J=8.7 Hz), 6.87 (2H, d, J=8.7 Hz), 6.83 (1H, s), 6.15 (1H, s), 5.13 (1H, tm, J=6.9 Hz), 3.67 (3H, s), 3.20 (2H, d, J=6.9 Hz), 1.70 (3H, s), 1.62 (3H, s) ppm; 13C NMR (175 MHz, $CDCl_3$) δ 165.7 (0), 161.2 (0), 158.8 (0), 158.1 (0), 156.3 (0), 154.5 (0), 129.6 (0), 128.0 (2C, 1), 123.6 (1), 120.1 (0), 115.7 (2C, 1), 108.5 (0), 102.4 (1), 97.2 (0), 91.5 (1), 55.4 (3), 25.5 (3), 21.7 (2), 17.8 (3) ppm; HRMS (ES+) m/z 368.1514 (calcd. for $C_{21}H_{22}NO_5$: 368.1498).

Example 6

Materials and Methods for Biological Examples

Nitric Oxide (NO) Assay. NO secreted by LPS-activated RAW 264.7 cells into the culture medium was determined as nitrite by the Griess reagent. RAW 264.7 1 cells obtained from the American Type Culture Collection (Manassas, VA, USA) were cultured in DMEM supplemented with 2 mM glutamine, antibiotics (100 U/mL penicillin and 100 μg/mL streptomycin), and 10% heat-inactivated fetal bovine serum. The cells were initially grown in 75 $cm^2$ culture flasks at 37° C. in a humidified incubator with 5% $CO_2$. After reaching 80% confluency, the cells were split by seeding them on 96-well plates (0.2 mL/well) at a density of $1.5\times10^5$ cells/mL. After a 24-hour incubation at 37° C., the cells were treated with LPS (1 μg/mL) with or without test compounds in various concentrations. Vehicle control cells were treated with dimethyl sulfoxide alone at a final concentration of 0.1%. Culture media from control and treated cells were collected after 24 hours of incubation and were frozen at −80° C. before analysis. For the determination of NO (as nitric oxide), 100-4, aliquots of the thawed culture media were mixed with an equal volume of Griess reagent on a 96-well plate. The Griess reagent is a 1:1 mixture (v/v) of 1% sulfanilamide and 0.1% naphthylethylenediamine dihydrochloride in 5% $H_3PO_4$. The samples were incubated for 10 minutes at room temperature and then the absorbance was read at 550 nm using a SpectraMax 190 (Molecular Devices, Sunnyvale, CA) plate reader.

Cell Viability Assays. Cells were seeded in 96-well plates 24 hours prior to adding the compound. HepG2 cells were seeded at a density of 5×104 cells/mL and C2C12 at 1×104 cells/mL in order to reach 80% confluency at the beginning of the experiment. After 24 hours, the culture medium was replaced with fresh medium containing various concentrations ranging between 0 and 200 μM of XP. The cells were incubated in the presence of the compound for 24 hours, at which time, the MTT viability assay was carried as previously described. MTT was dissolved at 0.5 mg/mL in serum-free Dulbecco's modified Eagle's medium, filter-sterilized and 100 μL was added to the cells. The cells were incubated for 3 hours and then acidified with 100% isopropanol for 15 minutes before absorbance reading at 570 nm on a BioTek Synergy HT plate reader.

Animal Studies. All animal experiments were performed in accordance with institutional and National Health and Medical Research Council guidelines. The experimental protocol was approved by the Institutional Animal Care and Use Committee at Oregon State University and the studies were carried out in accordance with the approved protocol. Nine-week-old wildtype male C57BL/6J mice were obtained from Jackson Laboratory (Bar Harbor, ME, USA). Mice were single-housed in ventilated cages under a 12-12 h light-dark cycle and fed a HFD (Dyets Inc., Bethlehem, PA, USA) containing 60, 20, and 20% total calories from fat, carbohydrate, and protein, respectively. XN (99% purity, Hopsteiner Inc., New York, NY, USA) and XP (99% purity) were mixed into the diet at a concentration of 0.066% for XN and 0.033% for XP to reach respective doses of 60 mg/kg body weight/day and 30 mg/kg body weight/day. Studies included eight HFD-fed mice, eight XP-treated mice, and four XN-treated mice; food intake and body weights were recorded weekly. At week 4, glucose tolerance was tested after 6 hours fasting. Following intraperitoneal bolus injection of 1.5 g/kg of D-glucose, blood glucose levels were measured at 0, 15, 30, 60, and 120 minures using a One Touch UltraMini glucometer (LifeScan Inc., Milpitas, CA, USA). At the end of 11 weeks of feeding, mice were euthanized, and blood, liver, BAT, epididymal WAT, and cortex samples were collected for analyses.

Measure of Metabolic Activity. Metabolic determinations were performed at week 6, with four mice from each treatment group housed in Promethion metabolic cages (Sable Systems, Las Vegas, NV, USA). The indirect calorimetry system consists of metabolic cages identical to regular cages with bedding, each equipped with food hoppers connected to load cells for food intake monitoring. Prior to data collection, all mice were acclimated to the cages for 8 hours. A standard 12 hours light/dark cycle was maintained throughout the calorimetry studies, and data was collected over three dark cycles and two light cycles. Metabolic measurements such as EE and respiratory exchange rate (calculated from the ratio of CO2 volume produced and O2 volume consumed) were measured. Motor activity and food intake were also recorded. JC-1 Mitochondrial Membrane Potential Assay. C2C12 cells were seeded in 96-well plates at 1×104 cells/mL. After 24 hours, the culture medium was replaced with fresh medium containing carbonyl cyanide p-(trifluoromethoxy) phenylhydrazone (FCCP) from Sigma-Aldrich (St Louis, MO, USA), XP, XN, or DMSO vehicle.

Cells were incubated in the presence of the treatments for 1 h and 5,5',6,6'-tetrachloro-1,1',3,3'-tetraethylbenzimidazolylcarbocyanine iodide (JC-1) dye was added to each well following the manufacturer's protocol (Cayman Chemical, Ann Arbor, MI, USA). JC-1 aggregates were detected with excitation and emission wavelengths of 540 and 570 nm. JC-1 monomers were detected with excitation and emission wavelengths of 485 and 535 nm on a BioTek Synergy HT plate reader.

Measure of Metabolic Parameters and Liver Enzymes. ALT and AST enzymatic activities and liver samples (n=4-8 per group) were homogenized in 10 mL of 100 mM Tris (pH=7.8) per gram of tissue. The homogenates were centrifuged at 10 000 g for 15 minutes at 4° C., and the supernatants were tested for ALT and AST activity using colorimetric assay kits purchased from Cayman Chemical (Ann Arbor, MI, USA). Triglycerides and total cholesterol were analyzed with commercially available kits (Cayman Chemical, Ann Arbor, MI, USA). Plasma glucose at week 11 was measured with a colorimetric assay, and plasma insulin, MCP-1, IL-6, and PCSK9 were analyzed by ELISA kits purchased from Abcam (Cambridge, UK).

Plasma and Cortex LC-MS Metabolomics. The left and right sides of the cortex were pooled and ground using liquid nitrogen. Cortex samples (approximately 30 mg) were extracted as previously described with slight modifications. Tissues were homogenized with 600 μL of cold 80% acetonitrile with 0.1% formic acid containing 0.2 μg/mL of dopamine-d4 (Sigma-Aldrich, St Louis, MO, USA) and 0.2 μg/mL of chlorpropamide (Sigma-Aldrich, St Louis, MO, USA) using a counter-top bullet blender for 2 min and centrifuged at 20 000 rpm for 10 minutes. Supernatants were transferred to high performance liquid chromatography (HPLC) vials for analysis.

Plasma metabolites were extracted with 400 μL of cold acetonitrile/methanol (1:1, v/v) containing 0.2 μg/mL of dopamine-d4 and 0.2 μg/mL of chlorpropamide per 50 μL of plasma. Samples were vortexed 30 s, incubated at −20° C. for 1 hour, and centrifuged at 13,000 rpm for 15 minutes, supernatants were evaporated under vacuum, and the dry extracts were reconstituted in 200 μL of 80% acetonitrile containing 0.1% formic acid. The samples were vortexed, centrifuged at 15,000 rpm for 5 minutes, and supernatants were transferred to HPLC vials for analysis.

LC-high-resolution mass spectrometry/MS. Data dependent acquisition in both negative and positive ion mode was conducted using a Shimadzu Nexera UPLC system coupled to an AB SCIEX TripleTOF 5600 mass spectrometer (AB SCIEX, Toronto, Canada). Chromatographic separation was conducted using an Inertsil Phenyl-3 column (4.6×150 mm, 100 Å, 5 μm; GL Sciences, Tokyo, Japan). Spray voltage was −4200 V for negative ion mode and 4500 V for positive ion mode acquisition. The injection volume was 3 μL. Metabolite identifications were performed using Progenesis QI software (V2.4.6911) with METLIN plugin V1.0.6499 (NonLinear Dynamics, United Kingdom). Progenesis QI was used for peak picking, retention time correction, data normalization, peak alignment, and metabolite annotations. Metabolites were detected in both ion modes; the one with the lowest coefficient of variation of the QC was kept.

Quantification of XP and XN. For plasma extractions, ascorbic acid (5 μL, 10% m/m water, Sigma-Aldrich, St Louis, MO, USA) was added to 40 μL of plasma. For tissue extractions, 20 mg of cortex was extracted with 200 μL of 50% methanol in water and 10 μL of ascorbic acid (10% m/m water). Samples were incubated with or without 10 μL of glucuronidase (20 mg/mL, Sigma-Aldrich, St Louis, MO, USA) for 3 hours at 37° C. The samples were extracted with 200 μL of acetonitrile containing 100 ng/mL of [13C3]-XN. The supernatant was transferred to a new tube and vacuum-dried, and the pellet was reconstituted in 100 μL of 50% methanol in water. UPLC-MS was performed using a hybrid triple quadrupole linear ion trap mass spectrometer (4000 QTRAP, AB SCIEX, Toronto, Canada). The elution profile was set as follows: 5% B from 0 to 0.5 min, 5 to 100% B from 0.5 to 3 minutes, 1 minute hold at 100% B, followed by re-equilibration of the HPLC column at 5% B for 2 minutes. Selected reaction monitoring transitions used for quantification were m/z 353.1>119.1 for XN, m/z 379.3>321.3 for XP, and m/z 356.1>120.1 for the [13C3]-XN internal standard.

Western Blotting. Approximately 100 mg of frozen BAT and WAT was homogenized in RIPA buffer with protease and phosphatase inhibitors (Santa Cruz Biotechnology, Dallas, TX, USA). Tissues were sonicated for 30 seconds, and the homogenates were centrifuged at 15700 g for 10 minutes to collect the supernatants. Protein (30 μg) was separated by SDS-PAGE using 4-15% MP TGX Gels (Bio-Rad, Hercules, CA, USA) and blotted onto nitrocellulose membranes. The membranes were blocked with 5% nonfat milk for 90 minutes and incubated with antibodies against GAPDH (#0411, Santa Cruz Biotechnology, Dallas, TX, USA) or UCP1 (#10983, Genetex, Irvine, CA, USA) for 60 minutes. After a second reaction with secondary antibodies (horseradish peroxidase-conjugated IgG antibodies), the protein bands on the nitrocellulose membranes were visualized by enhanced chemiluminescence substrate on an electrochemical luminescence (ECL) imager (Thermo Fisher Scientific, Waltham, MA, USA). Band intensities were quantified by densitometry using Image J software.

Statistical Analyses. Bar graph values are represented as mean±SEM (standard error of the mean). The data were analyzed using GraphPad Prism version 8.0 (San Diego, CA, USA). The statistical analyses compared each of the two treatment groups to the control group. A one-way ANOVA followed by Dunnett's test was used for single measures among animals (i.e., liver and plasma metabolic measures) and a repeated-measures-in-time design ANOVA for repeated measures within animals (i.e., glucose tolerance test, EE, and locomotor activity). Two-tailed unpaired t-tests were used to compare unconjugated and total concentrations of XP and XN.

Example 7

For plasma extractions, ascorbic acid (5 μL, 10% m/m water, Sigma Aldrich, St Louis, MO, USA) was added to 40 μL of plasma. Samples were incubated with or without 10 μL glucuronidase (20 mg/mL, Sigma Aldrich, St Louis, MO, USA) for 3 hr at 37° C. Samples were extracted with 200 μL of acetonitrile containing 100 ng/mL [$^{13}C_3$]—XN[1]. The supernatant was transferred to a new tube, vacuum-dried and the pellet was reconstituted in 100 μL of 50% methanol in water. UPLC-MS was performed using a hybrid triple quadrupole linear ion trap mass spectrometer (4000 QTRAP, AB SCIEX, Toronto, Canada) as previously reported with some modifications. The elution profile was set as follows: 5% solvent B from 0 to 0.5 minute, 5% to 100% B from 0.5-3 minutes, 1 minute hold at 100% B followed by re-equilibration of the HPLC column at 5% B for 2 minutes. Selected Reaction Monitoring transitions used for quantification were m/z 353.1>119.1 for XN, m/z 379.3>321.3 for XP and m/z 356.1>120.1 for [$^{13}C_3$]—XN internal standard. XP and XN concentrations were calculated by the external calibration method using calibration curves constructed from pure XP and XN standards.

Example 8

This example concerns the effects of administering 4-(5-(4-hydroxyphenyl)-1-methyl-1H-pyrazol-3-yl)-5-methoxy-2-(3-methylbut-2-en-1-yl)benzene-1,3-diol to mice after a pre-conditioning phase of 4 weeks during which animals were fed a high-fat diet (HFD) or a low-fat diet (LFD). Forty 9-week old wild-type (WT) male C57BL/6J mice were obtained from Jackson Laboratory (Bar Harbor, ME, USA). The mice were housed in ventilated cages under a 12-12-hr light-dark cycle. Of the 40 mice, 32 were fed a HFD (Dyets Inc., Bethlehem, PA, USA) containing 60%, 20% and 20% total calories from fat, carbohydrate and protein, respectively. The remaining 8 mice were fed a LFD (Dyets Inc., Bethlehem, PA, USA), containing 11%, 70% and 19% total calories from fat, carbohydrate and protein, respectively. XP was first dissolved in a mixture of oleic acid:propylene glycol:Tween 80 (0.9:1:1 by weight) before the solution was mixed into the HFD at a concentration of 0.066% to reach a dose of 60 mg/kg body weight/day. After 4 weeks of HFD feeding, the XP-containing HFD was given to 16 of the 32 HFD-pretreated mice for 8 weeks. Sixteen mice in HFD-pretreatment group received a HFD control diet that contained an identical amount of the mixture of oleic acid: propylene glycol:Tween 80 (0.9:1:1 by weight). The LFD-fed mice were continued on the LFD diet. Food intake and body weights were recorded weekly. The mice were euthanized at week 12.

Figure 24:
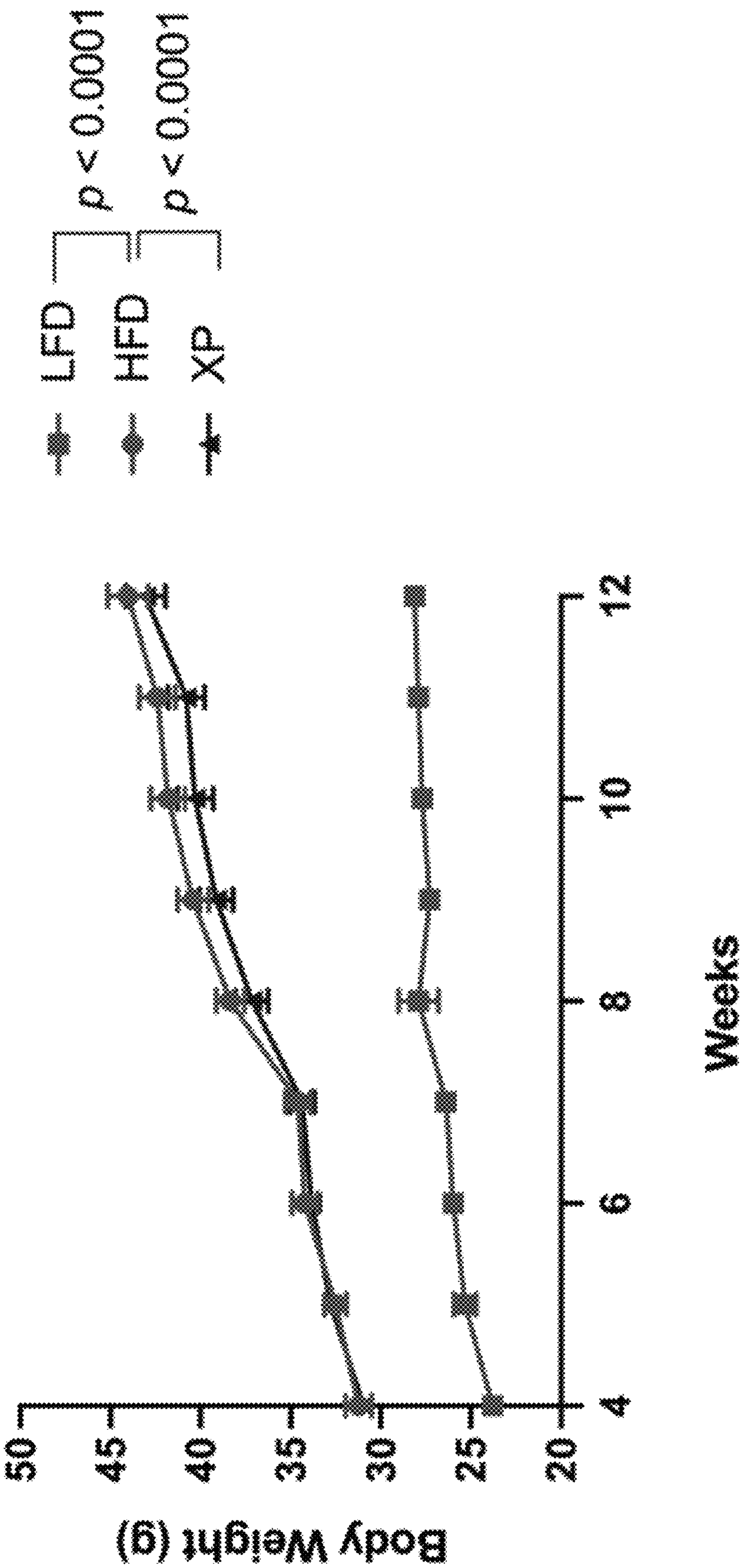
FIG. 24 is a graph of body weight (g) versus time (weeks) illustrating body weight gain over 8 weeks of oral administration of 4-(5-(4-hydroxyphenyl)-1-methyl-1H-pyrazol-3-yl)-5-methoxy-2-(3-methylbut-2-en-1-yl)benzene-1,3-diol (XP), where statistical significance ($p<0.05$) was assessed using repeated measures one-way ANOVA followed by Dunnett's test.
Figure 25:
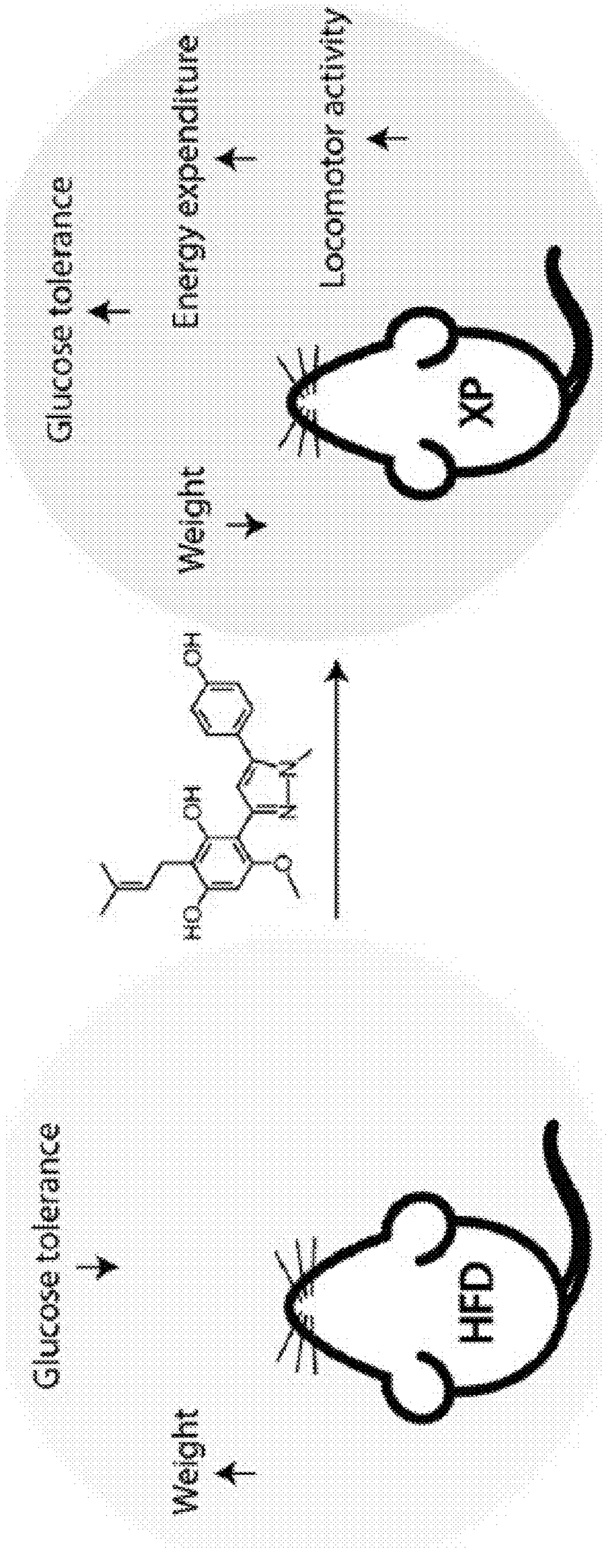
FIG. 25 is a schematic drawing illustrating that HFD-fed mice had increased weight and decreased glucose tolerance relative to HFD-fed mice that also received 4-(5-(4-hydroxyphenyl)-1-methyl-1h-pyrazol-3-yl)-5-methoxy-2-(3-methylbut-2-en-1-yl)benzene-1,3-diol and had decreased weight, increased glucose tolerance, increased energy expenditure and increased locomotor activity.

During the preconditioning period of 4 weeks, HFD-fed mice had a body weight of 31 g on average while the LFD-fed mice had an average body weight of 24 g. The 29% higher body weight of the HFD-fed mice reflects the development of an obesity phenotype. HFD-fed mice treated with 4-(5-(4-hydroxyphenyl)-1-methyl-1h-pyrazol-3-yl)-5-methoxy-2-(3-methylbut-2-en-1-yl)benzene-1,3-diol gained significantly less weight over the period of the feeding experiment than control HFD-fed mice ($p<0.0001$, FIG. 24) while there was no difference in food intake. The weight gain in the HFD-fed mice treated with XP started to slow after 4 weeks of treatment and the decrease in weight gain averaged to about 5% between weeks 9 and 12. FIG. 25 is a schematic drawing illustrating that HFD-fed mice had increased weight and decreased glucose tolerance relative to HFD-fed mice that also received embodiments of compounds according to the present invention, such as 4-(5-(4-hydroxyphenyl)-1-methyl-1h-pyrazol-3-yl)-5-methoxy-2-(3-methylbut-2-en-1-yl)benzene-1,3-diol. Mice treated with 4-(5-(4-hydroxyphenyl)-1-methyl-1h-pyrazol-3-yl)-5-methoxy-2-(3-methylbut-2-en-1-yl)benzene-1,3-diol also had decreased weight, increased glucose tolerance, increased energy expenditure and increased locomotor activity relative to mice that were not administered 4-(5-(4-hydroxyphenyl)-1-methyl-1h-pyrazol-3-yl)-5-methoxy-2-(3-methylbut-2-en-1-yl)benzene-1,3-diol.

TABLE 3

Ion Intensities of Annotated Metabolites (Alphabetical Order) in the Plasma of HFD-Fed Mice Untreated or Treated with XP or XN

| | CONTROL | | XP | | XN | |
|---|---|---|---|---|---|---|
| Ion intensities | Mean | SD | Mean | SD | Mean | SD |
| 1 Methylhistidine | 2022.18 | 402.64 | 1714.05 | 429.46 | 1856.12 | 397.33 |
| 1-Arachidonoylglycero-phosphoinositol | 6540.97 | 2366.13 | 6096.54 | 1090.83 | 7341.91 | 1598.70 |
| 1,2-DIPALMITOYL-SN-GLYCEROL | 10510.90 | 3892.53 | 10411.29 | 1671.83 | 10841.28 | 2301.65 |
| 12-HETE | 553.63 | 417.28 | 207.81 | 150.73 | 125.77 | 85.14 |
| 12-HYDROXY-DODECANOICACID | 82.33 | 39.28 | 106.16 | 44.70 | 63.92 | 16.27 |
| 16-HETE | 326.46 | 219.70 | 178.26 | 106.26 | 126.39 | 79.30 |
| 17A,21-DIHYDROXY-4-PREGNENE-3,20-DIONE | 123.15 | 41.08 | 109.57 | 47.00 | 176.93 | 63.53 |
| 2-DEOXY-D-GLUCOSE | 354.69 | 69.28 | 316.58 | 70.22 | 375.57 | 28.88 |
| 2-O-Methyl-L-fucose | 314.91 | 58.02 | 340.67 | 68.87 | 335.20 | 62.43 |
| 2'-DEOXYURIDINE 5'-MONOPHOSPHATE | 1841.82 | 196.86 | 1825.91 | 345.12 | 2090.92 | 542.15 |
| 25-hydroxy-cholesterol | 3551.25 | 1948.75 | 2283.16 | 423.42 | 5540.73 | 3358.63 |
| 3-Methyl-L-histidine | 363.39 | 95.62 | 315.07 | 95.95 | 303.45 | 56.88 |
| 4-Amino-2-methylenebutanoic acid | 139.49 | 46.47 | 161.10 | 66.36 | 156.78 | 19.80 |
| 4-formyl Indole | 1145.41 | 228.12 | 1410.02 | 225.43 | 1500.07 | 270.42 |
| 4-Hydroxy-2-oxoglutaric acid | 121.61 | 31.10 | 155.52 | 35.42 | 141.46 | 9.16 |
| 4-METHYL-2-OXO-PENTANOIC ACID | 404.22 | 55.62 | 437.50 | 80.35 | 409.27 | 81.87 |
| 5-AMINOPENTANOATE | 510.46 | 120.29 | 512.89 | 119.02 | 537.41 | 41.66 |
| 5-Methylcytidine | 3144.39 | 509.21 | 2834.22 | 975.41 | 3033.21 | 477.61 |
| 6-DEOXY-L-GALACTOSE | 226.28 | 23.50 | 237.55 | 31.73 | 236.60 | 30.81 |
| Abscisic acid | 57.61 | 5.04 | 65.68 | 8.54 | 37.04 | 11.30 |
| Acetylcarnitine | 2907.97 | 731.86 | 3021.32 | 750.74 | 3433.94 | 491.04 |
| Acetylcholine | 234.63 | 107.08 | 245.77 | 107.48 | 236.64 | 66.03 |
| ACONITATE | 18.16 | 4.25 | 18.82 | 4.91 | 11.59 | 4.54 |
| ADENOSINE 5'-MONOPHOSPHATE | 1521.84 | 1575.42 | 327.88 | 325.17 | 92.90 | 86.64 |
| ADENOSINE 5'-TRIPHOSPHATE | 3.77 | 4.03 | 1.81 | 1.66 | 1.24 | 0.67 |
| ALLANTOIN | 356.84 | 62.68 | 316.12 | 96.40 | 357.92 | 61.86 |
| Aloesol | 148.25 | 17.82 | 196.00 | 57.12 | 214.82 | 38.76 |

TABLE 3-continued

Ion Intensities of Annotated Metabolites (Alphabetical Order) in the Plasma of HFD-Fed Mice Untreated or Treated with XP or XN

| Ion intensities | CONTROL Mean | CONTROL SD | XP Mean | XP SD | XN Mean | XN SD |
|---|---|---|---|---|---|---|
| Aminoadipic acid | 67.11 | 19.17 | 77.68 | 20.55 | 81.06 | 5.82 |
| Arachidonic acid | 6305.54 | 835.36 | 5485.33 | 862.97 | 6687.50 | 735.38 |
| ARGININE | 2905.59 | 527.58 | 3170.02 | 917.34 | 2572.56 | 497.82 |
| AZELAIC ACID | 510.22 | 213.47 | 430.36 | 146.09 | 814.54 | 847.34 |
| BETAINE | 6273.84 | 1538.77 | 9249.91 | 1938.49 | 7372.00 | 990.57 |
| BILIVERDIN | 2281.78 | 1001.46 | 4061.01 | 1223.80 | 1949.28 | 1700.84 |
| C16 Sphingosine | 482.90 | 83.50 | 464.75 | 57.72 | 538.09 | 62.11 |
| CARNITINE | 14976.88 | 2490.88 | 14683.18 | 1114.07 | 17323.98 | 1298.15 |
| Cholic acid | 430.61 | 430.79 | 1649.14 | 2750.02 | 137.07 | 122.35 |
| CITRATE | 1464.15 | 188.71 | 1106.17 | 353.95 | 594.73 | 164.29 |
| CITRULLINE | 7772.19 | 1501.79 | 8129.05 | 1953.59 | 6985.18 | 633.28 |
| CREATINE | 25157.44 | 4710.63 | 17758.25 | 3074.39 | 18528.49 | 4010.24 |
| CREATININE | 873.35 | 247.68 | 747.95 | 58.35 | 779.10 | 78.54 |
| CYTOSINE | 70.88 | 22.72 | 58.61 | 16.10 | 58.20 | 9.55 |
| dCMP | 91.64 | 21.64 | 78.62 | 13.60 | 74.38 | 5.30 |
| DEOXYCHOLIC ACID | 75.41 | 31.46 | 795.13 | 1459.36 | 109.75 | 71.67 |
| DEOXYCYTIDINE | 218.31 | 71.88 | 297.52 | 31.35 | 219.82 | 38.73 |
| Deoxyribose | 115.58 | 21.06 | 130.39 | 31.60 | 119.57 | 25.48 |
| Deoxyuridine | 113.54 | 20.45 | 131.12 | 25.40 | 101.88 | 6.30 |
| Dihydroxybutyric acid | 134.10 | 19.20 | 128.68 | 38.89 | 126.19 | 6.86 |
| dimethylphosphatidy-lethanolamine | 385470.07 | 29687.09 | 334146.46 | 43443.53 | 355729.72 | 60140.98 |
| Docosahexaenoic acid | 6236.92 | 1638.93 | 4576.50 | 1271.46 | 6074.87 | 561.41 |
| Docosapentaenoic acid | 1160.01 | 202.75 | 1112.14 | 308.77 | 1217.91 | 80.42 |
| Docosatrienoic acid | 34.62 | 27.56 | 582.23 | 1074.17 | 47.16 | 25.52 |
| Docosenamide | 129117.49 | 76189.40 | 91216.94 | 74881.28 | 76919.48 | 53618.41 |
| Ethyl hydroxytridecanoate | 260.84 | 19.02 | 267.51 | 26.06 | 260.72 | 14.19 |
| FUMARATE | 9.65 | 4.05 | 13.52 | 5.64 | 10.29 | 3.68 |
| Galactosylceramide (d18:1/18:0) | 14.24 | 11.02 | 8.37 | 4.15 | 14.25 | 12.75 |
| GLUCONIC ACID | 496.05 | 86.99 | 558.44 | 194.66 | 485.35 | 84.61 |
| Glutamate | 314.50 | 74.67 | 338.34 | 49.34 | 269.55 | 50.55 |
| GLUTAMIC ACID | 5663.78 | 477.63 | 5577.20 | 706.90 | 5428.32 | 490.69 |
| GLUTAMINE | 5656.19 | 549.77 | 5799.34 | 591.09 | 5477.62 | 561.42 |
| Glutamylalanine | 401.73 | 105.87 | 405.31 | 143.64 | 432.95 | 155.06 |
| Glutamylleucine | 1804.42 | 386.30 | 2280.43 | 1066.53 | 2401.47 | 473.14 |
| Glutamylvaline | 313.22 | 82.11 | 360.54 | 129.31 | 345.12 | 45.17 |
| GLYCERATE | 49.03 | 16.05 | 42.37 | 10.23 | 38.39 | 11.70 |
| Glycerophosphocholine | 15326.99 | 1947.99 | 15023.63 | 3309.96 | 15186.89 | 1549.75 |
| Guanidinopropanoate | 131.29 | 33.08 | 86.58 | 10.83 | 82.89 | 16.04 |
| Guanosine monophosphate | 64.72 | 48.52 | 26.39 | 14.12 | 12.00 | 11.64 |
| Heptadecanoyl-glycerophosphoethanolamine | 1180.19 | 161.72 | 1668.81 | 227.88 | 1452.88 | 217.39 |
| Heptadecenoic acid | 11.38 | 3.64 | 14.08 | 9.08 | 10.33 | 5.74 |
| Hexadecanedioic acid | 58.37 | 8.06 | 70.47 | 26.22 | 71.58 | 7.03 |
| HISTIDINE | 855.70 | 207.49 | 1050.85 | 246.99 | 747.34 | 90.54 |
| Hydroxy-alpha-tocopherol | 202615.27 | 38429.80 | 183578.71 | 29124.84 | 149516.00 | 49535.51 |
| HYDROXYBENZALDEHYDE | 375.91 | 173.63 | 229.18 | 199.32 | 438.61 | 193.03 |
| Hydroxybutyric acid | 427.03 | 79.75 | 478.82 | 80.37 | 491.16 | 30.80 |
| Hydroxyphenethylamine | 13610.38 | 3419.93 | 14732.47 | 2735.28 | 16045.13 | 2595.11 |
| hydroxytetradecanoylcarnitine | 353.28 | 180.84 | 328.19 | 107.02 | 384.78 | 62.24 |
| Hypoxanthine | 1454.07 | 543.02 | 475.33 | 344.74 | 131.79 | 100.00 |
| Imidazoleacetic acid ribotide | 14.83 | 7.83 | 22.12 | 3.37 | 23.46 | 2.16 |
| Indole-3-acetic-acid-O-glucuronide | 193.50 | 51.23 | 192.73 | 53.06 | 183.77 | 45.10 |
| Indoleacrylic acid | 43252.92 | 7272.78 | 45452.31 | 9734.94 | 52950.38 | 7587.42 |
| Indolelactic acid | 337.95 | 52.04 | 342.25 | 84.04 | 326.74 | 67.05 |
| Indoxyl sulfate | 4463.39 | 751.91 | 3977.22 | 767.74 | 5329.46 | 913.71 |
| Inosine | 1164.92 | 578.32 | 369.81 | 226.96 | 87.09 | 88.47 |
| Inosine 5'-monophosphate (IMP) | 678.90 | 595.80 | 216.66 | 107.78 | 108.93 | 76.05 |
| Isobutyl salicylate | 1380.38 | 103.35 | 1612.90 | 174.55 | 1650.11 | 146.78 |
| ISOCITRIC ACID | 335.42 | 78.49 | 382.98 | 102.99 | 364.96 | 35.82 |
| ISOLEUCINE | 9537.82 | 3548.84 | 8721.84 | 3153.02 | 9268.03 | 1337.58 |
| KETOGLUTARIC ACID | 159.56 | 43.35 | 205.82 | 70.78 | 168.10 | 62.17 |
| L-AMINOCYCLOPROPANE-1-CARBOXYLATE | 2877.14 | 360.89 | 3387.71 | 744.47 | 2227.78 | 271.89 |
| L-N-Carboxymethylserine | 13.64 | 7.55 | 14.85 | 4.14 | 12.69 | 4.69 |
| L-OLEOYL-RAC-GLYCEROL | 9895.49 | 3198.61 | 10062.75 | 1868.01 | 12820.91 | 2708.81 |
| LACTATE | 7365.87 | 1103.82 | 7487.81 | 1890.20 | 8305.33 | 2092.96 |
| Lathosterol | 50102.51 | 10711.84 | 50015.90 | 7218.56 | 47888.28 | 11476.39 |
| Lauroyl diethanolamide | 383.11 | 184.42 | 256.27 | 108.24 | 173.39 | 42.56 |
| LAUROYLCARNITINE | 75.48 | 10.94 | 93.74 | 32.40 | 88.35 | 28.09 |

TABLE 3-continued

Ion Intensities of Annotated Metabolites (Alphabetical Order) in the Plasma of HFD-Fed Mice Untreated or Treated with XP or XN

| | CONTROL | | XP | | XN | |
|---|---|---|---|---|---|---|
| Ion intensities | Mean | SD | Mean | SD | Mean | SD |
| Linoleic acid | 11770.28 | 2850.54 | 10456.44 | 1469.17 | 12967.04 | 2348.31 |
| LYSINE | 1649.29 | 447.98 | 1662.10 | 612.62 | 1513.06 | 331.89 |
| MALATE | 581.55 | 242.46 | 658.47 | 319.58 | 451.54 | 201.06 |
| Menthyl lactate | 116.38 | 15.25 | 104.95 | 16.02 | 124.26 | 42.91 |
| METHACHOLINE | 211.90 | 62.14 | 249.28 | 121.30 | 473.22 | 218.59 |
| METHIONINE | 4658.27 | 1436.62 | 5342.36 | 1603.18 | 5098.44 | 1174.84 |
| METHYLMALONATE | 166.87 | 65.59 | 180.69 | 44.77 | 176.06 | 31.64 |
| Monopalmitin | 142119.68 | 12665.01 | 141993.27 | 9100.65 | 149217.61 | 9437.20 |
| MYRISTIC ACID | 172.14 | 102.78 | 151.58 | 52.11 | 206.93 | 58.41 |
| N-ACETYL-D-TRYPTOPHAN | 305.73 | 67.05 | 294.99 | 63.74 | 250.30 | 42.62 |
| N-ACETYL-DMethionine | 22.03 | 10.29 | 25.91 | 17.71 | 24.07 | 8.65 |
| N-Acetyl-Glutamic acid | 47.33 | 21.47 | 57.25 | 20.87 | 44.50 | 14.75 |
| N-ACETYL-Phenylalanine | 188.98 | 63.60 | 218.25 | 72.52 | 210.24 | 28.79 |
| N-ACETYLTAURINE | 48.64 | 8.50 | 46.37 | 13.06 | 44.15 | 1.80 |
| N-Formyl-Glutamic acid | 41.76 | 5.78 | 34.50 | 10.02 | 32.55 | 9.11 |
| N-Palmitoylsphingosine | 680.53 | 361.06 | 763.63 | 192.29 | 852.23 | 291.26 |
| Niacinamide | 380.97 | 118.50 | 268.01 | 54.68 | 309.14 | 23.12 |
| Nicotinate D-ribonucleoside | 72.05 | 39.14 | 33.89 | 20.60 | 4.91 | 6.37 |
| Nicotine glucuronide | 43.05 | 17.44 | 32.10 | 4.96 | 25.85 | 6.27 |
| Nonadecenoic acid | 12261.48 | 3472.57 | 12941.51 | 3675.21 | 12514.89 | 2410.31 |
| octadecenal | 14836.10 | 2951.16 | 15328.62 | 1297.11 | 10834.42 | 2060.82 |
| Oleamide | 3572.00 | 528.18 | 3808.55 | 348.15 | 2988.69 | 455.95 |
| ORNITHINE | 143.82 | 38.40 | 142.04 | 32.99 | 122.48 | 8.73 |
| Oxoadipic acid | 32.92 | 4.77 | 43.49 | 27.72 | 35.79 | 12.54 |
| PALMITATE | 5288.97 | 695.39 | 4568.91 | 319.93 | 5209.89 | 511.00 |
| Palmitic acid | 1583.10 | 429.59 | 1640.53 | 278.22 | 1414.30 | 109.77 |
| Palmitic amide | 476.68 | 186.64 | 347.83 | 183.61 | 309.62 | 43.37 |
| PALMITOLEIC ACID | 981.92 | 268.19 | 857.54 | 288.54 | 1259.03 | 123.18 |
| PANTOTHENIC ACID | 175.57 | 41.66 | 159.32 | 40.67 | 168.15 | 22.60 |
| peroxy-eicosatetraenoate | 357.93 | 91.90 | 272.51 | 58.94 | 432.68 | 137.16 |
| PETROSELINIC ACID | 8851.51 | 1518.44 | 8129.59 | 768.95 | 9621.98 | 1106.34 |
| PHENACYLAMINE | 3717.55 | 1260.90 | 4337.08 | 1109.47 | 4221.09 | 1396.45 |
| Phenylacetylglycine | 218.37 | 37.74 | 182.39 | 80.06 | 258.54 | 56.25 |
| Phenylalanine | 4211.20 | 902.99 | 4634.46 | 588.85 | 4508.18 | 617.53 |
| Proline | 203.97 | 40.80 | 215.42 | 61.65 | 192.66 | 59.17 |
| PROLINE | 5202.56 | 1243.78 | 6417.96 | 2498.39 | 6485.19 | 1803.07 |
| Pseudouridine | 401.81 | 69.47 | 355.67 | 60.08 | 343.21 | 22.04 |
| Pyroglutamic acid | 331.41 | 146.93 | 283.14 | 94.60 | 336.82 | 175.72 |
| RESORCINOL | 17.06 | 8.41 | 15.66 | 9.13 | 4.48 | 3.51 |
| Ribothymidine | 72.88 | 12.95 | 72.63 | 6.71 | 76.63 | 4.68 |
| S-Adenosylmethionine | 387.42 | 128.45 | 394.97 | 120.32 | 308.49 | 89.49 |
| Salicylaldehyde | 1125.43 | 369.65 | 1273.80 | 513.10 | 1264.67 | 451.82 |
| SPHINGANINE | 292.77 | 24.75 | 286.43 | 30.92 | 298.22 | 21.91 |
| Sphingosine | 389.01 | 105.21 | 342.99 | 53.95 | 328.69 | 74.00 |
| Sphingosine 1-phosphate (d16:1-P) | 288.23 | 144.40 | 245.00 | 102.81 | 405.43 | 145.85 |
| Sphingosine-1-phosphate | 1314.67 | 274.97 | 1107.92 | 172.10 | 977.95 | 260.01 |
| Spisulosine | 893.63 | 178.15 | 986.35 | 122.08 | 942.56 | 98.16 |
| stearoyl sphingomyelin | 454.83 | 206.55 | 496.52 | 95.79 | 381.66 | 124.57 |
| TAURINE | 2156.26 | 541.93 | 2312.29 | 408.77 | 1903.36 | 290.92 |
| Tetrahydrodeoxycortisol | 3571.34 | 640.96 | 3425.72 | 741.57 | 3998.80 | 845.11 |
| THYMIDINE | 124.29 | 102.29 | 121.92 | 22.36 | 76.44 | 5.75 |
| THYROXINE | 77.42 | 17.43 | 68.94 | 25.53 | 74.75 | 25.95 |
| Trihydroxypregnenone | 4746.17 | 831.73 | 4434.98 | 251.40 | 5634.04 | 563.64 |
| TRYPTOPHAN | 13679.34 | 2320.41 | 16153.09 | 2760.66 | 17604.95 | 2818.54 |
| TYROSINE | 3372.86 | 841.19 | 3794.58 | 966.03 | 3387.28 | 451.68 |
| Undecanedicarboxylic acid | 2328.13 | 657.25 | 2149.24 | 315.15 | 1382.74 | 94.79 |
| URATE | 4623.65 | 1183.97 | 4262.55 | 473.62 | 4494.36 | 594.76 |
| URIDINE | 886.11 | 274.79 | 921.72 | 237.97 | 849.96 | 76.81 |
| UROCANATE | 115.06 | 66.51 | 116.19 | 53.96 | 59.41 | 37.55 |
| VALINE | 3510.11 | 609.52 | 4139.87 | 1562.96 | 3986.90 | 389.34 |
| Xanthine | 976.06 | 468.95 | 368.21 | 271.70 | 65.18 | 42.34 |

TABLE 4

Ion intensities of Annotated Metabolites (Alphabetical Order) in the Cortex of HFD-Fed Mice Untreated or Treated with XP or XN

| | CONTROL | | XP | | XN | |
|---|---|---|---|---|---|---|
| Ion intensities | Mean | SD | Mean | SD | Mean | SD |
| 1-Arachidonoyl-glycerophosphoinositol | 676.19 | 262.41 | 546.96 | 228.24 | 645.87 | 90.04 |
| 1-Palmitoyl-2-linoleoyl PE | 980.81 | 1195.05 | 1180.62 | 739.68 | 1782.31 | 688.05 |
| 1,2-DIPALMITOYL-SN-GLYCEROL | 1871.82 | 753.12 | 1513.84 | 620.60 | 934.62 | 205.70 |
| 12-HYDROXYDODECANOIC-ACID | 2357.96 | 254.38 | 2251.29 | 219.95 | 2479.58 | 315.79 |
| 2-Pyrrolidinone | 1456.99 | 351.19 | 1222.06 | 244.13 | 1091.46 | 197.13 |
| 2'-DEOXYURIDINE 5'-MONOPHOSPHATE | 672.69 | 88.49 | 594.66 | 90.72 | 615.86 | 74.78 |
| 20-Hydroxy-PGE2 | 5846.73 | 3017.54 | 7093.39 | 2784.84 | 9703.49 | 1681.47 |
| 27-Hydroxycholesterol | 17334.60 | 4424.86 | 20090.45 | 3600.31 | 17882.79 | 2028.14 |
| 3-Methyl-L-histidine | 683.23 | 163.20 | 518.49 | 146.84 | 495.48 | 160.53 |
| 3-PHOSPHO-GLYCERIC ACID | 3261.95 | 496.84 | 2370.20 | 246.51 | 2094.74 | 576.10 |
| 5-Acetylamino-6-amino-3-methyluracil | 40.45 | 28.61 | 52.73 | 54.70 | 108.09 | 37.82 |
| 5-Methylcytidine | 10442.97 | 2800.16 | 9448.98 | 2407.48 | 6615.71 | 1604.27 |
| Acetylcarnitine | 9822.22 | 7697.96 | 12649.68 | 1542.05 | 11173.39 | 2188.42 |
| Acetylcholine | 1365.37 | 1070.40 | 1745.95 | 173.21 | 1788.61 | 515.58 |
| Adenine | 2548.02 | 634.98 | 1949.85 | 500.33 | 1575.62 | 665.71 |
| ADENOSINE | 67854.47 | 18030.22 | 49823.74 | 12041.86 | 42044.83 | 17145.93 |
| ADENOSINE 5'-DIPHOSPHORIBOSE | 4201.75 | 1803.98 | 4312.21 | 3003.12 | 2010.85 | 697.06 |
| ADENOSINE 5'-MONOPHOSPHATE | 103745.22 | 24069.71 | 90459.20 | 11639.71 | 75745.39 | 11376.45 |
| ADENOSINE-5'-DIPHOSPHOGLUCOSE | 1778.74 | 655.85 | 1755.31 | 295.36 | 924.21 | 473.05 |
| Adenylosuccinate | 1067.71 | 389.40 | 1016.78 | 740.24 | 482.18 | 138.85 |
| Adenylsuccinic acid | 2021.11 | 2182.73 | 3152.34 | 803.27 | 1871.57 | 724.97 |
| ADP | 2958.20 | 1630.52 | 3426.97 | 1932.33 | 1070.27 | 448.77 |
| AMINOADIPATE | 312.75 | 86.28 | 331.86 | 120.44 | 211.18 | 24.96 |
| Arachidonic acid | 23477.35 | 6530.51 | 20901.19 | 4579.33 | 25496.26 | 2612.99 |
| Arachidonic acid ethyl ester | 173.81 | 227.88 | 351.43 | 471.40 | 417.92 | 210.53 |
| Arginine | 2474.67 | 467.11 | 2112.34 | 386.13 | 1863.90 | 128.50 |
| ASCORBATE | 2544.27 | 1073.05 | 1431.15 | 780.13 | 2138.35 | 415.74 |
| ASPARTATE | 1330.32 | 121.77 | 1333.10 | 319.91 | 1174.88 | 182.03 |
| Aspartic acid | 10030.66 | 1445.61 | 8729.17 | 678.09 | 8381.28 | 1139.22 |
| BILIVERDIN | 126.06 | 139.56 | 167.09 | 113.25 | 251.38 | 222.57 |
| CARNITINE | 16961.71 | 2733.45 | 14584.14 | 2359.61 | 11992.59 | 2817.72 |
| Carnosine | 1305.59 | 206.36 | 1422.99 | 394.96 | 929.30 | 289.29 |
| CDP-Ethanolamine | 543.60 | 139.89 | 571.19 | 292.16 | 303.02 | 77.30 |
| CHENODEOXYCHOLATE | 3932.21 | 1331.10 | 5735.03 | 1219.70 | 5290.32 | 895.72 |
| Choline | 10547.29 | 2011.82 | 8899.36 | 1384.91 | 7326.72 | 1593.13 |
| CITRATE | 2288.02 | 1154.47 | 1682.49 | 1138.67 | 997.79 | 377.90 |
| CMP | 662.79 | 292.58 | 688.26 | 215.14 | 586.09 | 98.06 |
| Creatine | 101574.86 | 10813.87 | 89712.34 | 4580.10 | 81660.56 | 7776.95 |
| cyclic GMP-AMP | 2657.48 | 630.46 | 2077.75 | 357.26 | 1495.60 | 492.95 |
| Cysteineglutathione disulfide | 1562.76 | 257.85 | 1531.40 | 301.62 | 1321.30 | 442.11 |
| Cytidine | 911.89 | 131.01 | 846.95 | 167.84 | 766.86 | 112.81 |
| Cytidine 2',3'-cyclic phosphate | 396.53 | 102.13 | 356.88 | 112.66 | 419.79 | 73.33 |
| Cytidine diphosphate choline (CDPcholine) | 2395.99 | 624.61 | 2658.54 | 773.12 | 2132.21 | 1031.84 |
| D-Glucaro-1,4-lactone | 2149.75 | 384.28 | 1887.47 | 251.37 | 1852.68 | 223.47 |
| D-GLUCOSE 6-PHOSPHATE | 142.93 | 59.56 | 138.50 | 115.93 | 54.37 | 6.88 |
| D-RIBOSE 5-PHOSPHATE | 140.21 | 34.60 | 136.10 | 36.92 | 119.65 | 24.30 |
| Deoxycytidine | 917.51 | 333.32 | 665.81 | 336.29 | 405.53 | 169.91 |
| Deoxyguanosine | 3233.25 | 562.31 | 2401.12 | 913.31 | 2552.08 | 279.09 |
| DESMOSTEROL | 13404.22 | 4816.98 | 15551.25 | 2455.94 | 16777.33 | 2719.43 |
| diethyltoluamide | 4.49 | 3.46 | 5.17 | 2.21 | 8.44 | 8.54 |
| DIHYDROOROTATE | 153.25 | 140.75 | 91.24 | 78.78 | 129.45 | 96.16 |
| docosa-hexaenoic acid | 1867.75 | 1984.32 | 1911.88 | 1472.14 | 3095.80 | 1110.72 |
| Docosahexaenoic acid | 3654.23 | 1359.11 | 2873.42 | 984.88 | 3528.63 | 533.93 |
| Docosenamide | 9042.57 | 9980.17 | 20845.53 | 29876.46 | 22701.50 | 12073.48 |
| Dodecanedioic acid | 329.67 | 30.13 | 333.82 | 59.41 | 332.32 | 28.28 |
| Ergothioneine | 686.49 | 210.34 | 515.38 | 136.25 | 433.26 | 150.86 |
| ERUCIC ACID | 103.85 | 9.92 | 98.90 | 13.04 | 114.42 | 18.36 |

TABLE 4-continued

Ion intensities of Annotated Metabolites (Alphabetical Order) in the Cortex of HFD-Fed Mice Untreated or Treated with XP or XN

| | CONTROL | | XP | | XN | |
|---|---|---|---|---|---|---|
| Ion intensities | Mean | SD | Mean | SD | Mean | SD |
| ETHANOLAMINE PHOSPHATE | 432.43 | 58.14 | 441.02 | 54.33 | 361.87 | 18.12 |
| Ethyl nicotinate | 98.37 | 29.61 | 81.18 | 11.98 | 74.78 | 9.10 |
| Glutamate | 54069.90 | 2918.77 | 53559.34 | 4163.54 | 45779.91 | 3366.66 |
| GLUTAMIC ACID | 9195.59 | 1396.08 | 9048.31 | 1410.52 | 7047.98 | 866.05 |
| GLUTAMINE | 22314.45 | 1902.21 | 22688.89 | 4953.24 | 18241.11 | 2197.57 |
| Glutathione | 269122.48 | 26688.69 | 232313.32 | 19024.11 | 194624.55 | 36302.26 |
| Glycerophosphocholine | 143147.14 | 21067.25 | 124857.55 | 13446.05 | 104911.40 | 19625.71 |
| GUANOSINE 5'-MONOPHOSPHATE | 4313.34 | 1540.39 | 4141.69 | 1915.66 | 2052.93 | 614.97 |
| Guanosine monophosphate | 819.13 | 177.62 | 845.86 | 344.91 | 482.20 | 134.48 |
| HEPTADECANOATE | 23.27 | 9.45 | 23.50 | 8.04 | 24.77 | 1.96 |
| HISTIDINE | 1281.84 | 337.09 | 1129.76 | 176.26 | 901.19 | 85.47 |
| Homocarnosine | 717.55 | 142.87 | 689.23 | 273.94 | 433.96 | 135.79 |
| Homoserine | 1050.91 | 336.93 | 1034.62 | 333.84 | 952.74 | 358.92 |
| Hydroxybutyric acid | 3173.43 | 533.59 | 2833.09 | 271.41 | 2561.64 | 308.39 |
| hydroxyhexadecanoyl carnitine | 1004.56 | 850.65 | 1048.02 | 462.47 | 1430.92 | 317.38 |
| Hydroxyphenethylamine | 4144.73 | 1449.75 | 4074.28 | 1935.55 | 3489.46 | 1146.87 |
| hydroxyvitamin D3 | 19574.25 | 3168.26 | 21210.39 | 2965.65 | 16859.40 | 1238.56 |
| Hypoxanthine | 115.01 | 38.55 | 88.42 | 36.55 | 100.45 | 13.60 |
| Hypusine | 208.01 | 73.62 | 196.91 | 62.01 | 94.62 | 48.11 |
| Indoleacetaldehyde | 695.89 | 206.47 | 523.18 | 106.69 | 565.25 | 52.14 |
| Inosine | 1713.03 | 429.42 | 1409.62 | 589.08 | 1426.47 | 301.70 |
| Inosine 5'-monophosphate (IMP) | 3153.42 | 1318.39 | 5581.09 | 1838.53 | 3551.74 | 1248.02 |
| ISOCITRIC ACID | 1618.83 | 449.14 | 2051.66 | 595.22 | 2099.31 | 256.47 |
| ISOLEUCINE | 1843.59 | 465.89 | 1578.44 | 316.49 | 1271.60 | 271.45 |
| Isostearic acid | 2076.89 | 503.07 | 1901.95 | 351.18 | 2314.30 | 131.43 |
| L-2-Amino-5-hydroxypentanoicacid | 2630.36 | 503.68 | 2343.03 | 383.18 | 1771.05 | 580.31 |
| L-OLEOYL-RAC-GLYCEROL | 2631.51 | 2151.96 | 2628.37 | 1431.78 | 3415.51 | 467.22 |
| LACTATE | 3290.43 | 420.15 | 3144.80 | 204.70 | 3374.25 | 80.76 |
| Lathosterol | 11889.95 | 10016.91 | 14569.93 | 7149.22 | 23593.87 | 4640.17 |
| LAUROYLCARNITINE | 252.97 | 181.07 | 277.93 | 127.42 | 384.69 | 91.33 |
| LEUKOTRIENE B4 | 31.84 | 14.06 | 30.73 | 14.98 | 49.50 | 18.87 |
| Lipoamide | 48.45 | 56.43 | 114.97 | 50.15 | 70.91 | 10.55 |
| LYSINE | 119.09 | 46.18 | 107.27 | 50.92 | 51.50 | 13.67 |
| MALATE | 1589.34 | 268.63 | 1664.52 | 429.85 | 1271.76 | 167.55 |
| Methionine | 2323.80 | 692.61 | 2031.63 | 518.38 | 1365.89 | 520.23 |
| Methylthioadenosine | 3948.71 | 405.25 | 3521.96 | 687.75 | 2473.94 | 855.03 |
| Myristoylcarnitine | 1187.26 | 1006.16 | 1303.77 | 484.49 | 1742.03 | 274.00 |
| N-(1-Deoxy-1-fructosyl) serine | 7199.27 | 4333.80 | 4331.01 | 4699.01 | 3036.19 | 812.47 |
| N-(1-Deoxy-1-fructosyl) serine | 7199.27 | 4333.80 | 4331.01 | 4699.01 | 3036.19 | 812.47 |
| N-a-Acetyl-Arginine | 264.32 | 69.18 | 270.36 | 76.67 | 175.03 | 70.51 |
| N-Acetyl-Glutamic acid | 199.27 | 44.22 | 205.45 | 71.63 | 154.68 | 24.39 |
| N-Acetyl-L-alanine | 2349.66 | 629.78 | 1909.11 | 407.47 | 1997.71 | 518.46 |
| N-ACETYL-L-ASPARTICACID | 28977.10 | 3304.95 | 25975.80 | 2516.65 | 24960.43 | 2887.09 |
| N-Acetylaspartylglutamic acid | 3177.29 | 1010.87 | 2955.57 | 1043.92 | 2179.47 | 442.78 |
| N-Acetylglutamine | 386.78 | 95.07 | 519.28 | 380.93 | 273.18 | 26.10 |
| N-Acetylisoputreanine | 202.65 | 53.17 | 153.75 | 74.61 | 99.54 | 51.86 |
| N-Acetyllactosamine | 292.77 | 66.77 | 273.32 | 48.51 | 308.43 | 68.08 |
| N-ACETYLNEURAMINATE | 1674.83 | 636.11 | 1670.91 | 855.36 | 817.62 | 231.58 |
| N-Linoleoyl GABA | 72.49 | 55.17 | 54.12 | 41.07 | 57.01 | 15.60 |
| N-Methyl-Glutamate | 3276.79 | 458.73 | 2772.85 | 659.48 | 2277.43 | 359.62 |
| N,N-dimethyl-Safingol | 606.88 | 108.02 | 578.09 | 57.26 | 638.46 | 20.07 |
| NAD | 1197.14 | 386.11 | 1268.92 | 537.93 | 532.29 | 58.00 |
| NE,NE,NE-TRIMETHYLLYSINE | 4477.33 | 553.45 | 3943.68 | 478.37 | 2830.12 | 1099.23 |
| Niacinamide | 6581.01 | 2274.69 | 5120.54 | 2455.80 | 4607.66 | 1441.76 |
| Nicotinamide adenine dinucleotide (NAD) | 42064.91 | 9021.91 | 37985.70 | 6238.99 | 2094413 | 10646.20 |

TABLE 4-continued

Ion intensities of Annotated Metabolites (Alphabetical Order) in the Cortex of HFD-Fed Mice Untreated or Treated with XP or XN

| | CONTROL | | XP | | XN | |
|---|---|---|---|---|---|---|
| Ion intensities | Mean | SD | Mean | SD | Mean | SD |
| O-Phosphoethanolamine | 144.00 | 148.30 | 302.71 | 171.59 | 497.23 | 223.04 |
| Octadecenoic acid | 191.97 | 82.85 | 169.48 | 93.15 | 202.97 | 57.47 |
| Oleamide | 4137.76 | 620.87 | 3677.58 | 503.45 | 4025.45 | 574.70 |
| Oxidized glutathione | 4424.27 | 1782.50 | 4537.22 | 1620.09 | 2115.40 | 668.62 |
| PALMITATE | 1446.94 | 424.66 | 1211.29 | 223.52 | 1472.32 | 102.52 |
| PALMITOLEIC ACID | 70.26 | 38.84 | 39.36 | 16.54 | 62.02 | 13.24 |
| PANTOTHENIC ACID | 560.14 | 117.95 | 524.89 | 120.40 | 442.74 | 23.50 |
| PETROSELINIC ACID | 160.23 | 117.99 | 142.54 | 74.98 | 220.71 | 68.52 |
| PHENYLALANINE | 3682.30 | 1334.92 | 2973.73 | 1192.43 | 2371.34 | 344.75 |
| PHENYLETHANOLAMINE | 1924.12 | 672.00 | 1559.27 | 597.34 | 1245.94 | 178.35 |
| Phenylpropionylglycine | 495.18 | 189.82 | 431.18 | 88.24 | 294.60 | 101.12 |
| Phosphocholine | 26138.38 | 3520.33 | 23860.56 | 3148.98 | 18574.78 | 3669.20 |
| Phosphodimethyl-ethanolamine | 255.15 | 48.76 | 269.92 | 123.71 | 161.80 | 38.60 |
| Pipecolic acid | 549.08 | 92.62 | 516.02 | 63.65 | 422.43 | 85.79 |
| Propionylcarnitine | 724.28 | 193.75 | 540.78 | 90.49 | 571.28 | 205.22 |
| Pyridoxamine-5'-Phosphate | 490.29 | 250.93 | 484.54 | 136.29 | 377.92 | 132.12 |
| RAC-GLYCEROL-L-MYRISTATE | 319.74 | 41.13 | 283.53 | 44.20 | 293.55 | 47.88 |
| S-Adenosylhomocysteine | 582.61 | 97.44 | 473.94 | 73.89 | 397.04 | 149.61 |
| S-Adenosylmethionine | 22627.67 | 3108.82 | 18868.04 | 3529.27 | 11562.08 | 4070.34 |
| SERINE | 411.07 | 152.43 | 483.60 | 214.09 | 355.32 | 80.31 |
| sn-glycero-3-Phosphoethanolamine | 1040.89 | 238.06 | 994.53 | 230.15 | 737.74 | 171.79 |
| Spermic acid 1 | 210.37 | 27.94 | 199.76 | 56.87 | 178.91 | 44.60 |
| Spermidine | 9110.12 | 1992.59 | 7809.52 | 1773.26 | 5406.36 | 1166.30 |
| Sphinganine | 21.50 | 20.75 | 23.16 | 22.22 | 34.01 | 11.23 |
| Sphinganine 1-phosphate | 1058.64 | 1310.50 | 1966.99 | 1000.28 | 2568.50 | 917.48 |
| Sphingosine | 1113.75 | 523.84 | 1163.81 | 283.98 | 1322.46 | 136.98 |
| Stearoylglycerophosphoserine | 1889.47 | 393.50 | 1831.40 | 154.97 | 2006.21 | 192.91 |
| SUCCINATE | 338.30 | 40.66 | 304.14 | 37.00 | 362.22 | 33.79 |
| Succinyladenosine | 298.30 | 93.78 | 217.97 | 69.86 | 192.45 | 30.30 |
| TAURINE | 7296.71 | 715.64 | 6801.22 | 847.06 | 6070.22 | 250.09 |
| Tetradecanedioic acid | 115.80 | 20.48 | 115.20 | 20.30 | 125.75 | 20.76 |
| Tetrahydrodeoxycortisol | 3069.56 | 704.23 | 2674.78 | 402.91 | 3344.70 | 251.31 |
| THEOPHYLLINE | 18.59 | 8.24 | 18.56 | 11.97 | 18.71 | 9.78 |
| Threoninyl-Alanine | 317.88 | 135.37 | 295.96 | 93.85 | 227.23 | 145.24 |
| TRYPTOPHAN | 1913.32 | 961.42 | 1355.41 | 610.41 | 1131.43 | 274.07 |
| Tyrosine | 7205.04 | 1442.77 | 6818.63 | 2477.78 | 4311.01 | 1396.41 |
| Undecanedicarboxylic acid | 237.29 | 30.87 | 219.08 | 16.36 | 236.12 | 26.28 |
| Uracil | 273.47 | 44.52 | 225.61 | 52.98 | 201.36 | 36.86 |
| URIDINE | 1306.88 | 234.45 | 1161.25 | 282.36 | 1155.56 | 127.35 |
| Uridine 5'-diphosphate | 433.59 | 170.93 | 422.30 | 83.95 | 248.01 | 82.90 |
| URIDINE 5'-DIPHOSPHOGALACTOSE | 1716.34 | 896.73 | 1728.73 | 1353.83 | 462.04 | 223.47 |
| URIDINE-5-MONOPHOSPHATE | 3832.91 | 1200.77 | 3704.01 | 861.47 | 2103.27 | 454.74 |
| Xanthine | 168.59 | 47.57 | 155.79 | 49.22 | 137.03 | 7.96 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, having a Formula I

Formula I

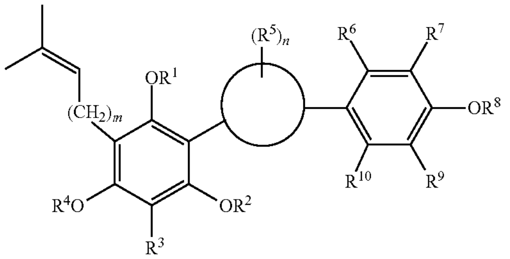

where:

m is 1-10;

n=0 up to the number of ring positions available for substitution;

$R^1$-$R^4$ and $R^6$-$R^{10}$ are independently selected from H, $C_1$-$C_{10}$ alkyl, a protecting group or a promoiety;

$R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl; and the circle is a cyclic structure having 4 to 6 ring atoms.

2. The compound according to claim 1 wherein m and n=1, 2 or 3.

3. The compound according to claim 1, wherein:

$R^1$, $R^3$, $R^4$ and $R^{6-10}$=hydrogen;

$R^2$ and $R^5$=methyl; and the circle represents a heterocyclic structure selected from pyrrolidines—

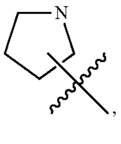

pyrroles—

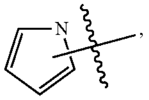

pyrazoles—,

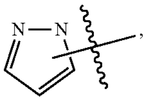

imidazoles—

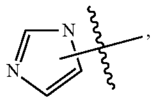

tetrahydrofurans—

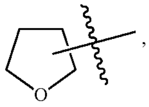

furans—

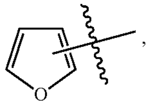

thiolane—

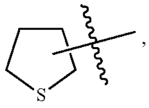

thiophene—

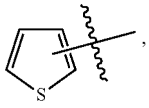

oxazole—

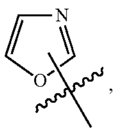

isoxazoles—

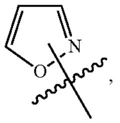

and thiazoles—

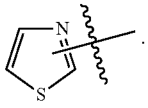

4. The compound according to claim 3 wherein the circle is a pyrazole or an isoxazole.

5. The compound according to claim 1, having a Formula II

Formula II

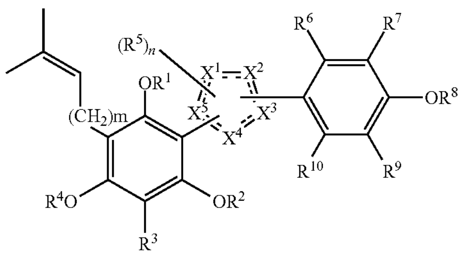

where:

m and n are 1, 2 or 3;

$R^1$-$R^4$ and $R^6$-$R^{10}$ are independently selected from H, $C_1$-$C_{10}$ alkyl, a protecting group or a promoiety;

$R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl; and X is independently C, N, O, S, or combinations thereof.

6. The compound according to claim 5, wherein:

$R^1$, $R^3$, $R^4$ and $R^{6-10}$=hydrogen;

$R^2$ and $R^5$=methyl; and

X=N.

7. The compound according to claim 5, having a formula

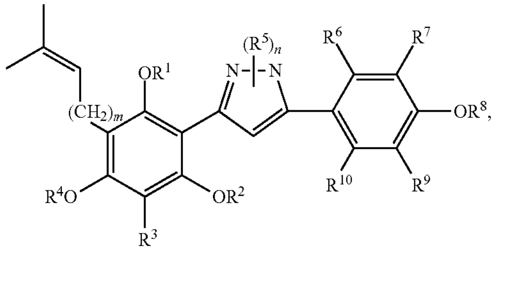

or

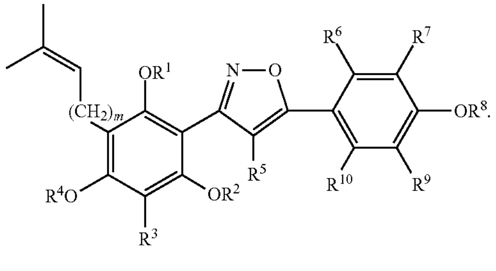

8. The compound according to claim 1, having a Formula III

Formula III

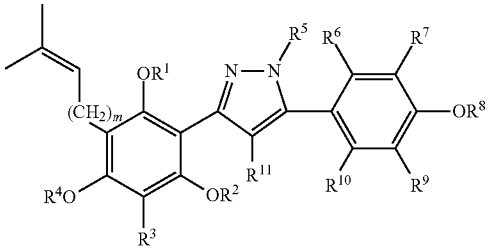

where:

m is 1, 2 or 3; and $R^1$-$R^4$ and $R^6$-$R^{11}$ are independently selected from H, $C_1$-$C_{10}$ alkyl, a protecting group or a promoiety; and $R^5$ is selected from $C_1$-$C_{10}$ alkyl, $C_3$-$C_{10}$ cycloalkyl, $C_3$-$C_{10}$ heterocyclyl, $C_5$-$C_6$ aryl and $C_5$-$C_6$ heteroaryl.

9. The compound according to claim 8 wherein $R^1$-$R^{11}$ are independently H and methyl.

10. The compound according to claim 1, selected from 4-(5-(4-hydroxyphenyl)-1-methyl-1H-pyrazol-3-yl)-5-methoxy-2-(3-methylbut-2-en-1-yl)benzene-1,3-diol

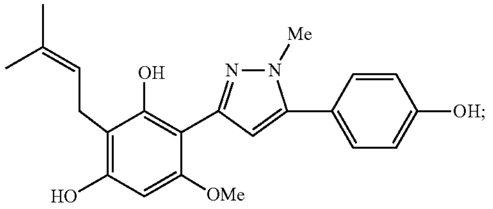 [SMILES: COc1cc(O)c(CC=C(C)C)c(O)c1-c1cc(-c2ccc(O)cc2)n(C)n1]

and 4-(5-(4-hydroxyphenyl)isoxazole-3-yl)-5-methoxy-2-(3-methylbut-2-en-1-yl)benzene-1,3-diol

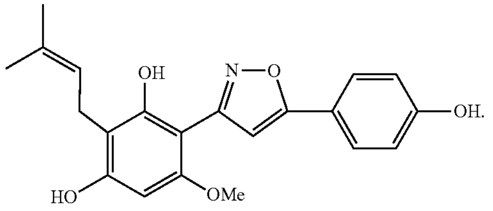 [SMILES: COc1cc(O)c(CC=C(C)C)c(O)c1-c1cc(-c2ccc(O)cc2)on1]

11. A composition, comprising:

a compound according to claim 1 in an amount ranging from 0.1 mg to 500 mg per dosage; and a pharmaceutically acceptable excipient selected from binding agents, fillers, lubricants, emulsifiers/solubilizers, coloring agents, flavoring agents, and combinations thereof.

12. The composition according to claim 11 formulated for administration as a dietary supplement or drug.

13. The composition according to claim 11 comprising at least one additional active compound.

14. The composition according to claim 11, wherein the pharmaceutically acceptable excipient is selected from oleic acid, ethylene glycol, propylene glycol, polysorbate 80, polysorbate 60, polysorbate 40, polysorbate 20, or combinations thereof.

15. The composition according to claim 11, wherein the compound is 4-(5-(4-hydroxyphenyl)-1-methyl-1H-pyrazol-3-yl)-5-methoxy-2-(3-methylbut-2-en-1-yl)benzene-1,3-diol

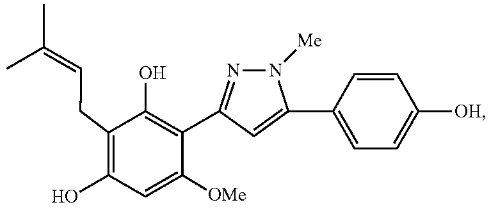 [SMILES: COc1cc(O)c(CC=C(C)C)c(O)c1-c1cc(-c2ccc(O)cc2)n(C)n1]

, or 4-(5-(4-hydroxyphenyl)isoxazole-3-yl)-5-methoxy-2-(3-methylbut-2-en-1-yl)benzene-1,3-diol

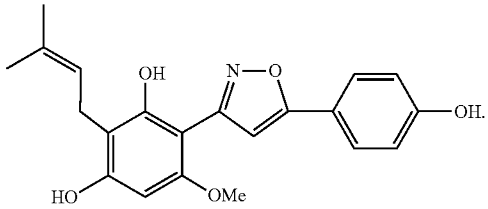 [SMILES: COc1cc(O)c(CC=C(C)C)c(O)c1-c1cc(-c2ccc(O)cc2)on1]

.

16. A method for treating, ameliorating, or preventing metabolic syndrome, obesity, diabetes, and/or cardiovascular disease, comprising administering to a subject for an administration period of greater than 0 days and up to at least 6 months a compound according to claim 1, or a composition comprising the compound according to claim 1, wherein administering the compound to the subject reduces weight gain or reduces body weight in the subject at least during the period of administration relative to the subject if not administered the compound or a composition comprising the compound.

17. The method according to claim 16 wherein weight gain or body weight by the subject is reduced by 2% to 20% relative to the subject if not administered the compound.

18. The method according to claim 16, wherein:

the compound has anti-inflammatory activity when plasma concentration of the compound is greater than 0 nM up to least 25 μM;

blood glucose concentration is reduced in the subject by greater than 0% to 50% after ingestion of a carbohydrate relative to the glucose concentration in the subject if the subject ingests the carbohydrate but is not administered the compound;

insulin resistance score, expressed as HOMA-IR, is reduced by at least 5% in a subject administered the compound relative to the subject if not administered the compound;

energy expenditure increases by at least 5% in a subject administered the relative to the subject if not administered the compound; and/or ambulatory locomotor activity increases by at least 5% in the subject administered the compound relative to the subject if not administered the compound; and/or mean respiratory exchange ratio increases from greater than 0% to 50% in a subject administered the compound relative to the subject if not administered the compound.

19. The method according to claim 16, comprising administering an effective amount of 4-(5-(4-hydroxyphenyl)-1-methyl-1H-pyrazol-3-yl)-5-methoxy-2-(3-methylbut-2-en-1-yl)benzene-1,3-diol

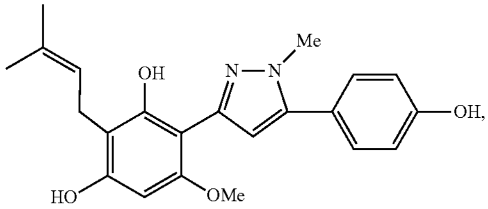 [SMILES: COc1cc(O)c(CC=C(C)C)c(O)c1-c1cc(-c2ccc(O)cc2)n(C)n1]

, or a composition comprising 4-(5-(4-hydroxyphenyl)-1-methyl-1H-pyrazol-3-yl)-5-methoxy-2-(3-methylbut-2-en-1-yl)benzene-1,3-diol, to a subject to improve glucose tolerance, decrease diet-induced obesity, and/or to induce increased energy expenditure relative to subject that is not administered 4-(5-(4-hydroxyphenyl)-1-methyl-1H-pyrazol-3-yl)-5-methoxy-2-(3-methylbut-2-en-1-yl)benzene-1,3-diol.

* * * * *